United States Patent
Helms et al.

(10) Patent No.: US 10,710,065 B2
(45) Date of Patent: Jul. 14, 2020

(54) POLYMERIC MATERIALS FOR ELECTROCHEMICAL CELLS AND ION SEPARATION PROCESSES

(71) Applicant: The Regents of the University of California, Oakland, CA (US)

(72) Inventors: Brett A. Helms, San Francisco, CA (US); Changyi Li, Berkeley, CA (US); Ashleigh Ward, Berkeley, CA (US); Sean E. Doris, San Francisco, CA (US); Peter D. Frischmann, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 205 days.

(21) Appl. No.: 15/563,557

(22) PCT Filed: Apr. 1, 2016

(86) PCT No.: PCT/US2016/025712
§ 371 (c)(1),
(2) Date: Sep. 29, 2017

(87) PCT Pub. No.: WO2016/161367
PCT Pub. Date: Oct. 6, 2016

(65) Prior Publication Data
US 2018/0085744 A1    Mar. 29, 2018

Related U.S. Application Data

(60) Provisional application No. 62/142,934, filed on Apr. 3, 2015, provisional application No. 62/194,138, filed
(Continued)

(51) Int. Cl.
*B01J 41/13*        (2017.01)
*H01M 8/0239*       (2016.01)
(Continued)

(52) U.S. Cl.
CPC .............. *B01J 41/13* (2017.01); *B01D 69/02* (2013.01); *B01D 71/62* (2013.01); *B01D 71/82* (2013.01);
(Continued)

(58) Field of Classification Search
CPC .... H01M 8/0239; H01M 2/1653; B01J 41/13; B01D 69/02; B01D 71/62; B01D 71/82;
(Continued)

(56) References Cited

U.S. PATENT DOCUMENTS

| 4,397,922 A | 8/1983 | Pokhodenko et al. |
| 6,586,138 B2 | 7/2003 | Pekala et al. |

(Continued)

FOREIGN PATENT DOCUMENTS

| WO | 2005/012397 A2 | 2/2005 |
| WO | 2005/113121 A1 | 12/2005 |
| WO | 2012/129411 A1 | 9/2012 |

OTHER PUBLICATIONS

Hart, K. E., & Colina, C. M. (2014). Ionomers of Intrinsic Microporosity: In Silico Development of Ionic-Functionalized Gas-Separation Membranes. Langmuir, 30(40), 12039-12048. doi: dx.doi.org/10.1021/la5027202 (Year: 2014).*

(Continued)

*Primary Examiner* — James Lee
(74) *Attorney, Agent, or Firm* — Kilpatrick Townsend & Stockton LLP

(57) ABSTRACT

Polymers of intrinsic microporosity are provided herein. Disclosed polymers of intrinsic microporosity include modified polymers of intrinsic microporosity that include negatively charged sites or crosslinking between monomer units. Systems making use of polymers of intrinsic microporosity and modified polymers of intrinsic microporosity are also described, such as electrochemical cells and ion separation
(Continued)

systems. Methods for making and using polymers of intrinsic microporosity and modified polymers of intrinsic microporosity are also disclosed.

20 Claims, 40 Drawing Sheets

Related U.S. Application Data on Jul. 17, 2015, provisional application No. 62/307,309, filed on Mar. 11, 2016.

(51) Int. Cl.

| | | |
|---|---|---|
| *C07D 491/22* | (2006.01) | |
| *C07D 493/22* | (2006.01) | |
| *C08J 5/22* | (2006.01) | |
| *B01D 71/62* | (2006.01) | |
| *B01D 71/82* | (2006.01) | |
| *B01D 69/02* | (2006.01) | |
| *C07D 241/46* | (2006.01) | |
| *H01M 4/36* | (2006.01) | |
| *H01M 4/38* | (2006.01) | |
| *H01M 4/58* | (2010.01) | |
| *H01M 8/18* | (2006.01) | |

(52) U.S. Cl.
CPC ......... *C07D 241/46* (2013.01); *C07D 491/22* (2013.01); *C07D 493/22* (2013.01); *C08J 5/2256* (2013.01); *H01M 4/368* (2013.01); *H01M 4/382* (2013.01); *H01M 4/5815* (2013.01); *H01M 8/0239* (2013.01); *H01M 8/188* (2013.01); *B01D 2325/02* (2013.01); *C08J 2371/00* (2013.01); *H01M 2300/0028* (2013.01)

(58) Field of Classification Search
CPC .. C07D 241/46; C07D 491/22; C07D 493/22; C08J 5/2256
See application file for complete search history.

(56) References Cited

U.S. PATENT DOCUMENTS

| | | |
|---|---|---|
| 7,690,514 B2 | 4/2010 | McKeown et al. |
| 8,056,732 B2 | 11/2011 | McKeown et al. |
| 9,481,939 B2 | 11/2016 | Masel et al. |
| 9,580,824 B2 | 2/2017 | Masel et al. |
| 2006/0246273 A1* | 11/2006 | McKeown ........... B01D 53/228 428/314.8 |
| 2012/0264589 A1 | 10/2012 | Du et al. |
| 2014/0255636 A1* | 9/2014 | Odeh .................... B01D 71/58 428/36.5 |
| 2019/0109310 A1 | 4/2019 | Masel et al. |

OTHER PUBLICATIONS

Du, Naiying, et al. "Azide-Based Cross-Linking of Polymers of Intrinsic Microporosity (PIMs) for Condensable Gas Separation." Macromolecular Rapid Communications, vol. 32, No. 8, 2011, pp. 631-636., doi: 10.1002/marc.201000775 (Year: 2011).*
PCT/US2016/025712, "International Search Report and Written Opinion," dated Sep. 8, 2016, 33 pages.
Li et al, "Polysulfide-Blocking Microporous Polymer Membrane Tailored for Hybrid Li-Sulfur Flow Batteries," Nano Letters 15(9), pp. 5724-5729 (2015).
Li, et al., "A Polysulfide-Blocking Microporous Polymer Membrane Tailored for Hybrid Li-Sulfur Flow Batteries," ACS Nano Letters 2015, Supporting Information, 11 pages.
McKeown et al., "Polymers of Intrinsic Microporosity (PIMs): Bridging the Void Between Microporous and Polymeric Materials," Chem. Eur. J. 11(9), pp. 2610-2620 (2005).
McKeown, "Polymers of Intrinsic Microporosity," International Scholarly Research Network, vol. 2012, Article ID 513986, 16 pages.
Khan, et al., "Cross-Linking of Polymer of Intrinsic Microporosity (PIM-1) via nitrene reaction and its effect on gas transport property," European Polymer Journal 49 pp. 4157-4166 (2013).
Madrid, et al., "Metastable Ionic Diodes Derived from an Amine-Based Polymer of Intrinsic Microporosity," Angew. Chem. Int. Ed. 2014, 53, pp. 10751-10754.

* cited by examiner

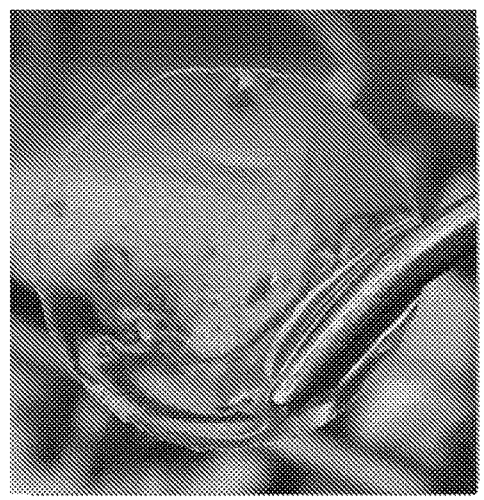
FIG. 5
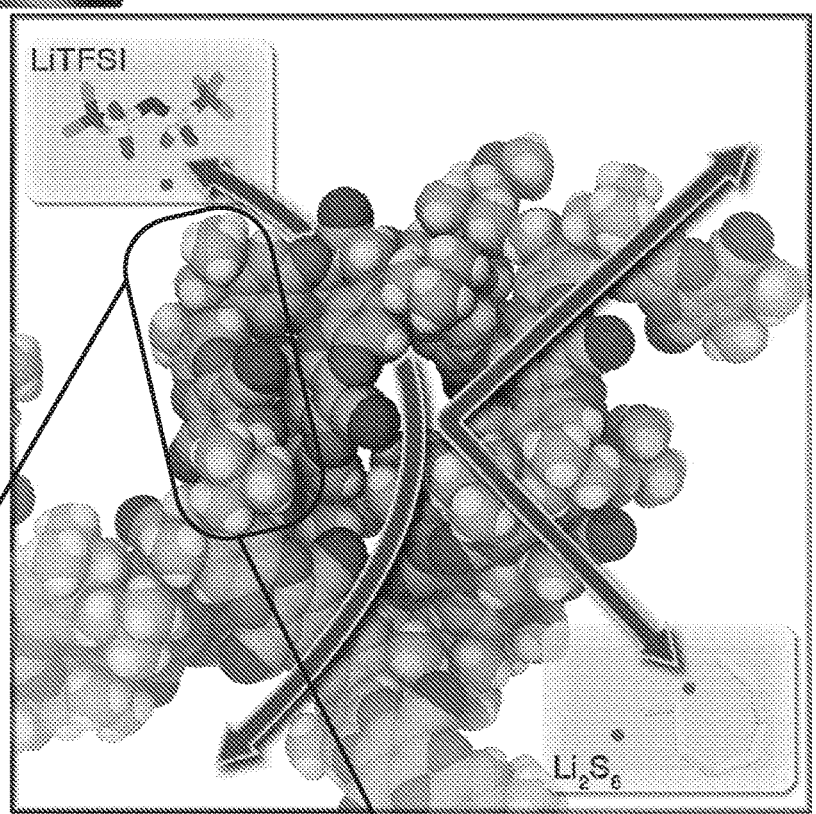
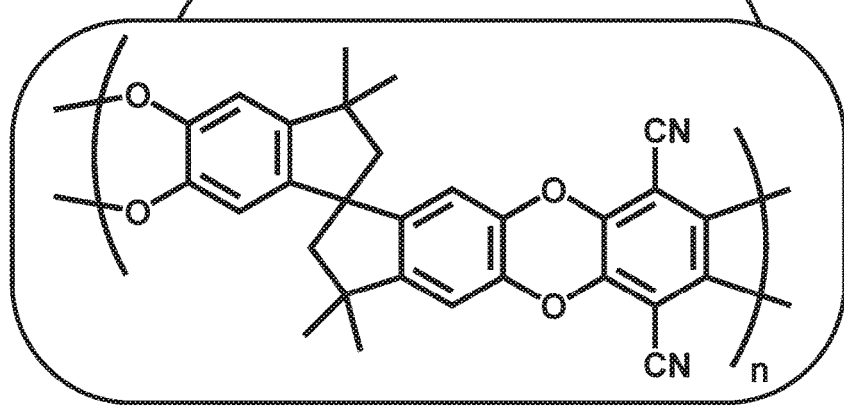

POLYMERIC MATERIALS FOR ELECTROCHEMICAL CELLS AND ION SEPARATION PROCESSES

CROSS-REFERENCES TO RELATED APPLICATIONS

This application is a U.S. National Stage Entry under 35 U.S.C. § 371 of PCT International Application No. PCT/US2016/025712, filed Apr. 1, 2016, which claims the benefit of and priority to U.S. Provisional Patent Application Nos. 62/142,934, filed Apr. 3, 2015, 62/194,138, filed Jul. 17, 2015, and 62/307,309 filed Mar. 11, 2016, each of which is incorporated in its entirety herein for all purposes.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy. The government has certain rights in the invention.

BACKGROUND OF THE INVENTION

Membranes (or separators) are critical for ionic conduction and electronic isolation in many electrochemical devices. For cell architectures that utilize redox-active species that are dissolved, dispersed, or suspended in electrolyte, including fuel cells (FCs), redox flow batteries (RFBs), and conversion reaction electrodes, it is also of value that the membrane prevent active material crossover that would otherwise contribute to device shorting, electrode fouling, or irrevocable loss in capacity. Unfortunately, commercial battery separators, which feature shape-persistent mesopores, are freely permeable to most active materials used in RFBs and electrolyte soluble intermediates formed in conversion reaction electrodes. Alternative membrane separators have thus far relied heavily on variants of aqueous single-ion conductors, e.g., Nafion, which may ultimately restrict the use of certain types of flowable electrodes. Despite the wide availability of porous materials that might serve effectively as membrane components, including zeolites, metal-organic frameworks, covalent organic frameworks, carbon nanotubes, cyclic peptide nanotubes, and microporous polymers, rational design rules for achieving ion-selective transport via sieving in battery membranes have not been established.

BRIEF SUMMARY OF THE INVENTION

The present description provides separator systems that are useful in a variety of electrochemical cells, including lithium-sulfur batteries and redox-flow batteries, as well as in ion-separation processes. The disclosed separator systems make use of polymers of intrinsic microporosity to selectively restrict passage of particular ions through the separator. Due to their wide diversity and structural properties, polymers of intrinsic microporosity may be advantageous for separator systems. Polymers of intrinsic microporosity may advantageously be selected based on their inherent pore size to selectively restrict large ions by size sieving, while allowing smaller ions to transport through the pores. Additionally or alternatively, polymers of intrinsic microporosity may be modified to aid in the restriction of ion transport, such as by imparting negative charges to the polymer structure, which may further provide an electrostatic restriction on anionic species, or by crosslinking the polymer, which may provide for further improved size sieving properties.

In some embodiments, polymers of intrinsic microporosity are provided. In some embodiments, polymers of intrinsic microporosity may be modified. A modified polymer of intrinsic microporosity of some embodiments comprises a polymer of intrinsic microporosity having a plurality of repeat units, wherein at least one of the repeat units includes one or more negative charges. A modified polymer of intrinsic microporosity of some embodiments comprises a polymer of intrinsic microporosity having a plurality of repeat units, wherein one or more non-adjacent repeat units are crosslinked. A modified polymer of intrinsic microporosity of some embodiments comprises a polymer of intrinsic microporosity having a plurality of repeat units, wherein at least one of the repeat units includes one or more negative charges, and wherein one or more non-adjacent repeat units are crosslinked. For example, in some embodiments, the non-adjacent repeat units correspond to different polymer chains.

Polymers of intrinsic microporosity of some embodiments may further be provided in contact with a support membrane. Inclusion of a support membrane may be useful with polymers of intrinsic microporosity to provide additional features or functionality to the polymers of intrinsic microporosity, such as additional structural strength, a shape or form template, or safety features, for example. Additionally, inclusion of a support membrane with a polymer of intrinsic microporosity may facilitate use of the polymer of intrinsic microporosity as a separator in an electrochemical cell or as separation membrane in an ion selective separation process.

In some embodiments, the present invention provides methods of making modified polymers of intrinsic microporosity, such as the modified polymers of intrinsic microporosity described above. In one embodiment, a method of making a modified polymer of intrinsic microporosity comprises forming a reaction mixture comprising a polymer of intrinsic microporosity and a reducing agent under conditions sufficient to form the modified polymer of intrinsic microporosity. In embodiments, reaction of a polymer of intrinsic microporosity with a reducing agent results in one or more of the repeat units of the polymer of intrinsic microporosity being modified to include a negative charge, such as by way of a reduction reaction with the reducing agent. In one embodiment, a method of making a modified polymer of intrinsic microporosity comprises forming a reaction mixture comprising a polymer of intrinsic microporosity and a nucleophile under conditions sufficient to form the modified polymer of intrinsic microporosity. In embodiments, reaction of a polymer of intrinsic microporosity with a nucleophile results in one or more of the repeat units of the polymer of intrinsic microporosity being modified to include a negative charge, such as by way of a nucleophilic addition reaction with the nucleophile. In one embodiment, a method of making a modified polymer of intrinsic microporosity comprises forming a reaction mixture comprising a polymer of intrinsic microporosity and a crosslinking agent under conditions sufficient to form the modified polymer of intrinsic microporosity. In some embodiments, reaction of a polymer of intrinsic microporosity with or by the crosslinking agent results in covalent linkages being formed between non-adjacent repeat units. For example, in some embodiments, reaction of a polymer of intrinsic microporosity with or by the crosslinking agent results in covalent linkages being formed between different polymer chains.

In some embodiments, the present invention provides electrochemical cells. In one embodiment, an electrochemical cell comprises an anode, an anode electrolyte in contact with the anode, a separator in contact with the anode electrolyte, wherein the separator comprises a polymer of intrinsic microporosity, a cathode electrolyte in contact with the separator, and a cathode in contact with the cathode electrolyte. Optionally, the polymer of intrinsic microporosity is a modified polymer of intrinsic microporosity, such as the modified polymers of intrinsic microporosity described above. Optionally, the polymer of intrinsic microporosity is an unmodified polymer of intrinsic microporosity.

In some embodiments, the present invention provides methods of selective ion transport. In one embodiment, a method of selective ion transport comprises contacting a first side of a separator with a first ionic solution; and contacting a second side of the separator with a second ionic solution, wherein the separator comprises a polymer of intrinsic microporosity. Optionally, the polymer of intrinsic microporosity is a modified polymer of intrinsic microporosity, such as the modified polymers of intrinsic microporosity described above. In embodiments, the first ionic solution comprises a first ionic species and the separator allows transport of the first ionic species between the first ionic solution and the second ionic solution through the separator. In embodiments, the second ionic solution comprises a second ionic species and the separator provides a size selective restriction on transport of the second ionic species from the second ionic solution to the first ionic solution through the separator. Optionally, the separator provides an electrostatic restriction on transport of the second ionic species through the separator.

BRIEF DESCRIPTION OF THE DRAWINGS

FIG. 5 provides a photograph of a film comprising a polymer of intrinsic microporosity (top left), the chemical structure of a polymer of intrinsic microporosity (bottom left), and a schematic illustration of a molecular model of the polymer of intrinsic microporosity (right).

DETAILED DESCRIPTION OF THE INVENTION

I. General

Figure 1A:
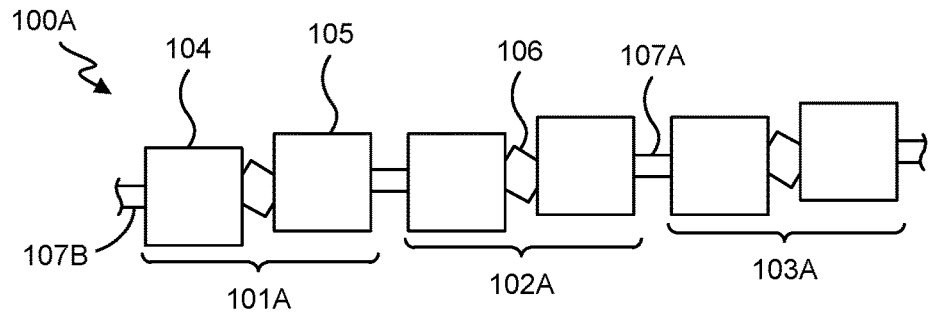
FIG. 1A provides a schematic illustration of a polymer of intrinsic microporosity in accordance with some embodiments.

The present invention relates generally to unmodified and modified polymers of intrinsic microporosity and techniques for making and modifying polymers of intrinsic microporosity, such as to impart particular characteristics to the polymers, such as useful pore sizes, crosslinking character, and charge structure. For example, in some embodiments, polymers of intrinsic microporosity may be modified through reactions with reducing agents and/or nucleophiles to modify the polymers of intrinsic microporosity in a way that provides negative charges to or throughout the polymers. Additionally or alternatively, in some embodiments, polymers of intrinsic microporosity may be modified by crosslinking. These modifications may enhance the utility of the modified polymers of intrinsic microporosity for a variety of solution phase applications.

Inclusion of negative charges may be useful, in some embodiments, for improving the functionality of a polymer of intrinsic microporosity as an ion separation structure or selectively permeable membrane. For example, the unmodified and modified polymers of intrinsic microporosity may be used as electrochemical cell separators or ion separation membranes, and the presence of the negative charges in the modified polymers of intrinsic microporosity may impact, through electrostatic effects, which sizes and types of ions in a solution are permitted to pass through the separators or membranes and which sizes and types of ions in a solution are restricted from passing through the separators or membranes.

Similarly, the presence and/or extent of crosslinking of modified polymers of intrinsic microporosity may enhance the functionality of a polymer of intrinsic microporosity as an ion separation structure or selectively permeable membrane. For example, modified polymers of intrinsic microporosity that are crosslinked may also be used as electrochemical cell separators or ion separation membranes, and the presence and/or extent of crosslinking may impact, through size sieving effects, which sizes and types of ions in a solution are permitted to pass through the separators or membranes and which sizes and types of ions in a solution are restricted from passing through the separators or membranes.

In some embodiments, unmodified polymers of intrinsic microporosity are useful as an ion separation structure or selectively permeable membrane, such as in an electrochemical cell separator or ion separation membrane. Selection of a particular structure for an unmodified polymer of intrinsic microporosity may, in some embodiments, determine the size of the pores of the polymer which may impact the size sieving effects of the polymer for permitting/restricting particular sizes and types of ions in solution from passing through the separators or membranes.

In some embodiments, these characteristics make polymers of intrinsic microporosity and modified polymers of intrinsic microporosity useful for specific electrochemical cell systems, such as lithium-sulfur battery systems, where undesirable reactions with the electrolytes can result in irreversible loss of capacity. For example, although the fully charged cathode material ($S_8$) and the fully discharged cathode material ($Li_2S$) may be generally insoluble in most electrolytes, the intermediates (i.e., $Li_2S_2$, $Li_1S_3$, $Li_2S_4$, $Li_2S_6$, $Li_2S_8$) may have high electrolyte solubility. If the intermediates are able to pass from the cathode electrolyte to the anode electrolyte and contact the lithium containing anode, they may react with the anode and result in a permanent loss of the active sulfur cathode material. Advantageously, the unmodified and modified polymers of intrinsic microporosity may be able to stop and/or reduce the rate at which the intermediates may cross from the cathode electrolyte to the anode electrolyte.

II. Definitions

"Polymer" refers to a molecule composed of repeating structural units, referred to herein as monomers or repeat units, connected by covalent chemical bonds or the polymerization product of one or more monomers. Polymers may be characterized by a high molecular weight, such as a molecular weight greater than 100 atomic mass units (amu), greater than 500 amu, greater than 1000 amu, greater than 10000 amu or greater than 100000 amu. In some embodiments, a polymer may be characterized by a molecular weight provided in g/mol or kg/mol, such as a molecular weight of about 200 kg/mol or about 80 kg/mol. The term polymer includes homopolymers, or polymers consisting essentially of a single repeating monomer subunit. The term polymer also includes copolymers, which are formed when two or more different types of monomers are linked in the same polymer. Copolymers may comprise two or more monomer subunits, and may include random, block, alternating, segmented, grafted, tapered and other copolymers. Useful polymers include organic polymers that may be in amorphous, semi-amorphous, crystalline or partially crystalline states. Crosslinked polymers having monomer units that are linked to other polymer molecules or other parts of the same polymer molecule are useful for some applications.

"Repeat unit" refers to a part of a polymer that represents a repetitive structure of the polymer chain, the repetition of which would make up the complete polymer chain with the exception of end groups corresponding to terminal ends of the polymer chain. In some embodiments, a repeat unit may also be referred to herein as a monomer. Repeat units may be identified in a polymer structure by brackets or parentheses and include a subscript n, which represents the degree of polymerization. In some embodiments, values for subscript n include integers selected from, for example, 10 to 1000, 50 to 900, 100 to 800, or 200 to 500. In some embodiments, subscript n is an integer more than 1000. It will be appreciated that a value for subscript n in a polymer may not be explicitly provided, consistent with use by skilled artisans in the field of polymers. In the following polymer structure, RU corresponds to a repeat unit of the polymer:

"Microporosity" refers to a characteristic of a material describing the inclusion of voids, channels, openings, recessed regions, etc., also referred to herein as micropores, in the body of material. Optionally, the micropores have a cross sectional dimension of about 2 nm or less. In some embodiments, micropores may have a cross sectional dimension of about 1.7 nm or less, 1.5 nm or less, 1.2 nm or less, 1 nm or less, or 0.8 nm or less. Optionally, micropores may have cross sectional dimensions selected from the range of 0.5 nm to 2 nm, selected from the range of 0.5 nm to 1.2 nm, or selected from the range of 1.2 nm to 1.7 nm. The inclusion of micropores in a material may allow for other materials, such as gases, liquids, ions, etc., to pass through the micropores.

"Intrinsic microporosity" refers to a continuous network of interconnected voids in a material formed as a direct consequence of the shape and rigidity of the components of the material. Intrinsic microporosity is achieved in some polymers by the polymers possessing individual structural units that are rigid and that may be oriented relative to one another in such a way that the structural units align to form an opening or pore. Additionally or alternatively, a polymer possessing intrinsic microporosity may have a structure that exhibits frustrated packing. Frustrated packing of a polymer may occur when a polymer molecule contacts itself or other like polymer molecules and the rigidity of the molecule(s) causes the molecule(s) to lie in a configuration where spaces between the molecule(s) are created. Such spaces may correspond to micropores in a film or membrane made of the polymer molecules, for example.

"Polymer of intrinsic microporosity" refers to a polymer that exhibits microporosity due to the shape and rigidity of the molecular structure of the repeat units within the polymer, where the repeat units may align relative to one another such that spaces or openings are generated along the polymer chain. Additionally or alternatively, the repeat units may align in an aggregate of the polymer in a way that frustrates packing of the polymer molecules in the aggregate such that spaces or openings are generated between different polymer molecules and/or between segments of the same polymer molecule. These spaces within the aggregated polymer may, at least in part, provide the microporosity to such a polymer. Due to the inclusion of the micropores, some polymers of intrinsic microporosity may exhibit high surface areas, such as a surface area selected from the range of 300 $m^2$ $g^{-1}$ to 1500 $m^2$ $g^{-1}$.

Polymers of intrinsic microporosity of some embodiments include a chain of repeat units (i.e., monomers) where adjacent repeat units are covalently bonded such that they are non-rotatable with respect one another, which may provide a degree of rigidity to the polymer chain. Such a non-rotatable covalent bonding configuration between adjacent repeat units may, for example, be due to the presence of multiple bonds between adjacent repeat units and/or a multi-order bond (e.g., a double bond) between adjacent repeat units. In some embodiments, adjacent repeat units in the chain may include portions which may be connected by single bonds but are sterically restricted from rotating, for example due to the size of the portions connected by single bonds. A steric restriction on rotation may, in part, provide a degree of rigidity to the polymer chain, in some embodiments.

Additionally, repeat units of polymers of intrinsic microporosity may further include rigid moieties that exhibit planarity, such as aromatic ring containing moieties, heteroaromatic ring containing moieties, and polycyclic moieties including aromatic or heteroaromatic structures, for example. In some embodiments, multiple portions of a repeat units, such as different planar structures, are covalently bonded such that they are non-rotatable with respect one another, which may provide a degree of rigidity to the polymer chain. Such a non-rotatable covalent bonding configuration between repeat unit portions may, for example, be due to the presence of a non-rotatable linking group providing covalent bonding between the repeat unit portions, such as multiple bonds between repeat unit portions, a multi-order bond (e.g., a double bond) between repeat unit portions, or a linking group including a fused ring structure. In some embodiments, repeat units may include portions which may be connected by single bonds but are sterically restricted from rotating, for example due to the size of the portions connected by single bonds. A steric restriction on rotation may, in part, provide a degree of rigidity to the polymer chain, in some embodiments.

Additionally, some or all of the repeat units may include a rigid linking moiety between different planar moieties that function to orient the different planar moieties in non-coplanar orientations. Such a rigid linking moiety may include, for example, a non-aromatic cyclic moiety, or a non-aromatic polycyclic moiety, or a combination of an aromatic or heteroaromatic moiety and a non-aromatic moiety. Useful rigid linking moieties include bridged ring moieties. Useful rigid linking moieties include cyclic spiro moieties, where two ring structures are provided in a fused configuration where only one atom is shared by the two rings. The inclusion of a rigid linking moiety within a repeat unit that orients planar moieties unit in non-coplanar orientations may further serve to give the repeat unit a structure that results in frustrated packing of the polymer within an aggregated polymer of intrinsic microporosity such that the repeat units arrange in a structure where space is provided between the repeat units.

In some embodiments, a polymer of intrinsic microporosity does not possess a crosslinked network of covalent bonds, and microporosity is provided to the polymer due to the rigid structure of the repeat units. The term "non-network polymer" may refer to a polymer that does not possess a crosslinked network of covalent bonds between non-adjacent repeat units, such as repeat units that may be on different polymer molecules, for example. Some polymers of intrinsic microporosity may be modified, however, through chemical and/or physical processes to generate a crosslinked structure that may retain the microporosity character, at least in part. For example, some polymers of intrinsic microporosity may be crosslinked by exposure to ultraviolet radiation and/or microwave radiation. Additionally or alternatively, some polymers of intrinsic microporosity may be crosslinked by heating. Additionally or alternatively, some polymers of intrinsic microporosity may be crosslinked by exposure to a crosslinking agent, such as 2,6-bis(4-azidobenzylidene)cyclohexanone, 2,6-bis(4-azidobenzylidene)-4-methylcyclohexanone, 2,6-bis(4-azidobenzylidene)-4-ethylcyclohexanone, or 4-azidophenylsulfone. In some embodiments, oxygen may serve as a crosslinking agent.

Example polymers of intrinsic microporosity are described in U.S. Pat. Nos. 7,690,514 and 8,056,732, PCT International Patent Publications WO 2005/012397 and WO 2005/113121, and "Polymers of Intrinsic Microporosity" a review article by Neil B. McKeown (ISRN Materials Science, Volume 2012, Article ID 513986), each of which are hereby incorporated by reference.

In some embodiments, a polymer of intrinsic microporosity does not possess a charged moiety. In some embodiments, repeat units of a modified polymer of intrinsic microporosity possess a charged moiety. It will be appreciated that introduction of charged moieties may be achieved, in some embodiments, through chemical modification of a polymer of intrinsic microporosity, such by reacting a polymer of intrinsic microporosity with a reducing agent and/or a nucleophile.

It will be appreciated that, in some embodiments, polymers of intrinsic microporosity may be modified to include any useful chemical functionality.

"Charged moiety" refers to a part or functional group of a compound that possesses a positive or negative charge. The positive or negative charge of a compound may be delocalized or shared by different atoms in the compound, such as may be indicated by different resonance structural representations of the compound.

"Reducing agent" and "electron donor" refers to a chemical species that provides an electron to another chemical species in a redox reaction involving the two species. The chemical species that receives the electron may be referred to as an "oxidizing agent" or an "electron acceptor." In some embodiments, a reducing agent refers to an agent capable of reducing an atom from a higher oxidation state to a lower oxidation state.

Any suitable reducing agent is useful in the method of the present invention. For example, reducing agents include, but are not limited to, an alkali metal polysulfide, such as $Li_2S_m$, where subscript m is an integer selected from 2 to 100. Other reducing agents are known to one of skill in the art, such as those in "Comprehensive Organic Transformations", 1st edition, Richard C. Larock, VCH Publishers, New York, 1989.

"Oxidation potential" refers to a measure of the energy change needed to remove an electron from an atom or a compound. Oxidation potentials may be provided as a voltage and may be referenced to a standard hydrogen electrode (SHE), i.e., a voltage amount greater than or less than that required for the reaction of $½H_2$ (gas)→$H^+$ (solution)+$e^-$.

"Nucleophile" refers to a chemical species that reacts with another species to form a covalent bond with the other species by providing pair of electrons to form the bond. The species with which a nucleophile reacts may be referred to as an "electrophile." Generally, a nucleophile will possess a lone pair of electrons that can participate in the bond forming reaction. In some embodiments, a nucleophile may be referred to as a Lewis base. In some embodiments, a nucleophile may be an anionic species. In some embodiments, a nucleophile may react with an electrophile in a nucleophilic addition reaction where components of the nucleophile and the electrophile are combined in the reaction product.

"Crosslink" refers to a process by which covalent bonds are formed between separate polymer molecules or between separate monomer sites on the same polymer molecule. A "crosslink" may also refer to a covalent bond formed between separate polymer molecules or between separate monomer sites on the same polymer molecule. A crosslink may also refer to a chemical species of one or more atoms that forms covalent bonds with separate polymer molecules or between separate monomer sites on the same polymer molecule.

"Crosslinking agent" refers to a composition used to facilitate forming crosslinks between separate polymer molecules or between separate monomer sites on the same polymer molecule. Some crosslinking agents may, for example, be a catalyst that is not covalently incorporated into the polymer molecule but merely increases a crosslinking rate and/or lowers an energy requirement for a crosslinking reaction. Some crosslinking agents may be directly incorporated, at least in part, within a covalent link between polymer molecules or between separate monomer sites on the same polymer molecule. Example crosslinking agents include, but are not limited to, 2,6-bis(4-azidobenzylidene)cyclohexanone, 2,6-bis(4-azidobenzylidene)-4-methylcyclohexanone, 2,6-bis(4-azidobenzylidene)-4-ethylcyclohexanone, and 4-azidophenylsulfone. In some embodiments, oxygen may serve as a crosslinking agent.

A crosslinking agent may also refer to the addition of energy to a polymer to form crosslinks between separate polymer molecules or between separate monomer sites on the same polymer molecule. For example, heat may be a crosslinking agent in some embodiments. Additionally or alternatively, ultraviolet radiation may be a crosslinking agent in some embodiments. Additionally or alternatively, microwave radiation may be a crosslinking agent in some embodiments.

"Electrochemical cell" refers to a device that produces electrical energy through chemical reactions. Example electrochemical cells include batteries and fuel cells. Batteries may include solid-state batteries, semi-solid batteries, wet cell batteries, dry cell batteries, flow batteries, primary batteries, secondary batteries, etc. A battery may refer to an assembly of a plurality of individual electrochemical cells, such as arranged in a series configuration. Example electrochemical cells include an anode, a cathode, a separator between the anode and the cathode, and an electrolyte. Electrochemical cells may further include a current collector in electrical contact with an electrode and/or an electrolyte and may be used, in part, to provide a conductive path between the electrode and a load.

"Anode" refers to an electrode in an electrochemical cell where oxidation occurs during discharge of the electrochemical cell. In some embodiments, an anode is identified in an electrochemical cell as the negative electrode, where electrons are emitted during discharge for use by a load. In some embodiments, an anode oxidizes material and releases positive ions to an electrolyte during discharge.

"Cathode" refers to an electrode in an electrochemical cell where reduction occurs during discharge of the electrochemical cell. In some embodiments, a cathode is identified in an electrochemical cell as the positive electrode, where electrons are received during discharge after use by a load. In some embodiments, a cathode reduces positive ions received from an electrolyte during discharge.

"Separator" refers to an ion conductive barrier used to separate an anode and a cathode in an electrochemical cell. In some embodiments, a separator is a porous or semipermeable membrane that restricts the passage of certain materials across the membrane. In some embodiments, a separator provides a physical spacing between the anode and the cathode in an electrochemical cell. In some embodiments, a separator is not electrically conductive and provides a gap in electrical conductivity between the anode and the cathode in an electrochemical cell.

"Electrolyte" refers to an ionically conductive substance or composition and may include solvents, ionic liquids, metal salts, ions such as metal ions or inorganic ions, polymers, ceramics, and other components. An electrolyte may be a solid, in some embodiments. An electrolyte may be a liquid, such as a solvent containing dissolved ionic species. An electrolyte may be used, in some embodiments, for transporting ions between an anode and a cathode in an electrochemical cell.

"Ionic solution" refers to a solvent including dissolved ionic species. An electrolyte is an example of an ionic solution. Useful solvents for ionic solutions include aqueous solvents containing water. Useful solvents for ionic solutions include non-aqueous solvents, such as organic solvents.

"Anode electrolyte" refers to an electrolyte in an electrochemical cell in contact with an anode. An anode electrolyte may also be referred to herein as an "anolyte." An anode electrolyte may further be in contact with a separator in an electrochemical cell.

"Cathode electrolyte" refers to an electrolyte in an electrochemical cell in contact with a cathode. A cathode electrolyte may also be referred to herein as a "catholyte." A cathode electrolyte may further be in contact with a separator in an electrochemical cell.

"Membrane" refers to a web of material that extends in lateral dimensions, which may be orthogonal to a thickness dimension of the membrane. In some embodiments, the term "membrane" may be used interchangeably herein with the term "film". Optionally, a membrane separates two regions in space by the physical materials that make up the membrane. A membrane may be used as a support or template for other materials in order to provide structure and/or stability to the other material, for example. The other material may be attached to one side of the membrane, and or may encapsulate all or portions of the membrane.

"Support membrane" refers to a structural film that may provide mechanical stability to another material coated onto or otherwise attached to the film. In some embodiments, a support membrane may be porous or otherwise allow materials, such as ions, gases, or liquids, to pass through the support membrane, though any coated or otherwise supported material may restrict, at least in part, the passage of the ions, gases, or liquids.

"Selective ion transport" refers to a process where ions of different chemical species exhibit different transport rates. For example, selective ion transport may refer to a process where ions of a particular species are restricted from moving, while ions of another species may be permitted to move. In some embodiments, selective ion transport may be achieved through use of a semi-permeable membrane, such as a separator.

"Alkali metal" refers to lithium, sodium, potassium, rubidium, cesium, and francium.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

III. Polymers of Intrinsic Microporosity

As described above, polymers of intrinsic microporosity are useful with some embodiments of the present invention. For example, polymers of intrinsic microporosity may be directly useful in systems of the invention, such as electrochemical cells and ion separation systems. Additionally, polymers of intrinsic microporosity may be useful as starting materials in methods of the invention, such as methods for making modified polymers of intrinsic microporosity and methods for selective ion transport.

It will be appreciated that many polymers of intrinsic microporosity may be useful with some embodiments described herein. Polymers of intrinsic microporosity may refer to a class of polymers that exhibit microporosity simply due to their chemical structure, which may include rigid (i.e., non-rotatable) moieties, such as ring systems, within the monomers of the polymer. The rigidity of the chemical structure may result in the polymer chain having spaces or openings between atoms of the polymer in a way that frustrates packing of the polymer chain such that an aggregate of the polymer (e.g., in a film) has a continuous network of openings or pores that may extend through all or a portion of the aggregate. The pore dimensions may be controlled by selective use of particular structural elements in the monomers that provide a degree of non-linearity to the chain. For example structural elements of the monomers may orient portions of monomers at an angle relative to one another such that the monomer has a bent character. Optionally, different portions of the monomer are planar and are provided in a non-coplanar orientation with respect to one another. For example, a linking structural element between the planar portions may orient the planar portions at an angle with respect to one another. The bent or non-coplanar character of a monomer may result in a polymer comprising a plurality of the monomers exhibiting spacings between portions of the polymer.

Polymers of intrinsic microporosity may include a plurality of repeat units linked in a chain configuration, and may be represented by a structure,

where RU refers to a repeat unit and where subscript n corresponds to a number of repeat units in the polymer molecule, also referred to as the degree of polymerization. In some embodiments, values for subscript n include integers selected from, for example, 10 to 1000, 50 to 900, 100 to 800, or 200 to 500. In some embodiments, subscript n is an integer more than 1000. It will be appreciated that, in many instances, a value for subscript n may not be directly provided in a chemical structure of a polymer of intrinsic microporosity, consistent with use in the field of polymers.

FIG. 1A provides a schematic illustration of an embodiment of a polymer of intrinsic microporosity 100A. Polymer of intrinsic microporosity 100A is depicted as including three repeat units 101A, 102A, and 103A. It will be appreciated that additional repeat units may be included in polymer of intrinsic microporosity 100A, but for sake of simplicity of illustration, these additional repeat units are not illustrated in FIG. 1A and broken non-rotatable bonds 107B illustrate connection points to additional repeat units. Each repeat unit 101A, 102A, and 103A includes a first repeat unit portion 104 and a second repeat unit portion 105. In the embodiment illustrated, first repeat unit portion 104 and second repeat unit portion 105 are covalently linked by a non-rotatable linker 106. Additionally, each of the repeat units are linked by a non-rotatable bond 107A. Non-rotatable bond 107B is depicted in FIG. 1A to represent covalent bonding to additional repeat units that are not depicted in FIG. 1A. In some embodiments, first repeat unit portion 104 includes one or more planar chemical moieties, such as an aromatic or heteroaromatic moiety. Similarly, second repeat unit portion 105 may include one or more planar chemical moieties, such as an aromatic or heteroaromatic moiety. Inclusion of planar chemical moieties in first repeat unit 104 and/or second repeat unit 105 may be advantageous as these chemical moieties may provide rigidity to the repeat units 101A, 102A, and 103A. Repeat units 101A and 102A may be referred to as adjacent repeat units since, for example, there are no repeat units between repeat units 101A and 102A. Repeat units 102A and 103A may be also referred to as adjacent repeat units. Repeat units 101A and 103A may, however, be referred to as non-adjacent repeat units since, for example, there is at least one repeat unit between repeat units 101A and 103A, namely repeat unit 102A. Accordingly, repeat units that are directly linked to one another may be referred to herein as "adjacent" and repeat units that are linked to one another through one or more intermediate repeat units may be referred to herein as "non-adjacent."

Non-rotatable linker 106 may comprise a moiety that includes a chiral center. Non-rotatable linker 106 may comprise a bridged ring moiety, such as a norbornane derivative. Non-rotatable linker 106 may comprise a cyclic spiro moiety, such as spirononane derivative, which may correspond to two fused five-membered rings that share a single atom.

Non-rotatable bonds 107A and 107B may comprise multiple covalent bonds between monomers, such as two individual single bonds, a combination of a single bond and a double bond, or two individual double bonds, for example. Such a configuration may arise, for example, by virtue of a fused ring structure, such as where a first ring structure on a first end of a first repeat unit is fused to a second ring structure on a second end of a second repeat unit through a linking ring structure between the repeat units.

A variety of polymers of intrinsic microporosity are useful with some embodiments described herein. Useful polymers of intrinsic microporosity and methods of making polymers of intrinsic microporosity are described in U.S. Pat. Nos. 7,690,514 and 8,056,732, which are hereby incorporated by reference. Useful polymers of intrinsic microporosity and methods of making polymers of intrinsic microporosity are also described in PCT International Patent Publications WO 2005/012397 and WO 2005/113121, which are hereby incorporated by reference. Useful polymers of intrinsic microporosity, the properties of polymers of intrinsic microporosity, and methods of making polymers of intrinsic microporosity are described in the review article by Neil B. McKeown entitled "Polymers of Intrinsic Microporosity" (ISRN Materials Science, Volume 2012, Article ID 513986), which is hereby incorporated by reference.

In some embodiments, polymers of intrinsic microporosity may be characterized by a surface area. In some embodiments, polymers of intrinsic microporosity may be characterized by gas adsorption/desorption amount and rates, such as for $N_2$ adsorption/desorption, which may allow for determination of their surface area, for example. Adsorption isotherms may be determined to allow for determination of a Brunauer, Emmett, and Teller (BET) surface area. BET surface areas may allow for comparison of microporosity characters, for example, between different polymers of intrinsic microporosity. For example, a first polymer of intrinsic microporosity that exhibits a smaller BET surface area than a second polymer of intrinsic microporosity may be characterized as having less microporosity than the second polymer of intrinsic microporosity. Useful unmodified and modified polymers of intrinsic microporosity include, but are not limited to, those exhibiting a surface area of at least 300 $m^2/g$, such as a surface area selected from the range of 200 $m^2/g$ to 1000 $m^2/g$, or from the range of 250 $m^2/g$ to 800 $m^2/g$.

In some embodiments, polymers of intrinsic microporosity may be characterized by their pore size. In some embodiments, polymers of intrinsic microporosity may be characterized by microporosity. Microporosity and pore sizes of polymers of intrinsic microporosity may be characterized by determining the effective rate of diffusion of one or more gases across a film of the polymer having a known thickness. Microporosity and pore size characteristics of polymers of intrinsic microporosity may be probed using positron annihilation lifetime spectroscopy, in some embodiments.

In some embodiments, polymers of intrinsic microporosity may be characterized by their solubility in organic solvents, such as tetrahydrofuran or chloroform. In some embodiments, polymers of intrinsic microporosity may exhibit high solubility in organic solvents, while other polymers may exhibit low or no solubility in organic solvents.

In some embodiments, polymers of intrinsic microporosity may be characterized by their molecular weights. Optionally, size exclusion chromatography may be useful for determining molecular weights of polymers of intrinsic microporosity. Optionally, gel permeation chromatography may be useful for determining molecular weights of polymers of intrinsic microporosity. Molecular weight determination may, in turn, allow for determination of a degree of polymerization of a polymer of intrinsic microporosity. Example polymers of intrinsic microporosity include, but are not limited to, those exhibiting molecular weights of at least 50 kg/mol, at least 100 kg/mol, at least 200 kg/mol, or at least 300 kg/mol. In some embodiments, polymers of intrinsic microporosity exhibit molecular weights selected from the range of about 50 kg/mol to about 250 kg/mol, or from the range of about 80 kg/mol to about 200 kg/mol. Example polymers of intrinsic microporosity include, but are not limited to, those exhibiting degrees of polymerization selected from the range of 100 to 1000, from the range of 200 to 900, from the range of 300 to 800, from the range of 400 to 700, or from the range of 500 to 600.

Figure 19B:
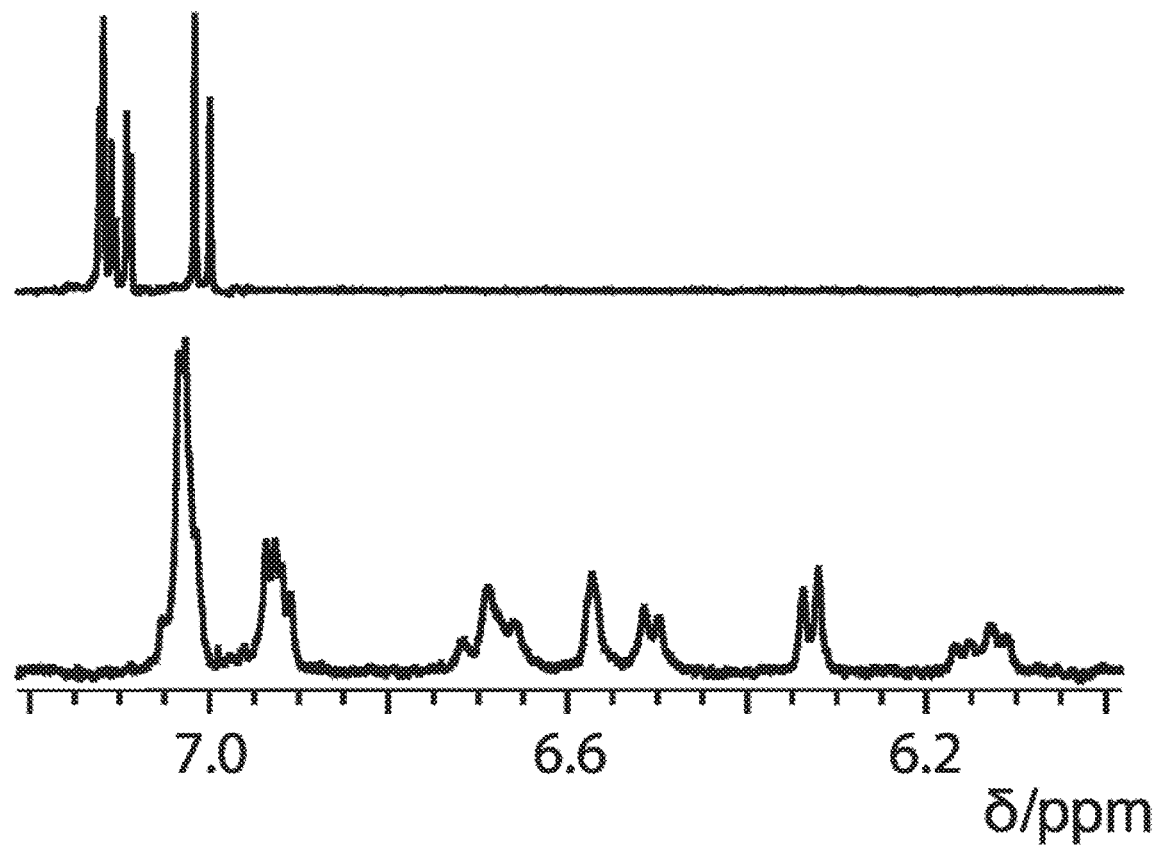
FIG. 19B provides data showing a portion of observed NMR spectra.
Figure 19C:
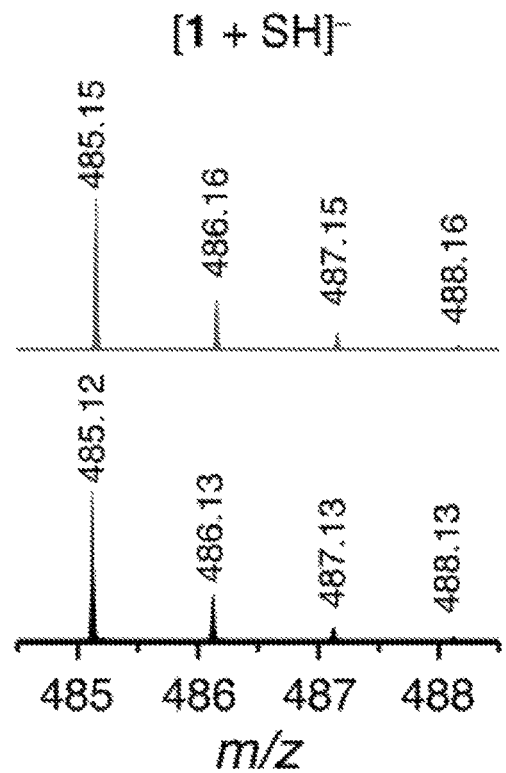
FIG. 19C provides data showing a portion of observed and calculated mass spectra.
Figure 19D:
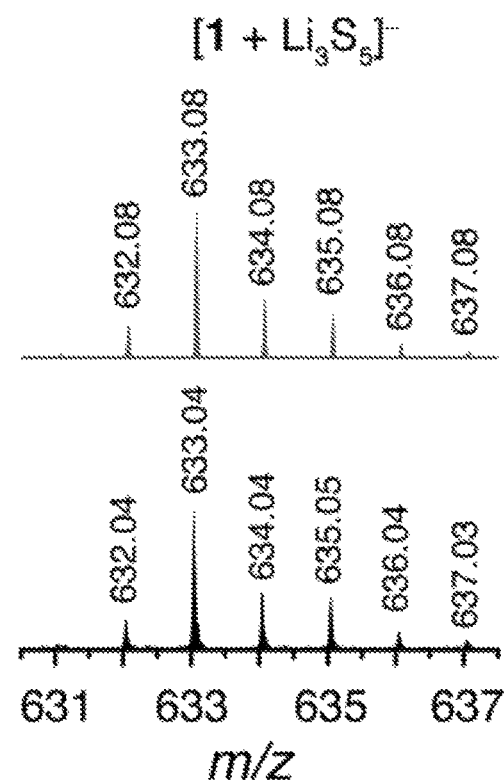
FIG. 19D provides data showing a portion of observed and calculated mass spectra.
Figure 20A:
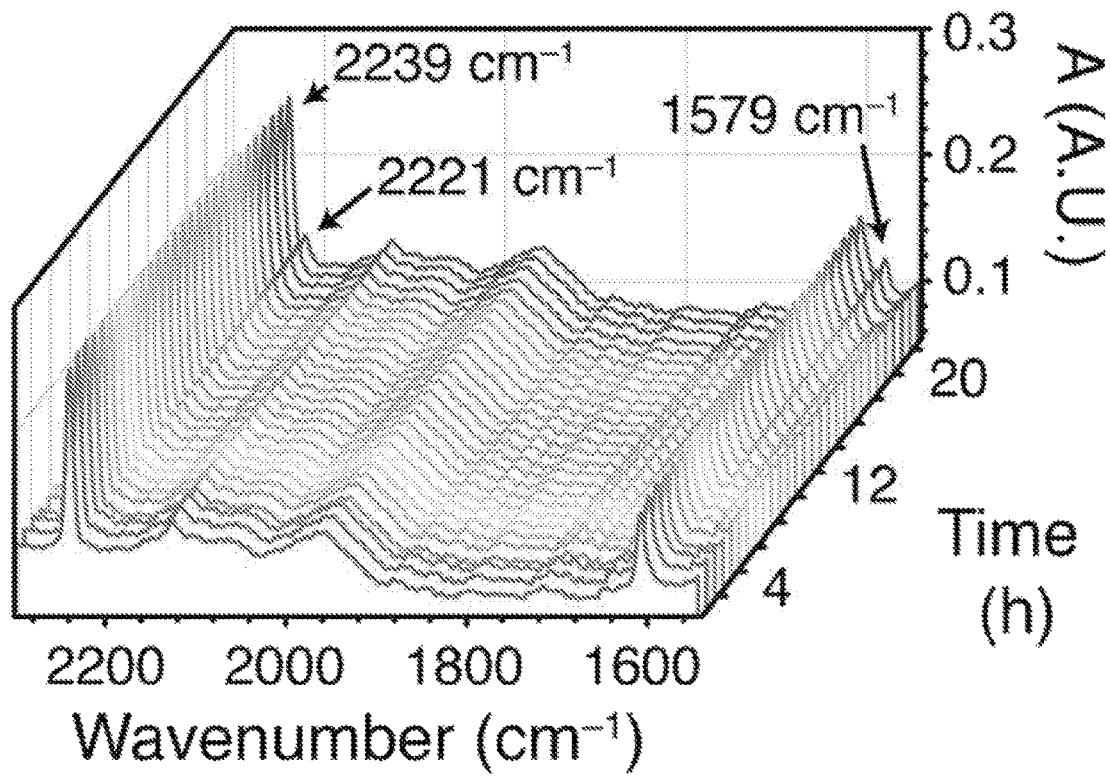
FIG. 20A provides data showing the time evolution of Fourier Transform infrared spectra during modification of a polymer of intrinsic microporosity.

Chemical structure characterization of polymers of intrinsic microporosity may be accomplished using a variety of techniques. Such characterizations may also allow for determination of modifications and degrees of modifications to polymers of intrinsic microporosity. For example, $^1$H and $^{13}$C nuclear magnetic resonance (NMR) spectroscopy may be useful. Example NMR spectra of embodiments of polymers of intrinsic microporosity are depicted in FIGS. 19B, 22B, 22C, 23A-23B, and 25. In some embodiments, infrared spectroscopy may also be useful. Example infrared spectra of embodiments of polymers of intrinsic microporosity are depicted in FIGS. 20A and 27. Additionally or alternatively, ionization mass spectrometry, such as electrospray ionization mass spectrometry, may also be useful for identifying structural moieties within a polymer of intrinsic microporosity. Example mass spectra of embodiments of polymers of intrinsic microporosity are depicted in FIGS. 19C-19D, 25, and 26.

Other characterization techniques known to the skilled artisan may be useful for characterizing unmodified polymers of intrinsic microporosity and modified polymers of intrinsic microporosity. For example, in some embodiments, polymers of intrinsic microporosity may be characterized by their ultraviolet and/or visible absorption spectra. As another example, a modified polymer of intrinsic microporosity may be characterized by an extent, density, or degree of crosslinking, such as by use of known standard techniques that evaluate how much a crosslinked polymer swells in a particular solvent at a particular temperature. Example standards include ASTM D2765 and ASTM F2214.

Useful polymers of intrinsic microporosity may be formed through polymerization reactions of suitable monomers or monomer sub-portions. For example, in some embodiments, a polymer of intrinsic microporosity is formed via a step-growth polymerization reaction. The following provides an illustration of a polymerization reaction for forming a polymer of intrinsic microporosity of one embodiment:

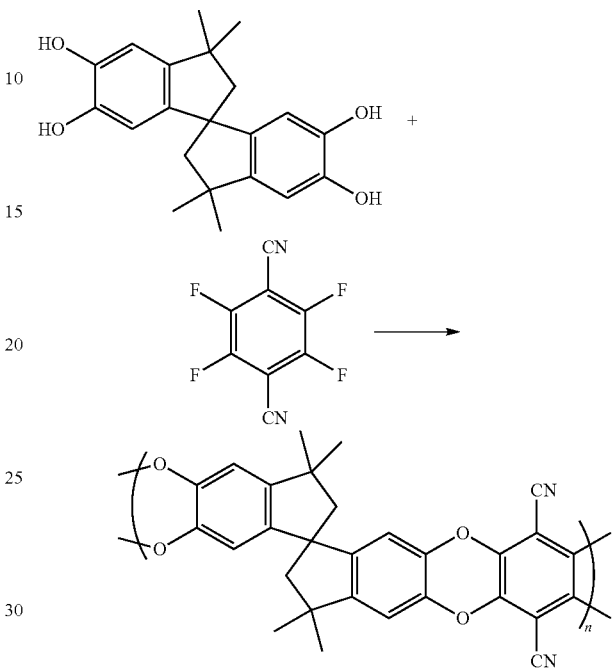

In some embodiments, the present invention provides modified polymers of intrinsic microporosity. For example, in some embodiments, a modified polymer of intrinsic microporosity comprises a polymer of intrinsic microporosity that includes a plurality of repeat units, as described above.

Modifications to polymers of intrinsic microporosity may include reduction of one or more repeat units to generate a negative charge within the repeat unit. Thus, in some embodiments, at least one of the repeat units in a modified polymer of intrinsic microporosity includes one or more negative charges. Optionally, at least one of the repeat units includes a negatively charged nitrogen site, a negatively charged oxygen site, a negatively charged sulfur site, a negatively charged carbon site, or any combination thereof. The chemical identity and position of such negatively charged sites may be determined by the specific nucleophilic reaction that takes place to provide the negative charge to the repeat unit.

Figure 1B:
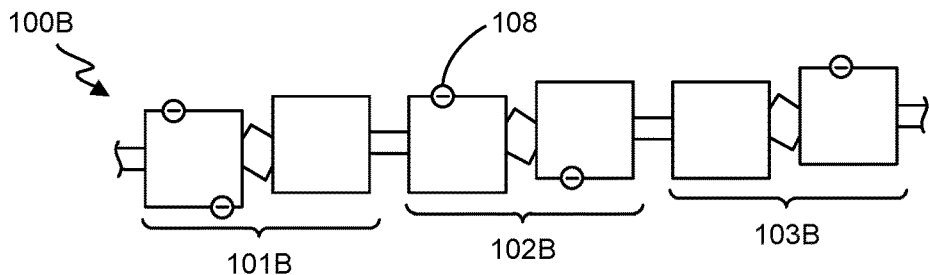
FIG. 1B, FIG. 1C, and FIG. 1D provide a schematic illustrations of modified polymers of intrinsic microporosity in accordance with some embodiments.

FIG. 1B provides a schematic illustration of an embodiment of a modified polymer of intrinsic microporosity 100B. Similar to FIG. 1A, the modified polymer of intrinsic microporosity 100B includes a plurality of repeat units 101B, 102B, and 103B linked by non-rotatable bonds and optionally including a non-rotatable linker between different repeat unit portions. Here, the modified polymer of intrinsic microporosity 100B is depicted as including a plurality of negative charges 108. Such negative charges may be formed by chemical reduction of portions of the repeat units. As illustrated, repeat unit 101B includes two negative charges, repeat unit 102B includes two negative charges, and repeat unit 103B includes one negative charge. It will be appreciated that each repeat unit may include more or fewer negative charges, as may be introduced through the chemical reduction process. It will further be appreciated that positive counter ions may be present and or coordinated with the negative charge. For simplicity, any positive counter ions are not illustrated.

In some embodiments, at least one repeat unit in a modified polymer of intrinsic microporosity includes a charged moiety selected from the group consisting of:

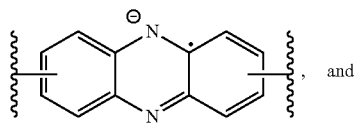, and

-continued

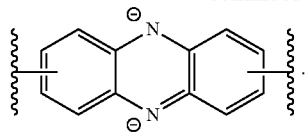.

Optionally, at least one of the repeat units in a modified polymer of intrinsic microporosity has a structure selected from the group consisting of:

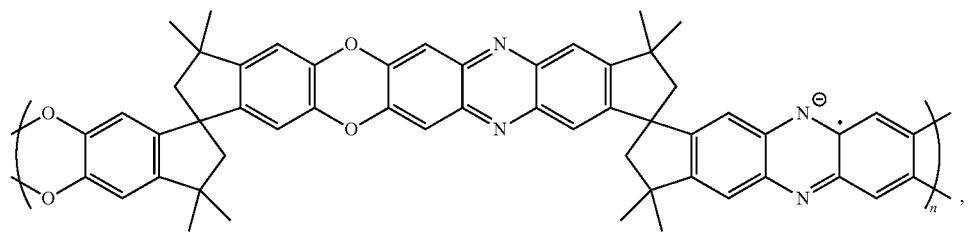,

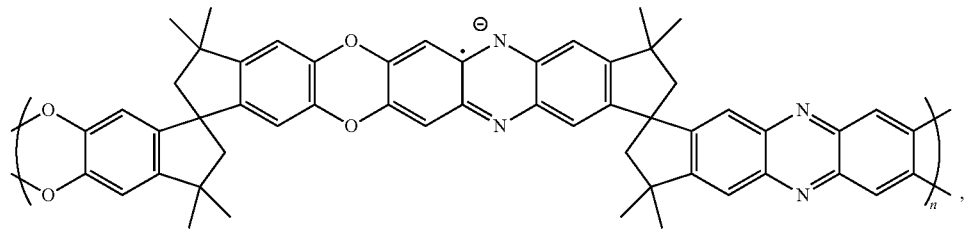,

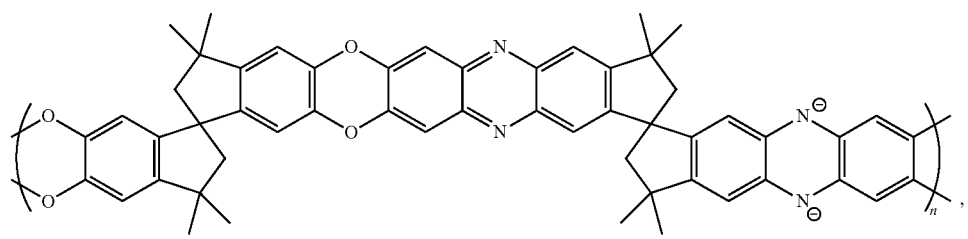,

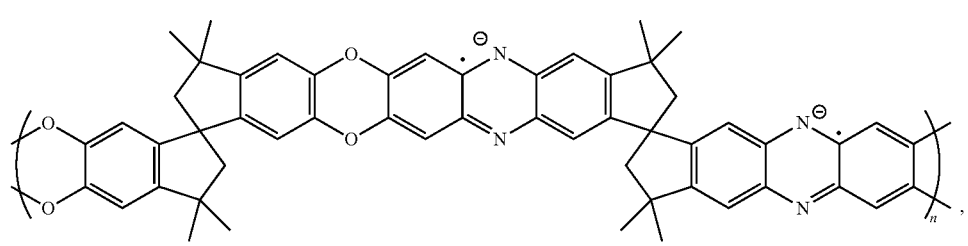,

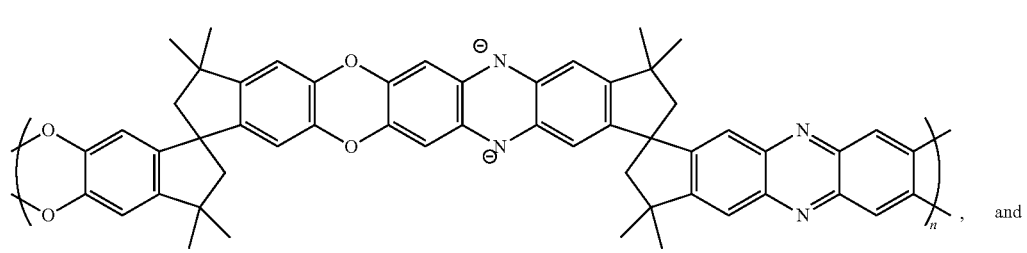, and

-continued

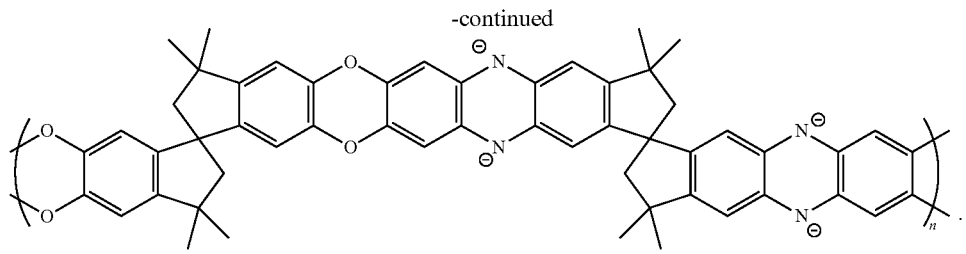

Modifications to polymers of intrinsic microporosity may alternatively or additionally include reaction of one or more repeat units with a nucleophile to generate a negative charge within the repeat unit. Accordingly, in some embodiments, at least one of the repeat units in a modified polymer of intrinsic microporosity includes one or more negative charges. Optionally, at least one of the repeat units includes a negatively charged nitrogen site, a negatively charged oxygen site, a negatively charged sulfur site, a negatively charged carbon site, or any combination thereof. The chemical identity and position of such negatively charged sites may be determined by the specific nucleophilic reaction that takes place to provide the negative charge to the repeat unit.

Figure 1C:
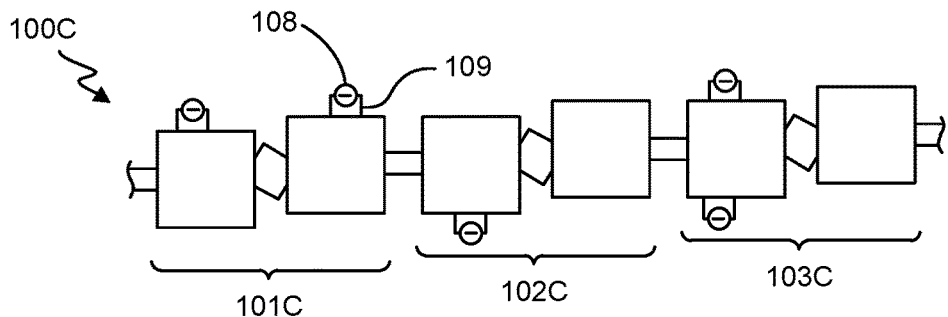

FIG. 1C provides a schematic illustration of an embodiment of a modified polymer of intrinsic microporosity 100C. Similar to FIGS. 1A-1B, the modified polymer of intrinsic microporosity 100C includes a plurality of repeat units 101C, 102C, and 103C linked by non-rotatable bonds and optionally including a non-rotatable linker between different repeat unit portions. Here, the modified polymer of intrinsic microporosity 100C is depicted as including a plurality of negative charges 108. Such negative charges may be formed by chemical reaction of portions of the repeat units with a nucleophile, such as a nucleophilic addition reaction. In a nucleophilic addition reaction, a portion of a nucleophile may be incorporated into the polymer of intrinsic microporosity, illustrated in FIG. 1C as charged moiety 109. As illustrated, repeat unit 101C includes two negative charges, repeat unit 102C includes one negative charge, and repeat unit 103C includes two negative charges. It will be appreciated that each repeat unit may include more or fewer negative charges, as may be introduced through the chemical nucleophilic reaction process. It will further be appreciated that positive counter ions may be present and or coordinated with the negative charge. Again, for simplicity, any positive counter ions are not illustrated.

In some embodiments, at least one repeat unit in a modified polymer of intrinsic microporosity includes a charged moiety selected from the group consisting of:

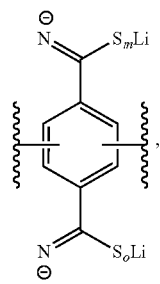

where subscript m is an integer selected from 1 to 8, or where subscript m and subscript o are independently integers selected from 1 to 8. Optionally, at least one of the repeat units in a modified polymer of intrinsic microporosity has a structure selected from the group consisting of:

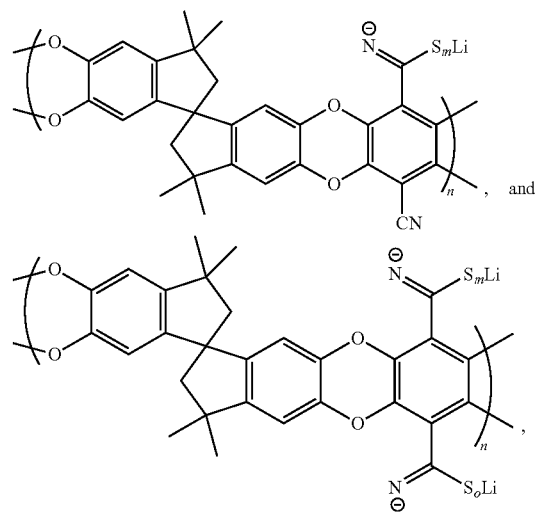

where subscript m and subscript o are independently integers selected from 1 to 8.

Modifications to polymers of intrinsic microporosity may alternatively or additionally include crosslinking of the repeat units. For example, in some embodiments, at least one repeat unit is crosslinked with a non-adjacent repeat unit, such as a repeat unit of a different polymer chain. Crosslinking may be achieved by exposure of a polymer of intrinsic microporosity to a crosslinking agent. Crosslinking agents may include heating the polymer of intrinsic microporosity or exposing the polymer of intrinsic microporosity to ultraviolet and/or microwave radiation. Crosslinking agents may alternatively or additionally include compounds that may react with multiple repeat units or may facilitate reaction between repeat units. It will be appreciated that, because adjacent repeat units are already covalently bonded to one another, such as through a non-rotatable bond, crosslinking may refer to the creation of covalent links between non-adjacent repeat units.

Figure 1D:
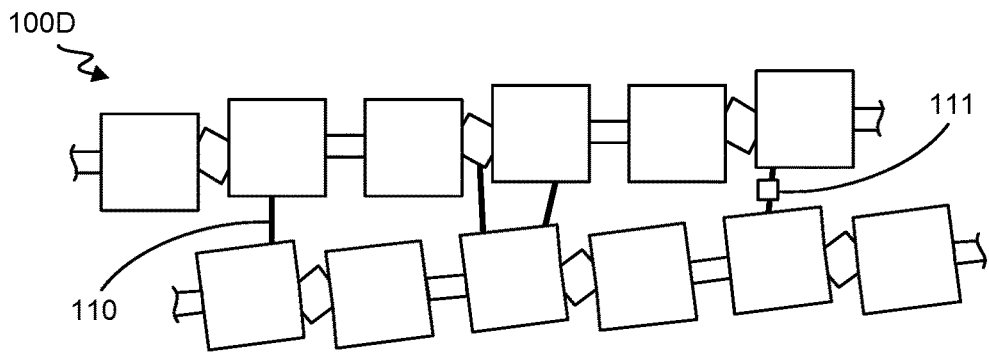

FIG. 1D provides a schematic illustration of an embodiment of a modified polymer of intrinsic microporosity 100D. In FIG. 1D, two polymer segments are illustrated, which may belong to the same polymer molecule or different polymer molecules. A plurality of covalent bonds 110 are illustrated as bonding between non-adjacent repeat units. In FIG. 1D, a covalent crosslinking moiety 111 is illustrated as linking non-adjacent repeat units. It will be appreciated that FIG. 1D is to be interpreted as not limiting the number and location of crosslinks in a modified polymer of intrinsic microporosity, which may be between repeat unit portions, or between a non-rotatable linker and a repeat unit portion, or between non-rotatable linkers, for example.

Optionally, at least one repeat unit is crosslinked with a non-adjacent repeat unit by a crosslinker selected from the group consisting of 2,6-bis(4-azidobenzylidene)cyclohexanone, 2,6-bis(4-azidobenzylidene)-4-methylcyclohexanone, 2,6-bis(4-azidobenzylidene)-4-ethylcyclohexanone, 4-azidophenylsulfone, and any combination of these.

In some embodiments, methods of making modified polymers of intrinsic microporosity are provided. In one embodiment, a method of making a modified polymer of intrinsic microporosity comprises forming a reaction mixture comprising a polymer of intrinsic microporosity and a reducing agent, or a nucleophile, or a crosslinking agent, or any combination thereof under conditions sufficient to form the modified polymer of intrinsic microporosity. In some embodiments, the modified polymer of intrinsic microporosity comprises a plurality of repeat units and at least one of the repeat units includes one or more negative charges, or wherein the modified polymer of intrinsic microporosity is crosslinked, or both.

Figure 2:
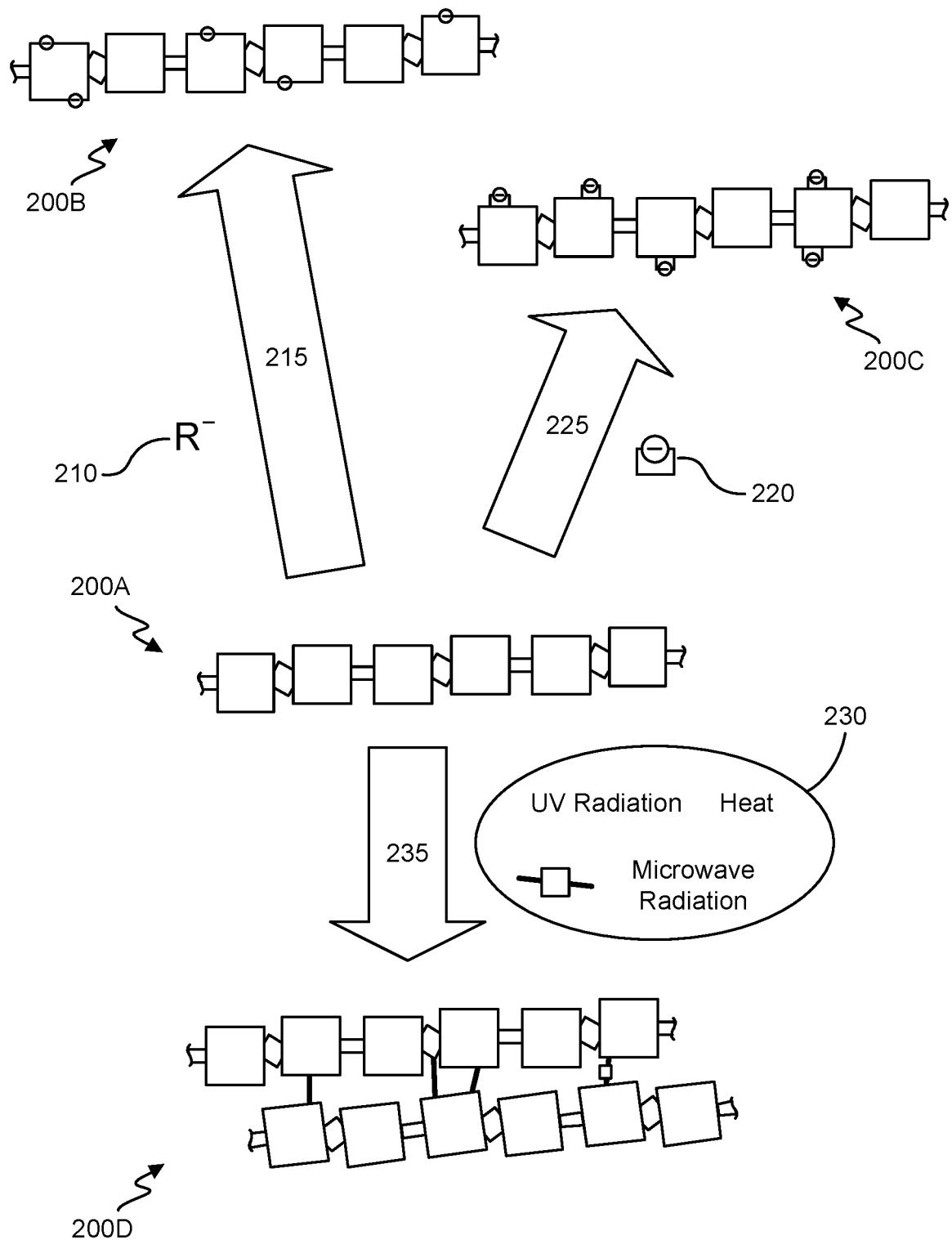
FIG. 2 provides details of methods of making modified polymers of intrinsic microporosity in accordance with some embodiments.

FIG. 2 provides an overview of some method embodiments for making modified polymers of intrinsic microporosity. A reaction mixture comprising a polymer of intrinsic microporosity 200A is formed. The reaction mixture may further include one or more of a reducing agent 210, a nucleophile 220, or a crosslinking agent 230. Reaction between the polymer of intrinsic microporosity 200A and the reducing agent 210 or the nucleophile 220 may generate one or more negative charges in at least one of the repeat units.

When a mixture of a polymer of intrinsic microporosity 200A and reducing agent 210 is formed, reaction 215 may occur to form modified polymer of intrinsic microporosity 200B that includes negative charges incorporated into one or more of the repeat units. When a mixture of a polymer of intrinsic microporosity 200A and nucleophile 220 is formed, reaction 225 may occur to form modified polymer of intrinsic microporosity 200C that includes negative charges incorporated into one or more of the repeat units.

Useful reducing agents include, but are not limited to an alkali metal polysulfide, such as $Li_2S_m$, where subscript m is an integer selected from 2 to 100, an alkali metal sulfide, such as $Li_2S$, ammonium sulfide, an alkali metal hydrogen sulfide, such as LiSH, an alkali metal, a metallocene, such as $(C_5Me_5)_2Fe$ or $(C_5Me_5)_2Ni$, an alkali metal naphthalenide, such as $NaC_{10}H_8$ or $LiC_{10}H_8$, an inorganic reducing agent having an oxidation potential at or below 0.0 V vs. a standard hydrogen electrode (SHE), an organic reducing agent having an oxidation potential at or below 0.0 V vs. SHE, and any combination of these.

Useful nucleophiles include, but are not limited to, an alkali metal polysulfide, $Li_2S_m$ where subscript m is an integer selected from 2 to 100, an alkali metal sulfide, ammonium sulfide, an alkali metal hydrogen sulfide, an alkali metal alkylsulfide, an alkali metal arylsulfide, $P_2S_5$, an alkali metal sulfite, and any combination of these.

Any suitable solvent can be used in the methods of the present invention. Representative solvents include, but are not limited to, glyme or dimethoxymethane based solvents, such as diglyme (G2), triglyme (G3), and tetraglyme (G4), pentane, pentanes, hexane, hexanes, heptane, heptanes, petroleum ether, cyclopentanes, cyclohexanes, benzene, toluene, xylene, trifluoromethylbenzene, halobenzenes such as chlorobenzene, fluorobenzene, dichlorobenzene and difluorobenzene, methylene chloride, chloroform, or combinations thereof. In some embodiments, the solvent can be pentanes, hexanes, heptanes, cyclopentanes, cyclohexanes, benzene, toluene, xylene, trifluoromethylbenzene, chlorobenzene, or combinations thereof. In some embodiments, the solvent can be pentanes, hexanes, heptanes, cyclopentanes, cyclohexanes, or combinations thereof. In some embodiments, the solvent can be pentanes, hexanes, heptanes, or combinations thereof. In some embodiments, the solvent can be heptanes. In some embodiments, the solvent can be toluene. In some embodiments, the reaction mixture can be a heterogeneous reaction mixture. In some embodiments, the reaction mixture can be a suspension.

The reaction mixture of the method can be at any suitable temperature. For example, the temperature of the reaction mixture can be of from about −78° C. to about 100° C., or of from about −50° C. to about 100° C., or of from about −25° C. to about 50° C., or of from about −10° C. to about 25° C., or of from about 0° C. to about 20° C. In some embodiments, the temperature of the reaction mixture can be of from about −25° C. to about 50° C. In some embodiments, the temperature of the reaction mixture can be of from about −10° C. to about 25° C. In some embodiments, the temperature of the reaction mixture can be of from about 0° C. to about 20° C.

The reaction mixture of the method can be at any suitable pressure. For example, the reaction mixture can be at atmospheric pressure. The reaction mixture can be also be exposed to any suitable environment, such as atmospheric gases, or inert gases such as nitrogen or argon.

When a mixture of a polymer of intrinsic microporosity 200A and crosslinking agent 230 is formed, crosslinking reaction 235 may occur to form modified polymer of intrinsic microporosity 200D that includes one or more crosslinks between non-adjacent repeat units. For example, in an embodiment, reaction between the polymer of intrinsic microporosity and the crosslinking agent induces crosslinking of the polymer of intrinsic microporosity by generating one or more covalent bonds between a first repeat unit and a second repeat unit that is not adjacent to the first repeat unit Useful crosslinking agents include, but are not limited to, 2,6-bis(4-azidobenzylidene)cyclohexanone, 2,6-bis(4-azidobenzylidene)-4-methylcyclohexanone, 2,6-bis(4-azidobenzylidene)-4-ethylcyclohexanone, 4-azidophenylsulfone, oxygen, and any combination of these.

Optionally, forming a reaction mixture comprising a polymer of intrinsic microporosity and a crosslinking agent comprises inducing a crosslinking reaction of the polymer of intrinsic microporosity by exposure of the polymer of intrinsic microporosity to one or more of ultraviolet radiation, microwave radiation, and heat.

Optionally, polymers of intrinsic microporosity and modified polymers of intrinsic microporosity may be formed into membranes. For example, the polymers may be cast into a membrane comprising a web or sheet of the polymer material. Optionally, a membrane comprising a polymer of intrinsic microporosity or a modified polymer of intrinsic microporosity may comprise a support membrane. In some embodiments, the polymer of intrinsic microporosity or a modified polymer of intrinsic microporosity may be cast to, coated on, and/or encapsulate the support membrane. Use of a support membrane may be beneficial, in some embodiments, when the polymer of intrinsic microporosity or the modified polymer of intrinsic microporosity does not possess sufficient strength to form a free-standing film or if additional strength or features are desired in a membrane. For example, use of a polymeric support membrane may be useful for imparting a membrane with mechanical strength or to provide particular thermal characteristics to the membrane. Such properties may be useful for electrochemical cells and ion separation systems comprising a polymer of intrinsic microporosity or a modified polymer of intrinsic microporosity.

In some embodiments, the present invention provides modified polymers of intrinsic microporosity prepared by reacting a polymer of intrinsic microporosity with a reducing agent, a nucleophile, a crosslinking agent, or any combination of these. Optionally, reacting a polymer of intrinsic microporosity with a reducing agent, a nucleophile, and/or a crosslinking agent includes forming a reaction mixture of the polymer of intrinsic microporosity and the reducing agent, the nucleophile, and/or the crosslinking agent under conditions sufficient to form the modified polymer of intrinsic microporosity. Sufficient conditions may include, but are not limited to, a temperature adequate for the reaction to proceed, such as a temperature of about 25° C., a pressure adequate for the reaction to proceed, such as a pressure of about atmospheric pressure, and adequate reactant ratios, such as a molar ratio of the polymer of intrinsic microporosity to the reducing agent, the nucleophile, and/or the crosslinking agent selected from the range of about 100:1 to about 1:100, for example.

In some embodiments, the present invention provides films comprising modified polymers of intrinsic microporosity prepared by forming a film of a polymer of intrinsic microporosity and exposing the film to a reducing agent, a nucleophile, and/or a crosslinking agent. It will be appreciated that films may be formed using any techniques, such as a drop casting technique or a dip coating technique. In an embodiment, a film comprising a modified polymer of intrinsic microporosity is prepared by generating a mixture by dissolving the polymer of instrinsic microporosity in a solvent, placing the mixture onto a surface, evaporating the solvent present in the mixture to form the film, and exposing the film to film to a reducing agent, a nucleophile, and/or a crosslinking agent. Optionally, the surface may be a polymer support structure, such as a porous polymer support.

Optionally, a modified polymer of intrinsic microporosity is prepared by reacting a polymer of intrinsic microporosity with a nucleophile and/or a reducing agent and then crosslinking the modified polymer of intrinsic microporosity. Optionally, a modified polymer of intrinsic microporosity is prepared by crosslinking the polymer of intrinsic microporosity and then reacting the crosslinked polymer of intrinsic microporosity with a nucleophile and/or a reducing agent. Crosslinking methods useful for preparing modified polymers of intrinsic microporosity include exposing a polymer of intrinsic microporosity or a modified polymer of intrinsic microporosity to ultraviolet, exposing a polymer of intrinsic microporosity or a modified polymer of intrinsic microporosity to microwave radiation, and/or heating a polymer of intrinsic microporosity or a modified polymer of intrinsic microporosity.

IV. Electrochemical Cells

In some embodiments, electrochemical cells are provided herein. Electrochemical cells of some embodiments may comprise a polymer of intrinsic microporosity or a modified polymer of intrinsic microporosity, such as described above. In a specific embodiment, for example, an electrochemical cell comprises an anode, an anode electrolyte in contact with the anode, a separator in contact with the anode electrolyte, such as a separator that comprises a polymer of intrinsic microporosity, a cathode electrolyte in contact with the separator, and a cathode in contact with the cathode electrolyte. Optionally, the polymer of intrinsic microporosity comprises a modified polymer of intrinsic microporosity, such as described above.

Figure 3:
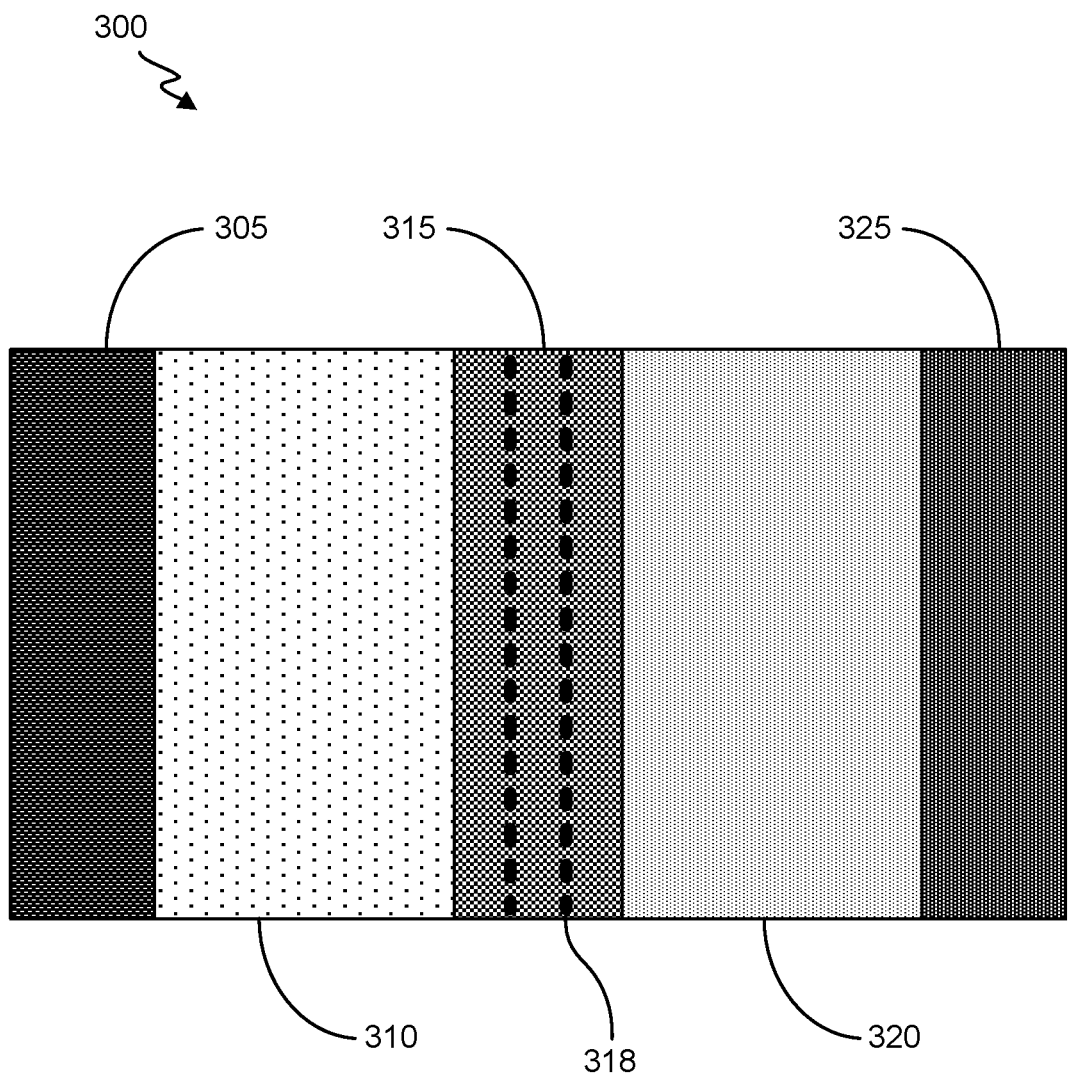
FIG. 3 provides a schematic illustration of an electrochemical cell in accordance with some embodiments.

FIG. 3 provides a schematic illustration of an electrochemical cell 300 embodiment. Electrochemical cell 300 comprises an anode 305, an anode electrolyte 310, a separator 315, a cathode electrolyte 320 and a cathode 325. As a specific example, electrochemical cell 300 may comprise a lithium-sulfur battery, where anode 305 comprises lithium and cathode 325 comprises sulfur.

It will be appreciated that, while anode 305 is illustrated as an explicit body of material, in some embodiments, anode 305 may be included within anode electrolyte 310, such as a dissolved component within anode electrolyte 310, as may be the configuration in a flow battery. It will also be further appreciated that, while cathode 325 is illustrated as an explicit body of material, in some embodiments, anode 325 may be included within cathode electrolyte 320, such as a dissolved component within cathode electrolyte 320, as may be the configuration in a flow battery.

Optionally, the separator 315 comprises a support membrane 318 in contact with the polymer of intrinsic microporosity, such as described above. Useful support membranes include those comprising a polymer selected from the group consisting of: polyethylene, polyethylene copolymers, polypropylene, polypropylene copolymers, polyacrylonitrile, polyacrylonitrile copolymers, poly(vinylidene fluoride), poly(tetrafluoroethylene), poly(vinyl chloride), poly(vinylchloride) copolymers, poly(hexafluoropropylene), poly(hexafluoropropylene) copolymers, polyaramide, any combination thereof, and any copolymers thereof.

As illustrated in FIG. 3, separator 315 includes two support membrane 318. While two support membranes are illustrated in FIG. 3, it will be appreciated that any number of support membranes are useful with electrochemical cells of some embodiments. Alternatively, some separators may not include any support membrane. Support membrane 318 may comprise a porous polymer film, which may allow ions to pass through unimpeded. Optionally, electrochemical cell may include one or more current collectors, such as a first current collector in contact with anode 305 and/or anode electrolyte 310, and/or a second current collector in contact with cathode electrolyte 320 and/or cathode 325.

In some embodiments, the support membrane 318 has a melting temperature, and exposing the support membrane 318 to a temperature exceeding the melting temperature causes at least a portion of the support membrane 318 to melt and close pores within the separator. For example, the melting temperature may be selected from the range of 100° C. to 180° C.

Use of a support membrane that may advantageously provide important safety features to electrochemical cells incorporating such. For example, a support membrane may provide additional strength to the separator beyond that provided by the polymer of intrinsic microporosity or modified polymer of intrinsic microporosity comprising the separator. Such strength may be important for blocking dendrites that may form on the anode, for example, from puncturing the separator and contacting the cathode. Such a condition may result in overheating or thermal runaway of an electrochemical cell and potentially ignite the electrolyte or enclosure components.

Additionally or alternatively, a support membrane that may melt during heating caused by damage to a separator, thermal runaway, and/or overheating may advantageously stop the thermal runaway and/or overheating. For example, melting of at least a portion of the support membrane may result in pores in the separator closing, which may stop any discharge of the electrochemical cell. Additionally, melting of at least a portion of the support membrane may coat a dendrite that has damaged the separator, preventing the dendrite from making contact with the cathode, for example.

V. Selective Ion Transport Techniques and Ion Separation Systems

Figure 4A:
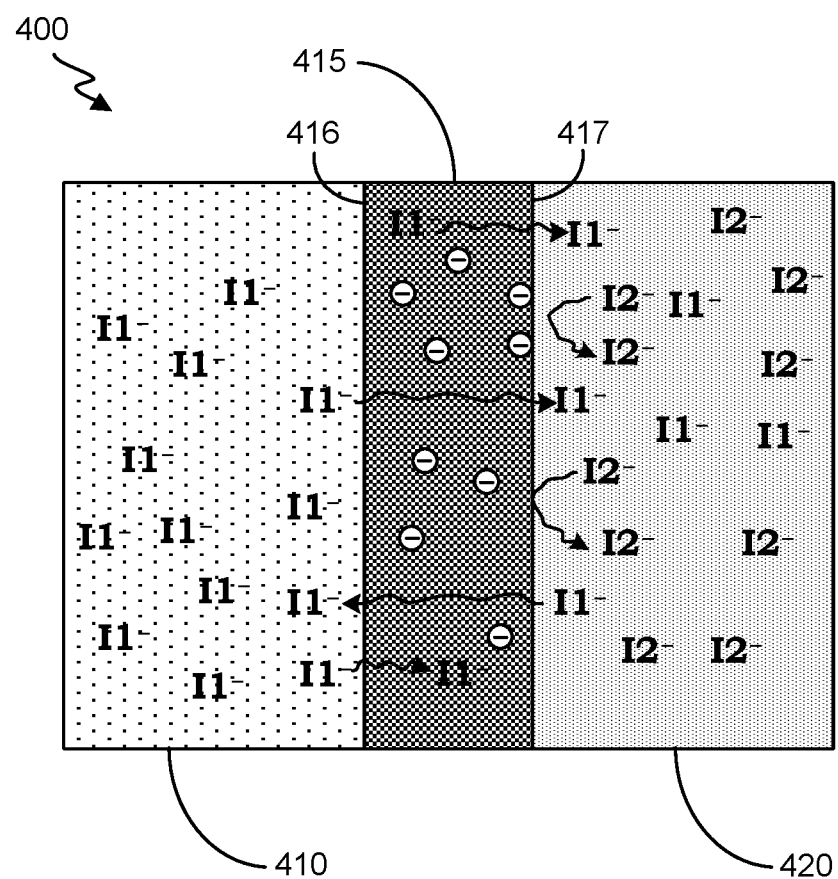
FIG. 4A provides a schematic illustration of a system embodiment for use in a method of selective ion transport.
Figure 4B:
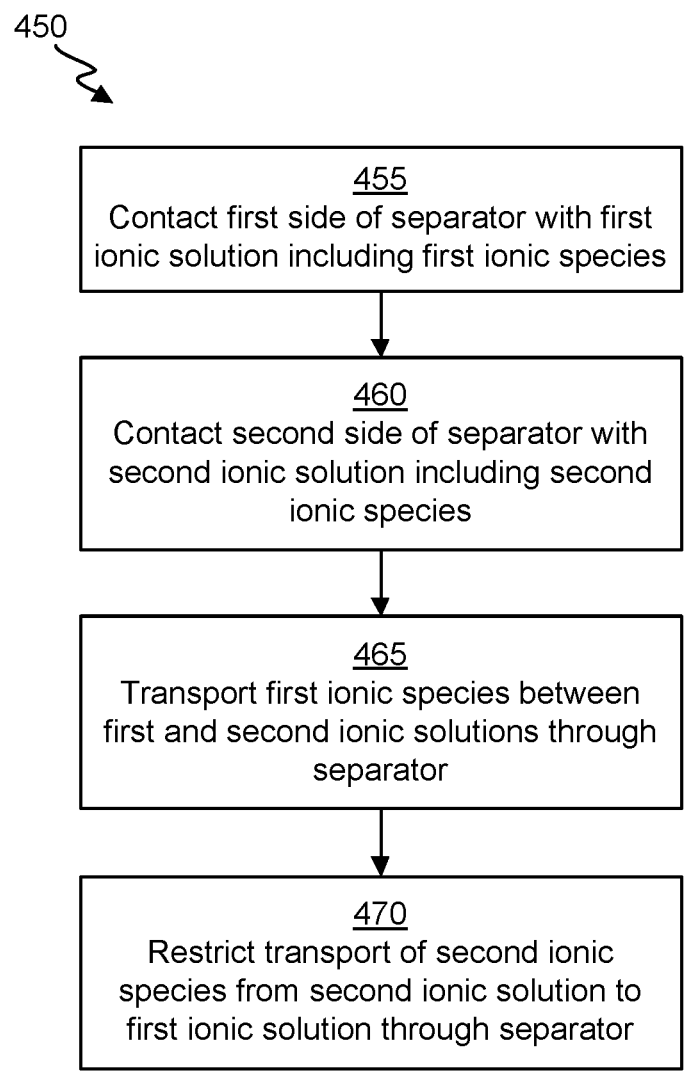
FIG. 4B provides an overview of a method embodiment for selective ion transport.

In some embodiments, ion separation systems and methods of selective ion transport are provided herein. Ion separation systems of some embodiments may comprise a polymer of intrinsic microporosity or a modified polymer of intrinsic microporosity, such as described above. An example ion separation system 400 is depicted in FIG. 4A. Ion separation system 400 comprises a first ionic solution 410 comprising a first ionic species (I1$^-$), a separator 415 in contact with the first ionic solution, such as a separator comprising a polymer of intrinsic microporosity and/or a modified polymer of intrinsic microporosity, and a second ionic solution 420 in contact with the separator, such as a second ionic solution that includes a second ionic species (I2$^-$). As illustrated a first side 416 of the separator 415 is in contact with first ionic solution 410 and a second side 417 of the separator 415 is in contact with second ionic solution 420. The separator 415 may be selectively permeable to the first ionic species such that the first ionic species may transport between the first ionic solution 410 and the second ionic solution 420 through micropores of the separator. The separator 415 may restrict the second ionic species from passing through the separator 415 to reach the first ionic solution. For example, the micropores of the separator 415 may have a cross sectional dimension that provides size sieving and restriction of the second ionic species from being transported through the separator. In separators including a modified polymer of intrinsic microporosity that include negatively charged sites, the negative charges may further provide an electrostatic restriction on the second ionic species from being transported through the separator.

Systems and methods of some embodiments may be useful for restricting ions of a particular size and/or a particular size and charge combination to a particular region. For example, it may be desirable to limit the passage of polysulfide ions from a cathode electrolyte in an electrochemical cell to the anode electrolyte in the electrochemical cell. The systems and methods of some embodiments may advantageously facilitate this limitation, such as by preventing the polysulfide ions from passing through a separator and/or by reducing a rate at which polysulfide ions pass through a separator.

In a specific embodiment, a method of selective ion transport comprises contacting a first side of a separator with a first ionic solution, such as a separator that comprises a polymer of intrinsic microporosity, wherein the first ionic solution comprises a first ionic species; contacting a second side of the separator with a second ionic solution, wherein the second ionic solution comprises a second ionic species; and transporting the first ionic species between the first ionic solution and the second ionic solution through the separator. In some embodiments, the separator provides a size selective restriction on transport of the second ionic species from the second ionic solution to the first ionic solution through the separator. Optionally, the separator further provides an electrostatic restriction on transport of the second ionic species from the second ionic solution to the first ionic solution through the separator.

VI. Examples

The invention may be further understood by reference to the following non-limiting examples.

Example 1. Polysulfide-Blocking Microporous Polymer Membrane Tailored for Hybrid Li-Sulfur Flow Batteries Redox flow batteries (RFBs) present unique opportunities for multi-hour electrochemical energy storage (EES) at low cost. Too often, the barrier for implementing them in large-scale EES is the unfettered migration of redox active species across the membrane, which shortens battery life and reduces Coulombic efficiency. To advance RFBs for reliable EES, a new paradigm for controlling membrane transport selectivity is needed. This Example shows that size- and ion-selective transport can be achieved using membranes fabricated from polymers of intrinsic microporosity (PIMs). For example, a first-generation PIM membrane dramatically reduced polysulfide crossover (and shuttling at the anode) in lithium-sulfur batteries, even when sulfur cathodes were prepared as flowable energy-dense fluids. The design of the membrane platform was informed by molecular dynamics simulations of the solvated structures of lithium bis(trifluoromethanesulfonyl)imide (LiTF SI) vs lithiated polysulfides ($Li_2S_x$, where x=8, 6, and 4) in glyme-based electrolytes of different oligomer length. These simulations suggested polymer films with pore dimensions less than 1.2-1.7 nm might incur the desired ion-selectivity. Indeed, the polysulfide blocking ability of the PIM-1 membrane (~0.8 nm pores) was improved 500-fold over mesoporous Celgard separators (~17 nm pores). As a result, significantly improved battery performance was demonstrated, even in the absence of $LiNO_3$ anode-protecting additives.

Membranes (or separators) are critical for ionic conduction and electronic isolation in many electrochemical devices. For cell architectures that utilize redox-active species that are dissolved, dispersed, or suspended in electrolyte, from fuel cells (FCs) to redox flow batteries (RFBs), it is also of value that the membrane prevent active material crossover that would otherwise contribute to device shorting, electrode fouling, or irrevocable loss in capacity. Unfortunately, commercial battery separators, which feature shape-persistent mesopores, are freely permeable to most active materials used in RFBs. Alternative membrane separators have thus far relied heavily on variants of aqueous single-ion conductors, e.g., Nafion, which may ultimately restrict the use of certain types of flowable electrodes. Considerably less attention has been paid to size-sieving as a mechanism to achieve membrane selectivity, although success in this regard would allow greater flexibility in battery chemistries. Despite the wide availability of porous materials that might serve effectively as membrane components, including zeolites, metal-organic frameworks, covalent organic frameworks, carbon nanotubes, cyclic peptide nanotubes, and microporous polymers, rational design rules for achieving ion-selective transport via sieving in flow battery membranes have not been established.

Guided by theoretical calculations, this example applies polymers of intrinsic microporosity (PIMs) as a membrane platform for achieving high-flux, ion-selective transport in nonaqueous electrolytes. These polymers are synthesized in a single step and easily cast into large-area sheets with well-controlled pore structure and pore chemistry (FIG. 5). The unique micropore architecture of PIMs arises primarily from two molecular characteristics: (1) PIMs do not feature rotating bonds along their backbone; and (2) they incorporate rigid sharp bends into at least one of the constituent monomers at regular intervals along the polymer chain. Both features contribute to frustrated packing of polymer chains in the solid state. As a result, PIMs are amorphous yet exhibit high intrinsic microporosity (<2 nm) and high surface area (300-1500 $m^2$ $g^{-1}$). The open pore architecture of PIMs suggests that they might be advantageously positioned for selective species transport in electrochemical devices via sieving.

This Example highlights new opportunities for PIMs to serve as ion-selective membranes in RFBs, using lithium-sulfur (Li—S) as a model battery chemistry. Here the lithium anode is stationary and separated, by the membrane, from the flowable sulfur-containing catholyte. This RFB features a high theoretical specific energy capacity of 1670 mAh $g^{-1}$ for S and operating voltage that exceeds 2.0 V. While these are desirable characteristics, this battery chemistry suffers from low Coulombic efficiency and rapid capacity fade when lithium polysulfides (PS) crossover to and react with the metal anode surface. Strategies seeking to mitigate PS crossover in Li—S batteries have included the use of sacrificial anode-protecting additives (e.g., $LiNO_3$), single-ion conducting membranes, conductive interlayers, permselective barriers, and even polysulfide adsorbates. Nonetheless, continuous Li consumption upon cycling remains a problem. This Example demonstrates that PIM membranes block PS crossover while allowing ions in the supporting electrolyte to traverse the membrane with minimal impedance and indicates a direct solution to the PS crossover problem is feasible. This Example also shows dramatically improved performance of batteries when PIM membranes are in place, rather than conventional battery separators.

To inform the rational design of a membrane platform capable of achieving high transport selectivity for supporting electrolyte (lithiumbis(trifluoromethane)sulfonimide, LiTFSI) vs PS in Li—S RFBs, molecular dynamics (MD) simulations were carried out for each species' solvated structures in different ethereal solvents, diglyme (G2), triglyme (G3), and tetraglyme (G4), as these are commonly used in Li—S RFBs. The simulated effective sizes of these solvated complexes were determined by the radii of gyration ($R_g$) of the solute and the first solvation shell. These shells were typically composed of two solvent molecules, as exemplified by the average snapshots shown in FIG. 6A. The size of elemental sulfur was calculated, which exhibits no explicit solvent coordination in the simulations. For this singular case, a size for $S_8$ was determined using its atoms' van der Waals solvent-excluded radii. The determinations of $R_g$ provide size-ranges for selective ion transport (FIG. 6B). As the primary contributors to the shuttling currents are lithium polysulfides, $Li_2S_x$ where x≥4, the membrane pore dimensions should be smaller than 1.2-1.7 nm in order to achieve ion-selective transport.

Figure 9:
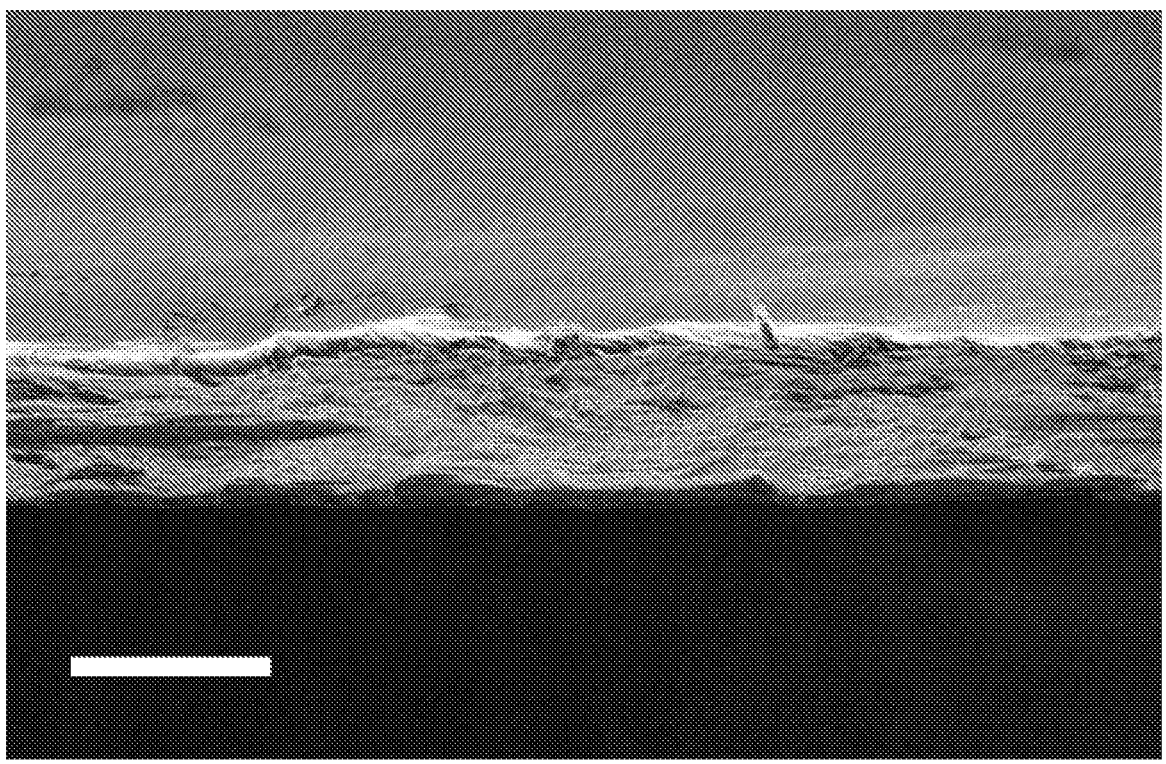
FIG. 9 provides a cross-sectional scanning electron micrograph image of a membrane comprising a polymer of intrinsic microporosity.

Directed by the MD simulations, PIM-1 30 was identified as a possible PS-blocking membrane material for Li—S hybrid flow cells. PIM-1 is the progenitor of a family of non-networked ladder polymers that are mechanically and thermally robust; pertinent to their use here, their pore dimensions are sub-nm. PIM-1 was synthesized (200 kg $mol^{-1}$) on a multigram scale from inexpensive, commercially available monomers and cast from solution into flexible free-standing membranes (~10 μm thick) (FIG. 5 and FIG. 9). The specific surface area (795 $m^2$ $g^{-1}$) and pore size distribution of PIM-1 was determined using nitrogen adsorption isotherms (FIG. 6C). PIM-1 membranes had a nominal pore size of 0.77 nm, which is useful for selective transport of LiTFSI and PS blocking. This stands in stark contrast with commercially available Celgard 2325, which has a much larger pore size of 17 nm: far too large for size-selective transport (FIG. 6C). Celgard 2325 and similar mesoporous polymer separators are commonly used in Li—S cells and serve as a useful benchmark for new membrane materials. A total porosity of ~25% was determined for PIM-1 membranes using ellipsometric porosimetry, which is comparable to the porosity of Celgard 2325. As PIM-1 membranes are expected to swell to a degree upon introduction of electrolyte, this determination should be considered a lower limit to the available free volume.

Figure 7A:
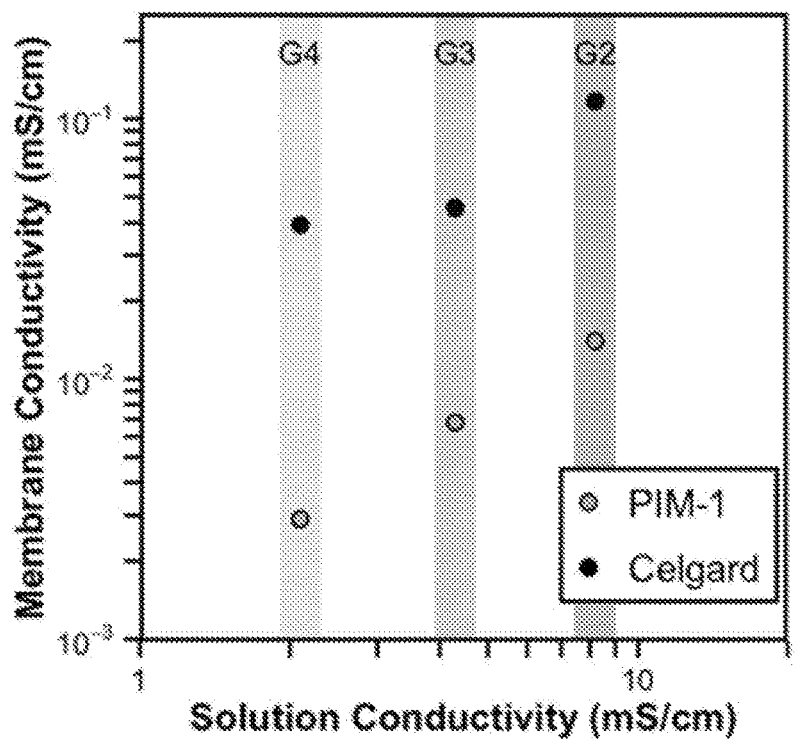
FIG. 7A provides data showing ambient temperature ionic conductivity for two materials.

It was hypothesized that during battery operation the free volume in PIM-1 (and PIMs generally) would become swollen and infiltrated with electrolyte, creating an ionically percolating solution-phase conductive network. As a result, ion flux would be solely carried by (and be dependent on) the solution conductivity within the pores; polymer chain dynamics, which are orders of magnitude slower, would no longer dictate the membrane's ionic conductivity. To test this hypothesis, PIM-1's membrane ionic conductivities were evaluated in glymes of different oligomer lengths, diglyme (G2), triglyme (G3), and tetraglyme (G4), containing 0.50 M LiTFSI. A strong correlation between the membrane ionic conductivity and the bulk solution ionic conductivity of the electrolyte was noted (FIG. 7A). These results indicate that the ion current is indeed carried by the infiltrating electrolyte, as predicted. This behavior was also observed in Celgard separators (FIG. 7A). By comparing the membrane ionic conductivities for Celgard and PIM-1, it was found that reducing the pore dimensions from 17 to 0.77 nm, respectively, only decreased membrane ionic conductivity 10-fold. It was also found that electrolytes based on diglyme provided the highest membrane ionic conductivity for both platforms and was thus chosen as the supporting electrolyte for all subsequent experiments.

Figure 7B:
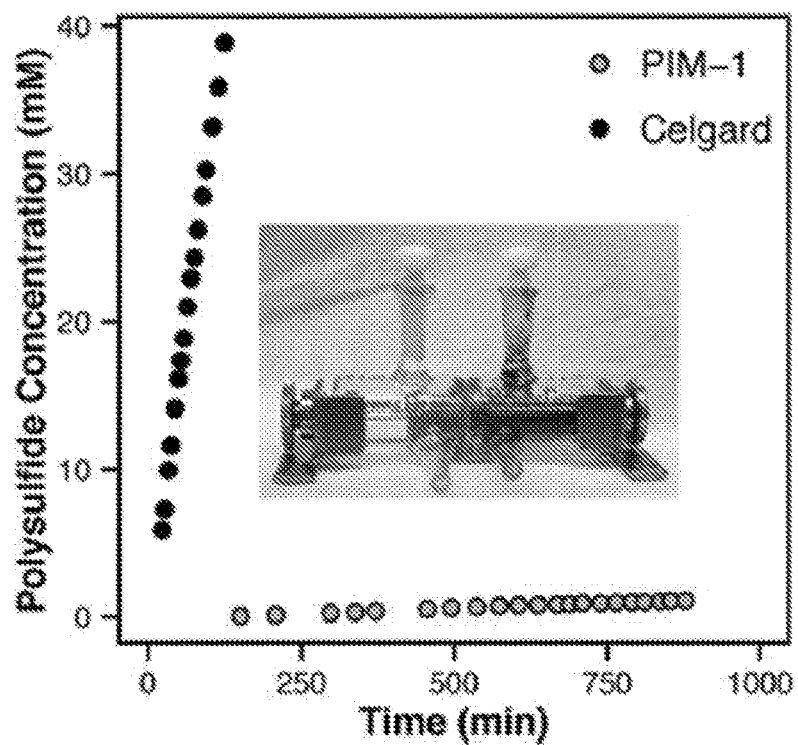
FIG. 7B provides data showing time evolution of concentration of two crossover tests and a photograph of the crossover test cell configuration.
Figure 10:
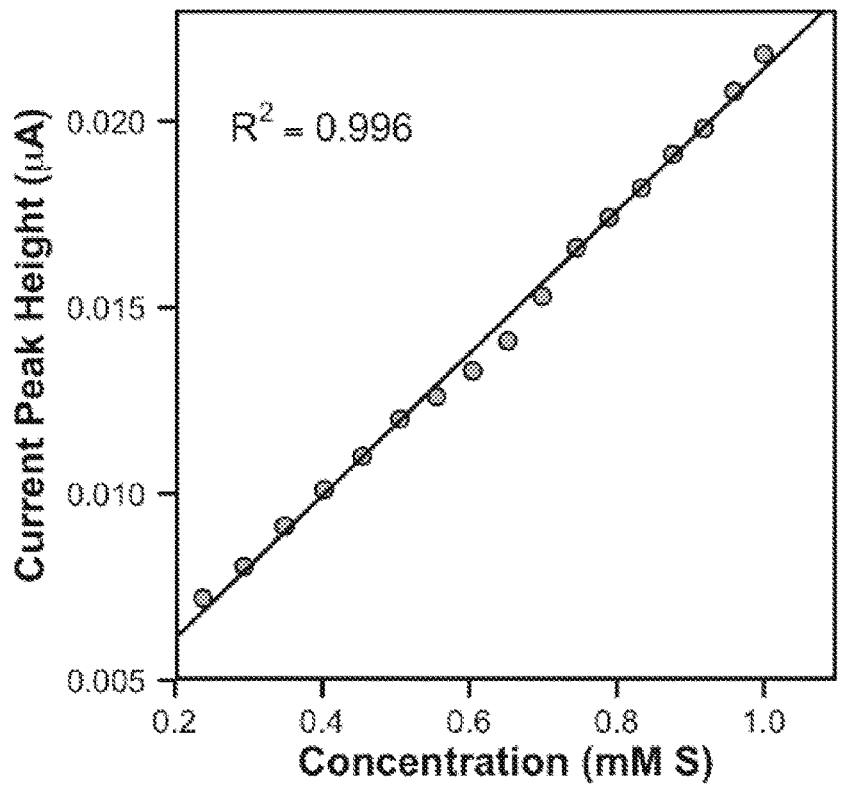
FIG. 10 provides data corresponding to a calibration curve of current vs. concentration obtained via square wave voltammetry.
Figure 11:
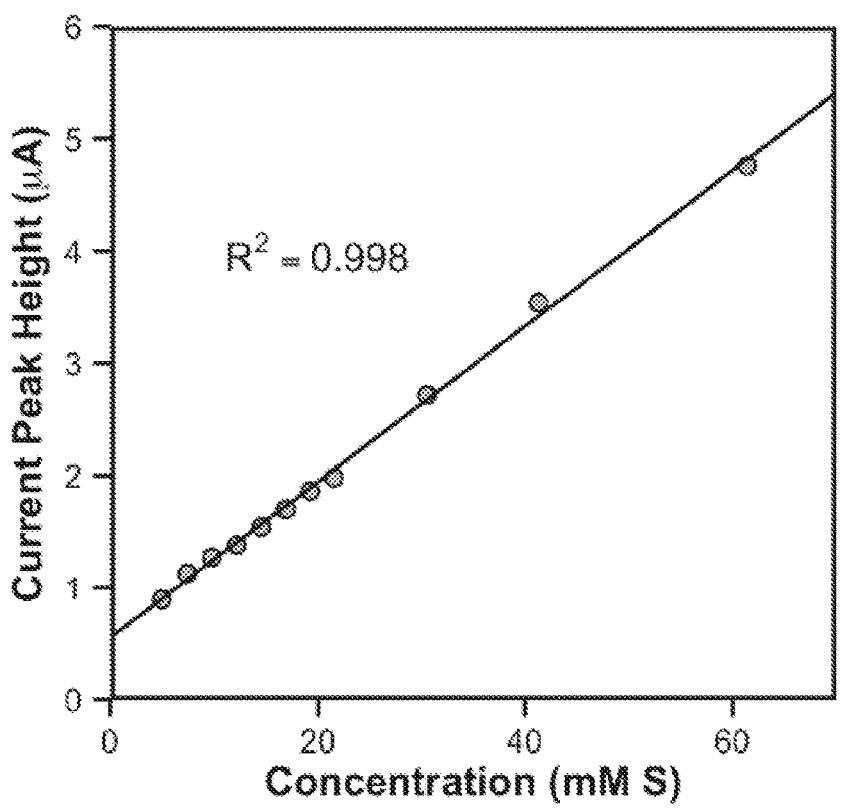
FIG. 11 provides data corresponding to a calibration curve of current vs. concentration obtained via square wave voltammetry.

To quantify the polysulfide-blocking ability of PIM-1 vs Celgard, membrane crossover experiments were performed in H-cells configured with dissolved PS (2.5 M S as $Li_2S_8$ in diglyme containing 0.50 M LiTFSI and 0.15 M $Li_NO_3$) on the retentate side and PS-free electrolyte on the permeate side (FIG. 7B, inset). The concentration of PS over time was then monitored electrochemically on the permeate side using either cyclic voltammetry or square wave voltammetry, where current could be correlated to concentration of PS via a calibration curve (FIG. 10 and FIG. 11). Using an initial rate approximation, the diffusion coefficient of PS across the membranes were calculated to be $6.8 \times 10^{-8}$ cm$^2$ S$^{-1}$ for Celgard and $1.3 \times 10^{-10}$ cm$^2$ s$^{-1}$ for PIM-1 (~500-fold reduction). This is compelling evidence that PS are screened by a size-sieving mechanism within PIM-1's ionically percolating micropore network, as hypothesized. This PS-blocking ability comes at minimal expense to overall membrane ionic conductivity compared to Celgard, thus highlighting the value in guiding membrane design through careful examination of the solvated structures of ions vs redox active species in the electrolyte.

Figure 8A:
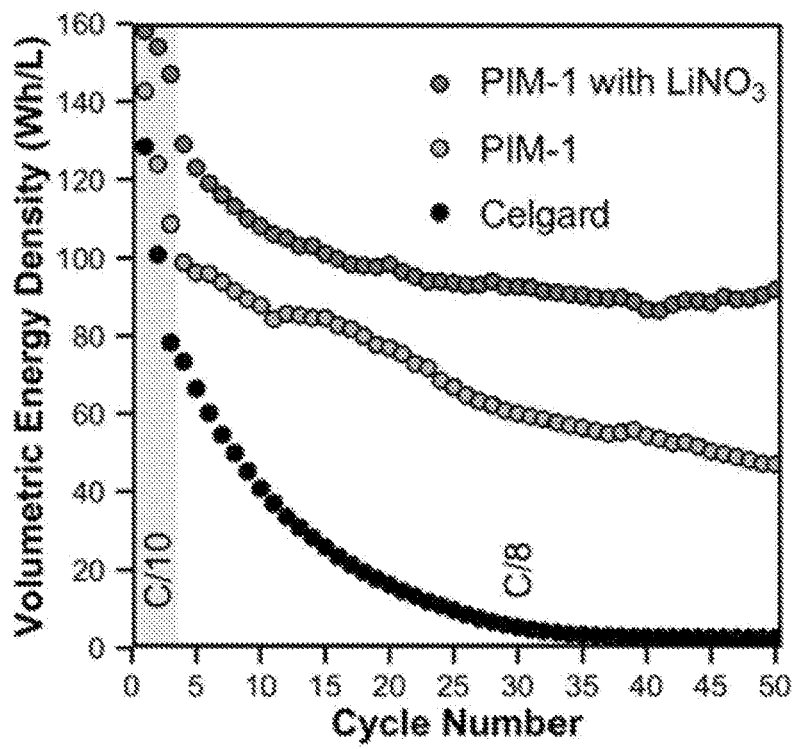
FIG. 8A provides data showing volumetric energy density as a function of cycle number for three systems.
Figure 8B:
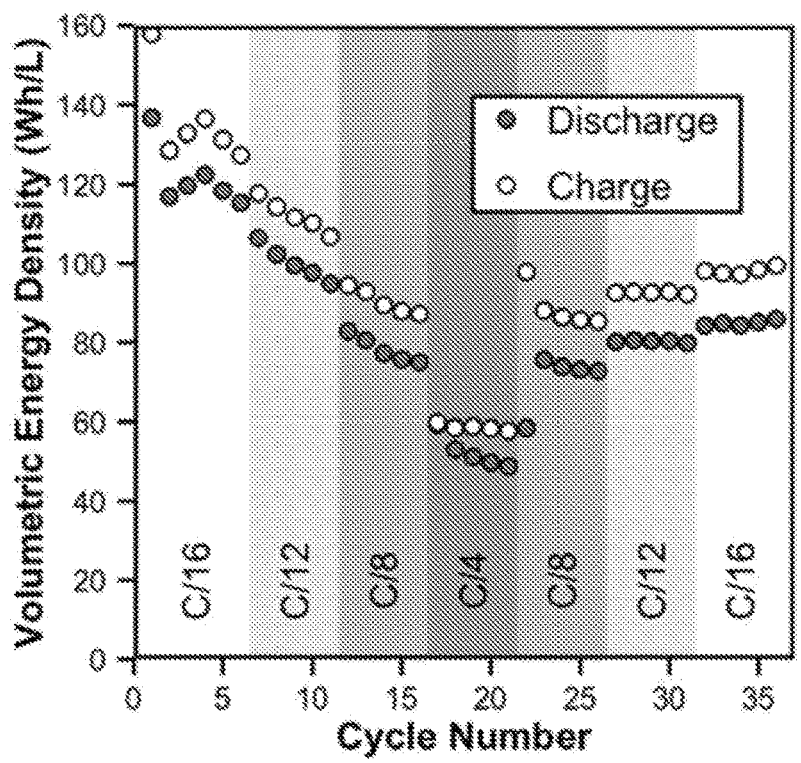
FIG. 8B provides data showing charge and discharge rate performance of an example system.

Given the outstanding PS-blocking ability of the PIM-1 membrane, their performance in Li—S batteries was tested employing soluble sulfur catholytes. To do so, Swagelok cells were assembled with Li-metal anodes, polysulfide catholytes (2.5 M S as Li$_2$S$_8$ in diglyme containing 0.50 M LiTFSI), and Celgard or PIM-1 membranes. Lithium anodes were scraped to reveal a fresh surface prior to cell assembly. Seeking to isolate the membrane's influence on mitigating PS shuttling currents, LiNO$_3$ additives were deliberately avoided in the electrolyte formulation. Moreover, to improve sulfur utilization, 5 wt % Ketjenblack was employed as an embedded current collector in the catholyte. Three break-in cycles at C/10 were used to equilibrate PIM-1's membrane microenvironments before cycling at a C/8 rate. Overall, higher capacity fade was observed for both types of cells during the break-in due to the ample time allowed for polysulfide shuttling. The Li—S cells configured with Celgard membranes exhibited a drastic capacity fade from ~150 Wh L$^{-1}$ after the break-in cycles to less than 20 Wh L$^{-1}$ within the first 20 cycles, all at a C/8 rate. In contrast, batteries configured with PIM-1 membranes exhibited higher capacity at all cycles, sustaining 50 Wh L$^{-1}$ at the end of 50 cycles (FIG. 8A). The performance of PIM-1 membranes was further improved with the addition of LiNO$_3$ as an anode-protecting additive, with a sustained capacity of approximately 100 Wh L$^{-1}$ after 50 cycles (FIG. 8A) and stable cycling at rates as high as C/4 (FIG. 8B). These results represent improvements in capacity retention over related work with Li—S flow cells, particularly in the absence of LiNO$_3$, and highlight the possibility for combining the disclosed membrane approach with other strategies to mitigate the effects of polysulfide crossover.

Redox flow batteries present unique opportunities for low-cost, multi-hour energy storage. In order for RFBs to mature as a deployable technology, their longevity should be greatly improved for battery chemistries offering high-power performance. Toward that end, this Example highlighted the transport needs for membranes employed in nonaqueous Li—S cells, where the cathode was formulated as an energy-dense, flowable solution of polysulfides with Ketjenblack as an embedded current collector. It was showed that rational principles for membrane design emerge from molecular dynamics simulations of the solvated structures of $S_8$, Li$_2$S$_x$ (x=8, 6, or 4), and LiTFSI in different electrolytes, and more specifically, that their calculated radius of gyration places an upper limit of 1.2-1.7 nm on the pore dimensions required for polysulfide blocking. Indeed, this Example showed that membranes processed from polymers of intrinsic microporosity exhibited unprecedented blocking characteristics for soluble polysulfides owing to their sub-nm pore dimensions. This blocking ability led to significantly improved device performance with respect to capacity fade and other important metrics. Given that the pore size, pore chemistry, and overall porosity for PIM membranes are tunable using molecular engineering and polymer processing, the membrane's transport characteristics can be tailored to suit a broad spectrum of electrochemical devices, including stationary batteries and fuel cells.

Figure Captions. FIG. 5: Ion-selective transport across membranes fabricated from PIM-1. For Li—S batteries, both stationary and hybrid flow, blocking Li$_2$S$_x$ (where x≥4) crossover is critical to sustaining peak battery performance. Membranes based on PIM-1 achieve high transport selectivity for LiTFSI by reducing the membrane pore dimensions to subnanometer regimes, which shuts down polysulfide crossover via a sieving mechanism. Ion flux across the membrane is tied to overall microporosity, pore architecture, and electrolyte formulation.

Figure 6A:
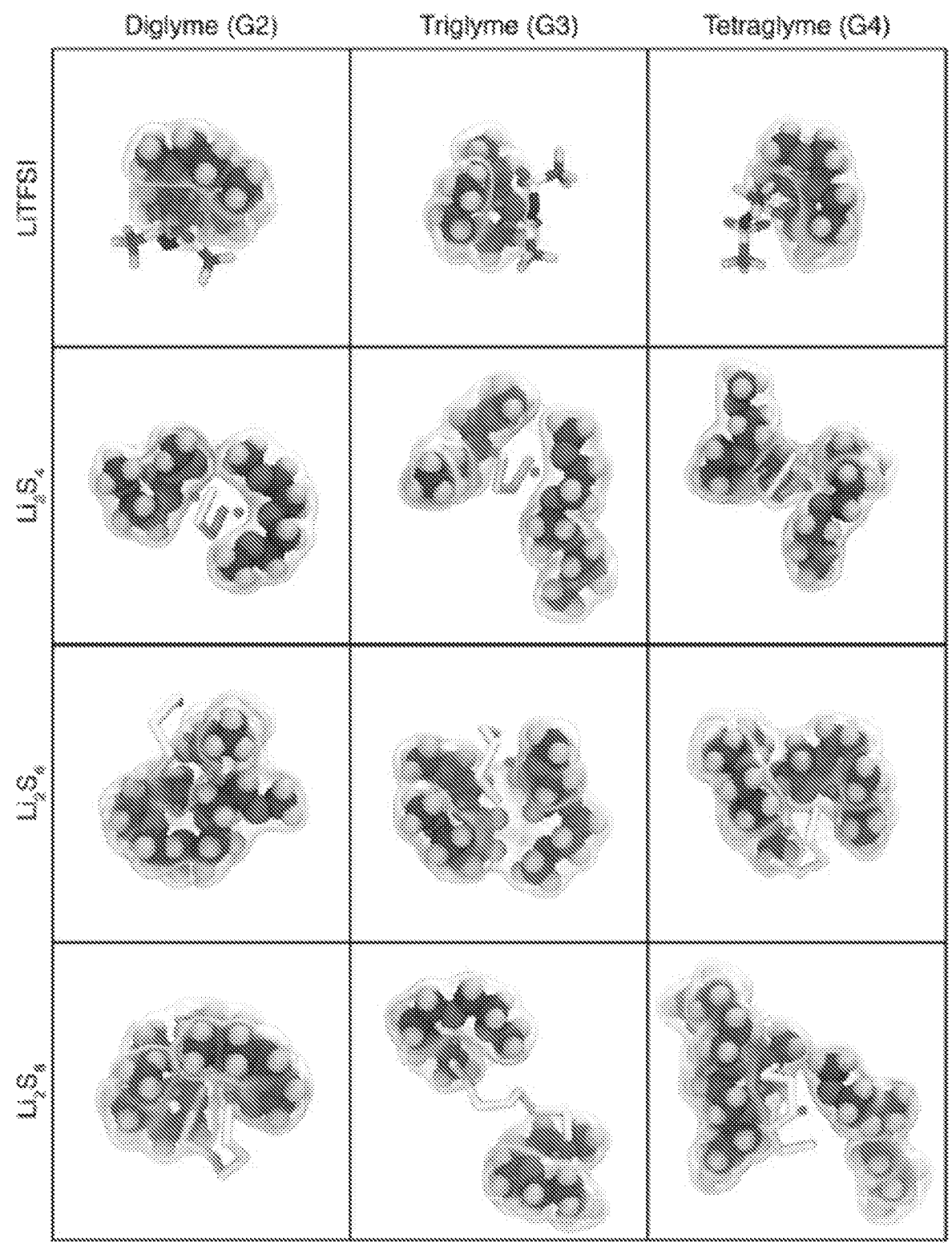
FIG. 6A provides schematic illustrations of molecular models for a variety of polysulfides and lithium bis(trifluoromethanesulfonyl)imide.
Figure 6B:
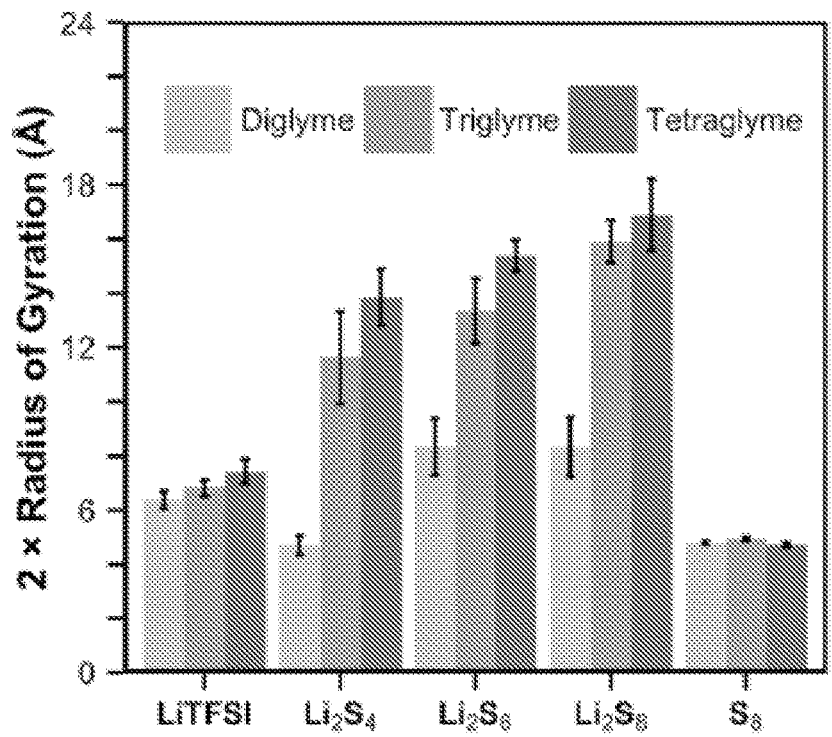
FIG. 6B provides data showing a radius of gyration for a variety of compositions of polysulfides and lithium bis(trifluoromethanesulfonyl)imide.
Figure 6C:
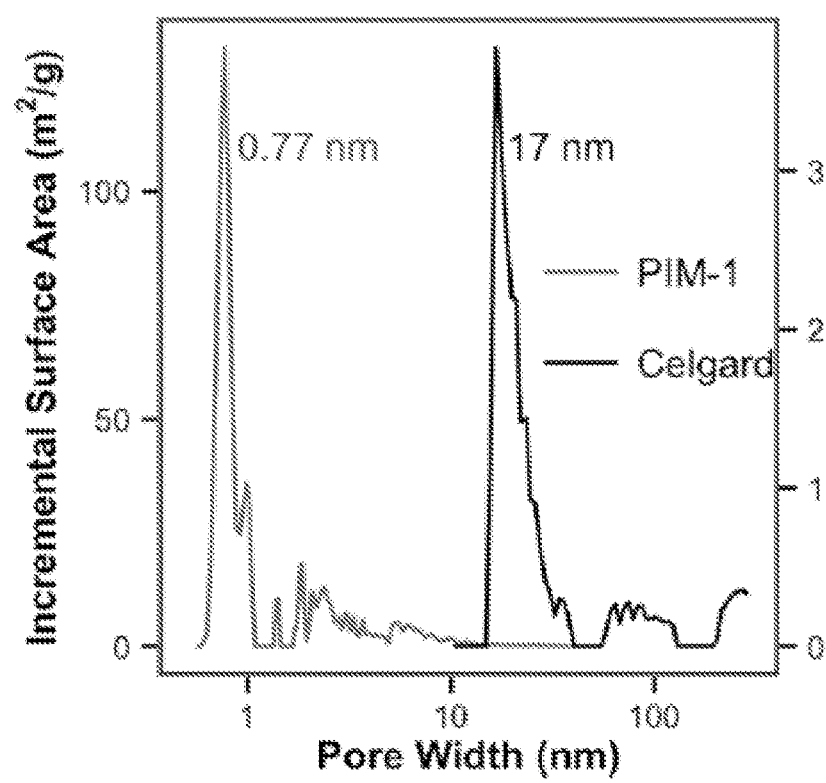
FIG. 6C provides data showing pore size distributions for two materials.

FIG. 6A: Snapshots from MD simulations nearest to the average size of solvated LiTFSI and Li$_2$S$_x$ (x=4, 6, and 8) in diglyme, triglyme, and tetraglyme. FIG. 6B: Calculated radii of gyration (R$_g$) for Li$_2$S$_4$, Li$_2$S$_6$, and Li$_2$S$_8$, along with their first solvation shells, in diglyme, triglyme, and tetraglyme as determined by MD simulations. FIG. 6C: Pore size distributions for microporous PIM-1 vs mesoporous Celgard polymer membranes.

FIG. 7A: Ambient temperature ionic conductivity of microporous PIM-1 vs mesoporous Celgard membranes infiltrated with different electrolyte formulations: 0.50 M LiTFSI in diglyme (G2), triglyme (G3), or tetraglyme (G4). FIG. 7B: Time-evolution of the concentration of PS in the permeate (left) of H-cells configured with either a Celgard (black) or a PIM-1 (green) membrane. The retentate was charged with an initial concentration of 2.5 M S as Li$_2$S$_8$ in diglyme containing 0.50 M LiTFSI and 0.15 M LiNO$_3$. The concentration of PS in the permeate was determined electrochemically.

FIG. 8A: Volumetric energy density as a function of cycle number for Celgard membrane with no LiNO$_3$ (black circles), PIM-1 membrane with no LiNO$_3$ (light green circles), and PIM-1 membrane with LiNO$_3$ additive (dark green circles). FIG. 8B: Rate performance of PIM-1 membrane with LiNO$_3$ additive.

Experimental Details. Materials: Tetraglyme (G4), triglyme (G3), diglyme (G2), 3,3,3',3'-tetramethyl-1,1'-spirobiindane-5,5',6,6'-tetraol and tetrafluoroterephthalonitrile were purchased from Sigma Aldrich. Lithium nitrate, sulfur (Puratronic, 99.9995% (metals basis)), lithium sulfide (99.9% (metals basis)), and lithium metal (99.9% (metals basis), 1.5 mm) were purchased from Alfa Aesar. Lithium bis(trifluoromethanesulfonyl)imide (LiTFSI) was purchased from 3M. Celgard 2535 membrane was purchased from MTI Corporation. Ketjenblack EC-600JD was purchased from AkzoNobel.

General methods: Nuclear magnetic resonance (NMR) spectra were taken on a Bruker Avance II 500 MHz NMR spectrometer. Analysis of the polymer's molecular weight distribution was carried out using size exclusion chromatography on a Malvern Viscotek TDA 302 system. Residual water content for various solvents was determined by a Mettler Toledo C20 Coulometric Karl Fischer titrator. Electrochemical experiments and battery testing were conducted with a BioLogic VMP3 potentiostat. Scanning electron micrographs were obtained with a Zeiss Gemini Ultra-55 analytical scanning electron microscope equipped with in-lens and secondary electron detectors at a beam energy of 2 keV. Ellipsometric porosimetry (EP) was performed on a Semilab PS-1100 instrument with toluene or isopropanol.

Electrode details: Swagelok batteries were constructed using Swagelok unions purchased from Swagelok Northern California. Associated electrodes were made in-house from nickel 200 rods with outer diameters of 1.27 cm. Wells, which were 0.635 cm in diameter and 0.508 mm deep, were machined into the cathode current collectors. Gold was sputtered onto the cathode current collector surface. Anode current collectors were flat, bare nickel 200 surfaces.

Membrane preparation: PIM-1 was synthesized using a literature procedure. PIM-1 was dissolved in chloroform at a concentration of 12.5 mg mL$^{-1}$. Films of PIM-1 were cast by depositing 1 mL of solution into a 3.5 cm diameter Teflon well. The solvent was left to evaporate in a closed vacuum chamber under ambient pressure for 1 h or until dryness. The films were further dried in vacuo overnight. The dried films were punched into 7/16-inch circles. Celgard 2325 membranes were punched into ½-inch circles. All membranes were soaked in relevant electrolytes overnight before use.

Ionic conductivity measurements: Soaked membranes were sandwiched between two stainless steel blocking electrodes. Potentio electrochemical impedance spectroscopy (PEIS) was used with 50 mV AC bias scanning from 1 MHz to 100 mHz. The high frequency x-axis intercept is taken to be the resistance of the membrane. The membrane conductivity was then calculated taking into account the cell geometry.

Electrolyte and polysulfide preparation: The supporting electrolyte formulation for all battery cycling and conductivity measurements was 0.50 M LiTFSI. LiNO$_3$ was added to the electrolyte only for the crossover experiments detailed below. LiTFSI was dried for 16 h under vacuum at 150° C. LiNO$_3$ was dried for 16 h under vacuum at 110° C. Diglyme was tested for peroxides prior to use; if any were measured, it was stirred with alumina, filtered, and sparged with argon. Diglyme was dried with activated 3 Å molecular sieves until it measured <20 ppm H$_2$O. Electrolyte was tested for water content and confirmed to contain <30 ppm water before use. Solutions of Li$_2$S$_8$ (2.50 mol S L$^{-1}$ in electrolyte) were prepared by mixing Li$_2$S (0.287 g, 6.25 mmol), sulfur (1.40 g, 5.47 mmol), and 20 mL of electrolyte and heating at 60° C. until all solids were dissolved. Li$_2$S$_8$ solutions were kept at 60° C. in order to prevent precipitation of insoluble species and cooled to room temperature prior to use. Cathode slurry with 5% w/w conductive additive was made by adding 30.8 mg of Ketjenblack to 500 μL of Li$_2$S$_8$ solution and mixed for 15 min.

Crossover experimental methods: Crossover measurements were made by placing respective membranes between the cell halves of a PermeGear Side-Bi-Side diffusion cell. To the permeate side of the cell was added 2.5 mL of supporting electrolyte (0.15 M LiNO$_3$, 0.5 M LiTFSI in diglyme) while to the retentate side was added 2.5 mL of 2.5 M S as Li$_2$S$_8$ in electrolyte. In this case, due to the presence of lithium as a reference electrode, LiNO$_3$ was necessary to prevent the reaction of polysulfides with the lithium. Crossover was determined by cyclic voltammetry and square wave voltammetry measurements of the permeate side of the cell. Cyclic voltammetry allowed concentrations between 5.0-60 mM to be measured while square wave voltammetry allowed for measurements of concentrations ranging from 0.20-1.0 mM. Given the different rates of crossover between the two materials, both techniques were necessary as the Celgard crossover was too fast to be measured accurately with the SWV, and the PIM crossover was too slow to be measured in a convenient time frame with CV. A glassy carbon disc electrode (1 mm) was obtained from BAS Inc. (West Lafayette, Ind.), polished before use and used as the working electrode. Lithium metal was used as the reference and counter electrodes. A calibration curve for each electrochemical technique was obtained by measuring the current as a function of voltage for a set of known concentration polysulfide solutions (FIG. 9 and FIG. 10). The concentration of polysulfide vs. time for the crossover measurements was then calculated using the linear equation determined from the calibration curves.

Battery cycling: Cathode slurry was spread evenly into the cathode well. Lithium chip was punched using a 7/16-inch bore and pressed onto the anode. Due to the safety concern of dendrite formation, membranes were sandwiched between two Celgard layers to isolate them from the lithium polysulfide slurry and the lithium anode surface. The trilayer membrane was then pressed in between the two electrodes to assemble a Swagelok battery.

Computational Methods. First-Principles molecular dynamics simulations: The S$_8$/Li-TFSI/Li$_2$S$_x$-TEGDME systems were simulated using a modified version of the mixed Gaussian and plane wave code CP2K/Quickstep. A triple-ζ basis set was employed with two additional sets of polarization functions (TZV2P) and a 320 Ry plane-wave cutoff. The unknown exchange-correlation potential is substituted by the revised PBE generalized gradient approximation, and the Brillouin zone is sampled at the Γ-point only. Interactions between the valence electrons and the ionic cores are described by norm-conserving pseudopotentials. The Poisson problem is tackled using an efficient Wavelet-based solver. The poor description of the short-range dispersive forces within the PBE-GGA exchange-correlation functional was overcome by employing DFTD3 empirical corrections. In order to equilibrate the systems, 10 ps of NPT dynamics was performed, using a Nose-Hoover thermostat (temperature damping constant of 100 fs) and an Anderson barostat (pressure damping constant of 2 ps). Snapshots of the system were saved every step. The snapshot with a volume closest to the average of the last 5 ps of MD was then selected as input for an additional 20 ps simulation in the constant volume, constant temperature (canonical or NVT) ensemble.

Structural analysis: The "size" of the solvated lithium polysulfide species was estimated as the sum of two terms: 1) the radius of gyration of the solute (R$_{gyr}$) and 2) the size of the glyme solvation shell. All structural analyses were performed for every 10 snapshots from the last 20 ps of the NVT AIMD simulations (4,000 for each system). The R$_{gyr}$ was computed as $$R_{gyr} = \sqrt{\frac{1}{M}\sum_i m_i(r_i - r_{cm})^2}$$

where M is the total mass of the solute, R$_{cm}$ is the center of mass and the sum is over all r$_i$ atoms in the solute.

The solvation environment around each dissolved polysulfide was obtained calculating the Li-glyme (oxygen atom) and S-glyme pair distribution functions (PDF) from the last 20 ps NVT MD simulation. The 1st solvation shell was obtained from the minimum in the PDF after the first peak, and the number of solvent molecules obtained by simple integration.

FIG. 9: Cross-sectional scanning electron micrograph of a freestanding PIM-1 membrane. The scale bar is 10 μm.

FIG. 10: Calibration curve of current vs. concentration obtained via square wave voltammetry for the lower concentration regime.

FIG. 11: Calibration curve of current vs. concentration obtained via cyclic voltammetry for the higher concentration regime.

Figure 12:
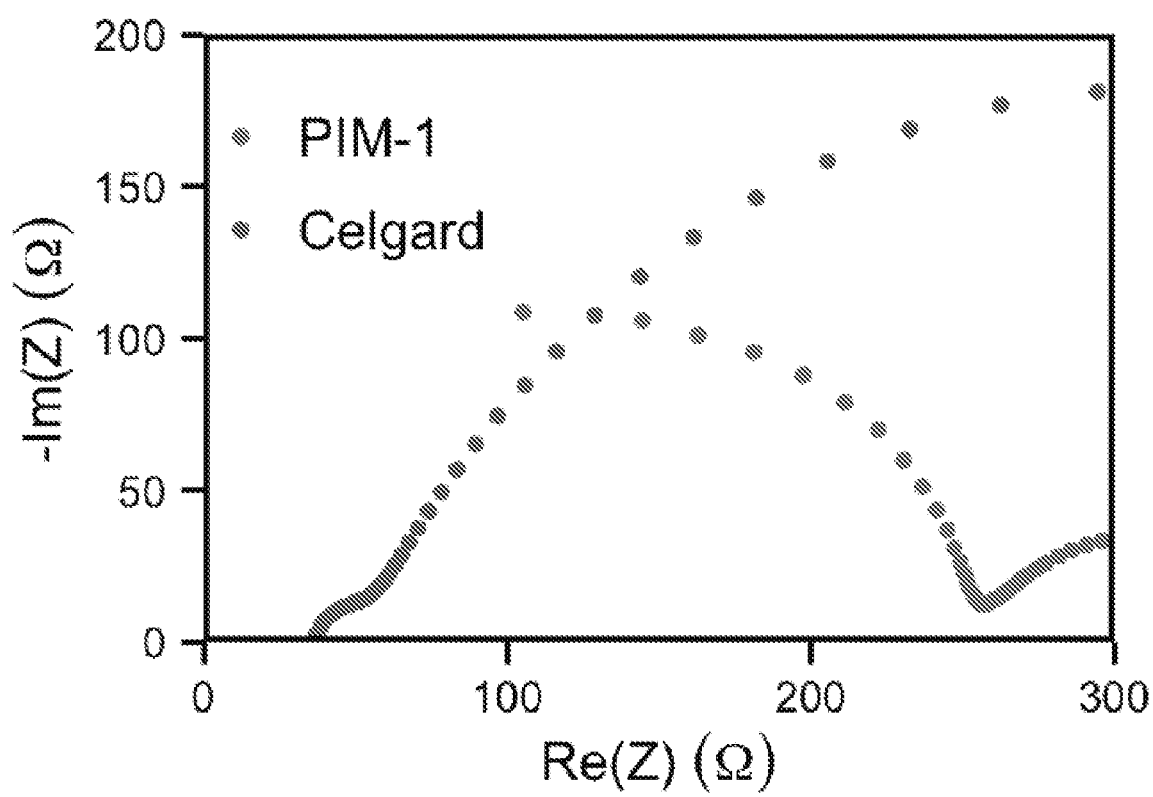
FIG. 12 provides data showing electrochemical impedance spectra of two systems.

FIG. 12: Electrochemical impedance spectroscopy (EIS) of Li—S cells configured with PIM-1 and Celgard as membranes, respectively. The membrane ionic conduction kinetics are represented by the sizes of high-frequency semicircles, which are 20.1 Ohms and 215.1 Ohms for Celgard and PIM-1, respectively.

Figure 13A:
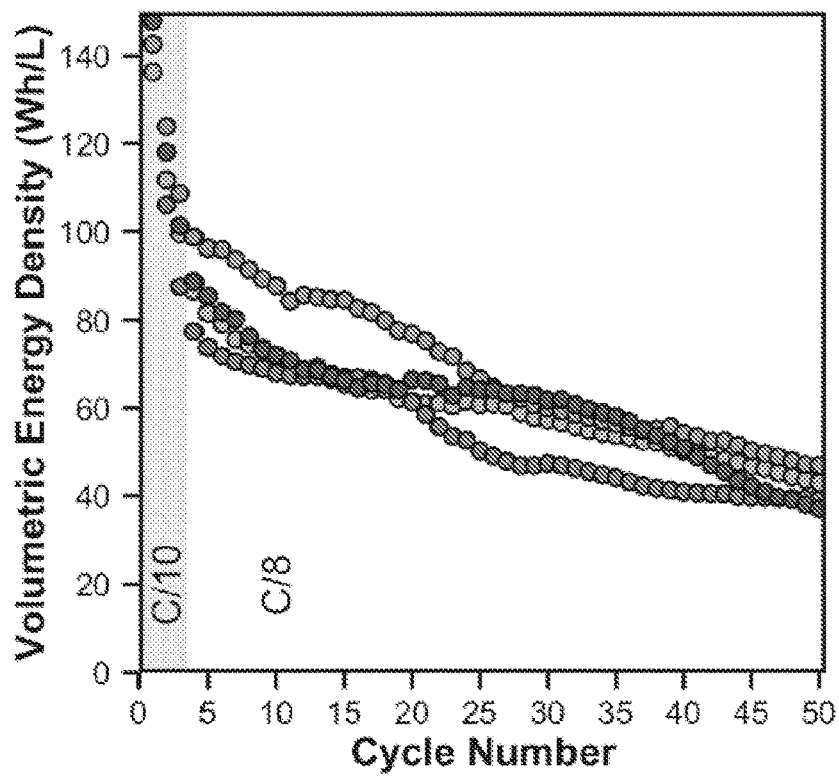
FIG. 13A provides data showing volumetric energy density of different batteries as a function of cycle number for battery systems including a separator embodiment comprising a polymer of intrinsic microporosity.
Figure 13B:
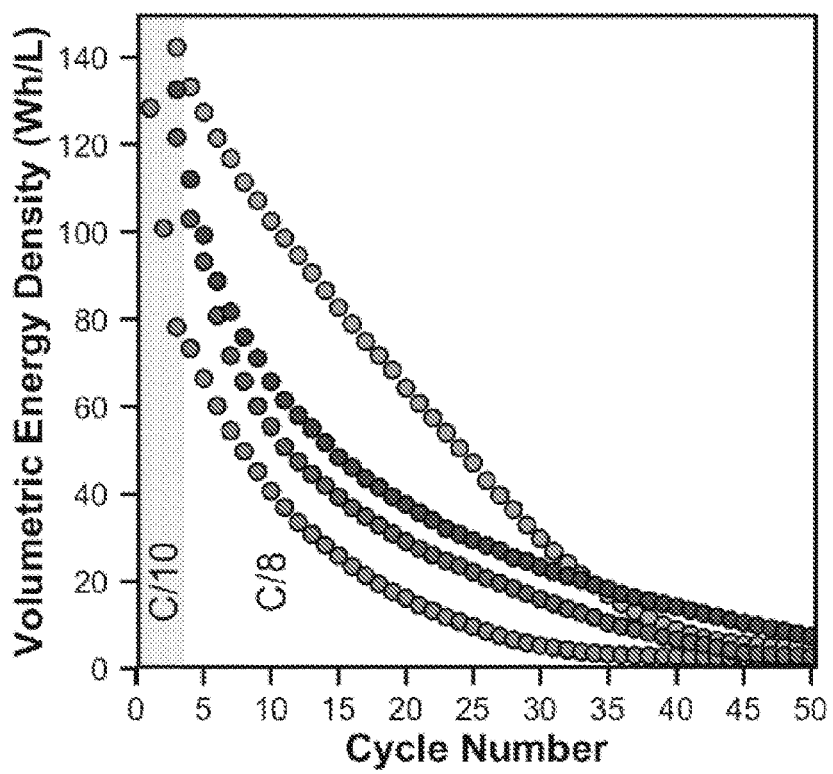
FIG. 13B provides data showing volumetric energy density of different batteries as a function of cycle number for battery systems including a Celgard separator.

FIGS. 13A-13B: Volumetric energy densities of all batteries tested (catholyte formulation: 2.5 M S as $Li_2S_8$ in diglyme containing 0.50 M LiTFSI) with either PIM-1 membrane (green circles, FIG. 13A) or Celgard membrane (purple circles, FIG. 13B).

Figure 14A:
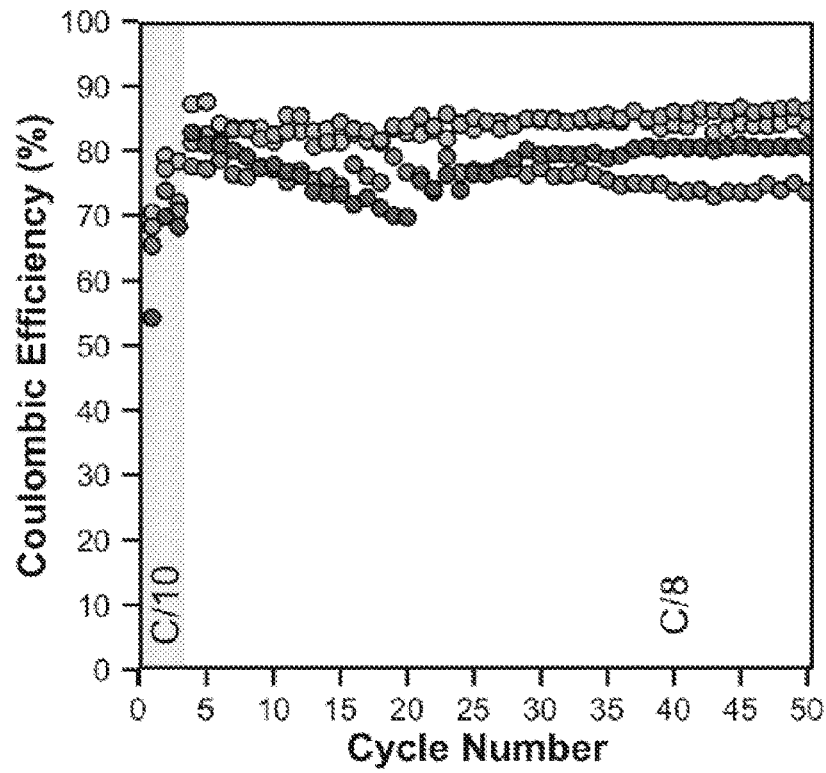
FIG. 14A provides data showing Coulombic efficiencies of different batteries as a function of cycle number for battery systems including a separator embodiment comprising a polymer of intrinsic microporosity.
Figure 14B:
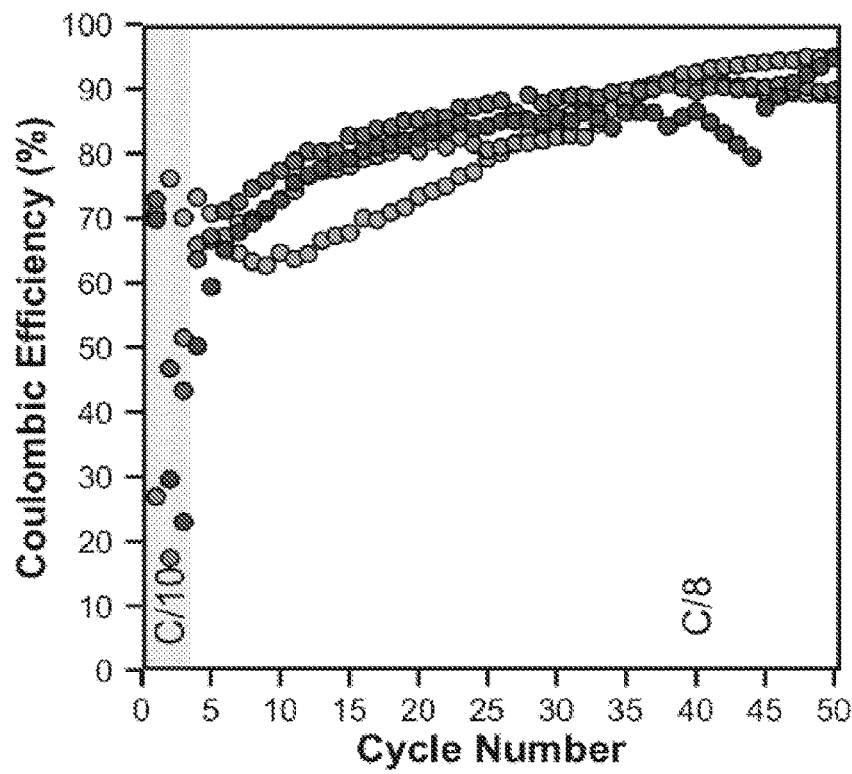
FIG. 14B provides data showing Coulombic efficiencies of different batteries as a function of cycle number for battery systems including a Celgard separator.

FIGS. 14A-14B: Coulombic efficiencies of all batteries tested (catholyte formulation: 2.5 M S as $Li_2S_8$ in diglyme containing 0.50 M LiTFSI) with either PIM-1 membrane (green circles, FIG. 14A) or Celgard membrane (purple circles, FIG. 14B).

Figure 15A:
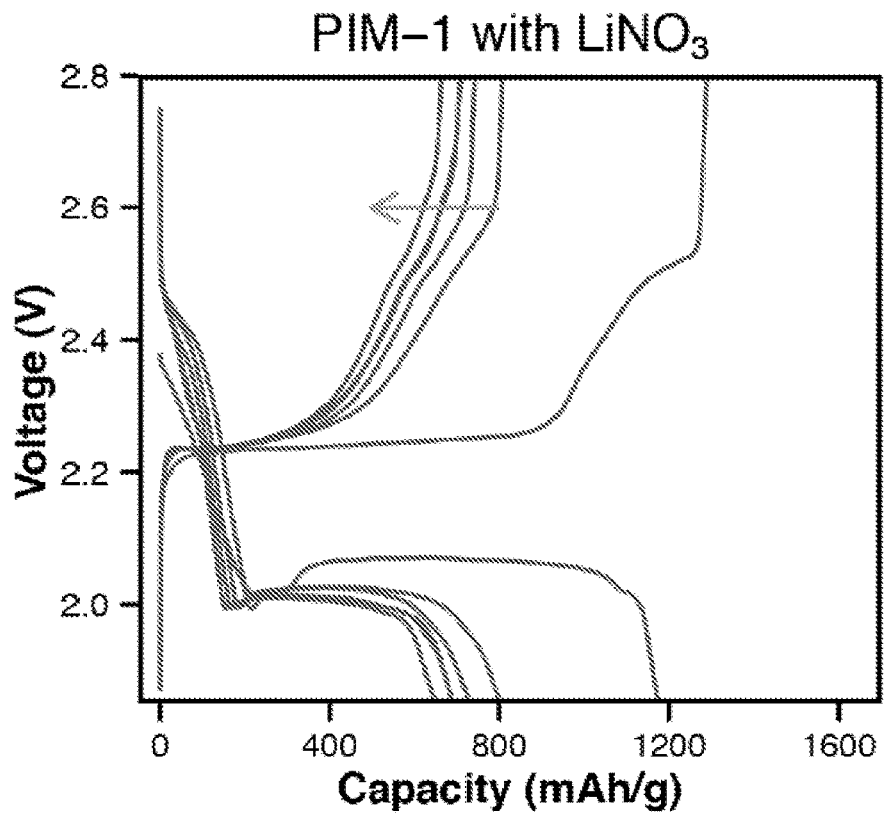
FIG. 15A provides data showing discharge and charge profiles for battery systems including a separator comprising a polymer of intrinsic microporosity.
Figure 15B:
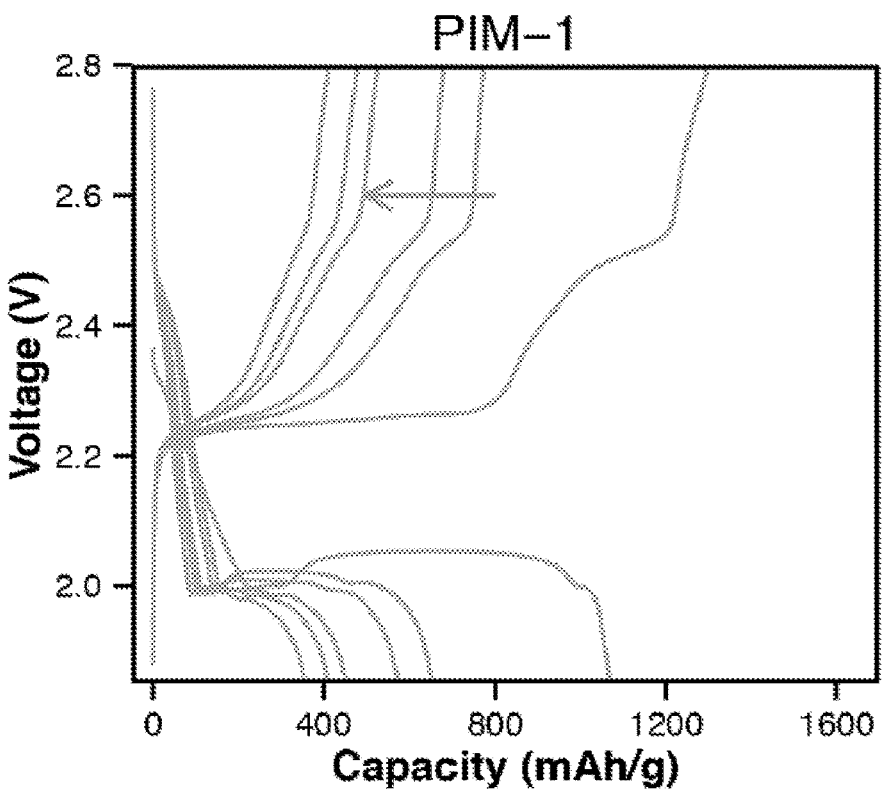
FIG. 15B provides data showing discharge and charge profiles for battery systems including a separator comprising a polymer of intrinsic microporosity.
Figure 15C:
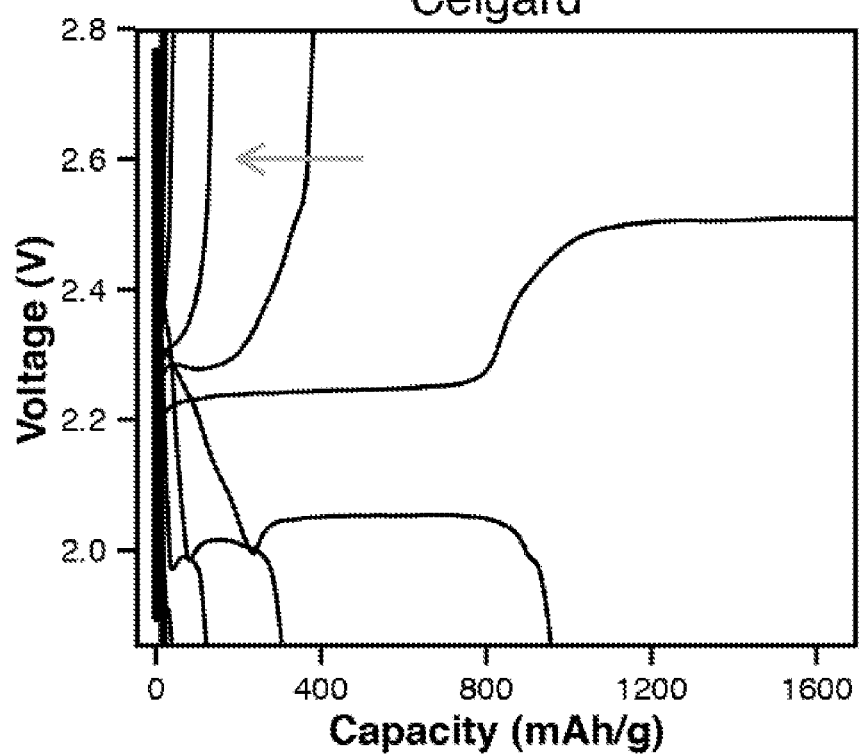
FIG. 15C provides data showing discharge and charge profiles for battery systems including a conventional separator.

FIGS. 15A-15C. Discharge and charge profiles for Li—S batteries configured with: (FIG. 15A) PIM-1 membrane separators and $LiNO_3$ electrolyte additive; (FIG. 15B) PIM-1 membrane separators without $LiNO_3$ electrolyte additive; and (FIG. 15C) Celgard separators without $LiNO_3$ additive at the 1st, 10th, 20th, 30th, 40th, and 50th cycles. The arrows indicate the direction of higher cycle number.

Figure 16:
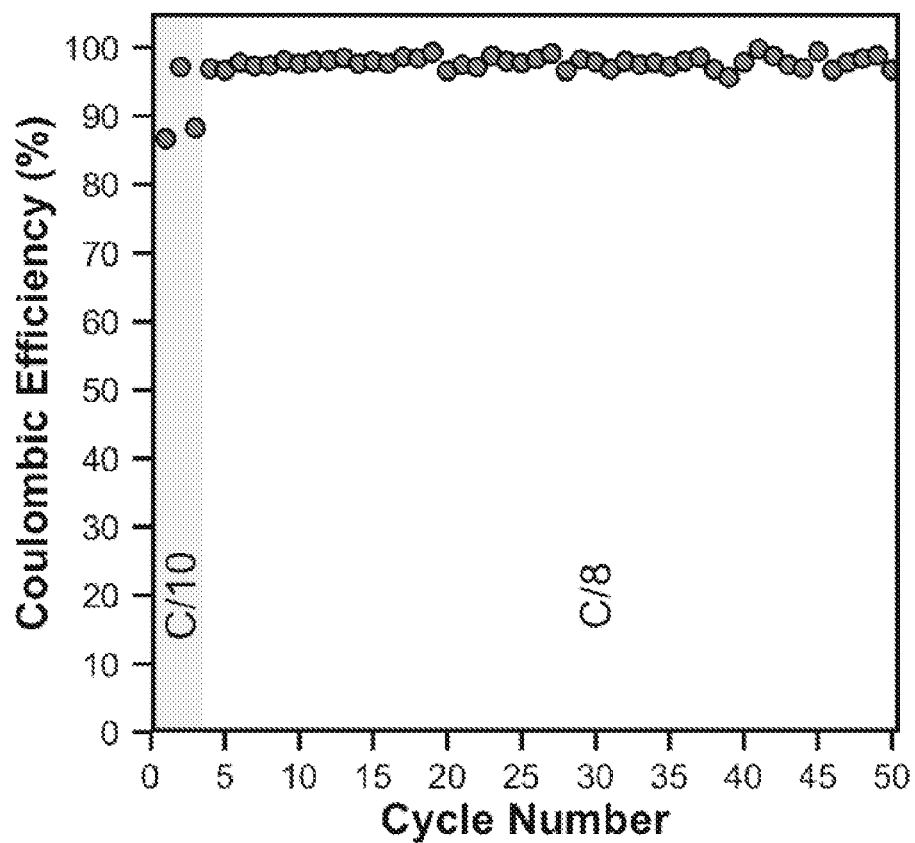
FIG. 16 provides data showing Coulombic efficiency of a battery including a separator comprising a polymer of intrinsic microporosity as a function of cycle number.

FIG. 16: Representative Coulombic efficiency of a Li—S battery configured with a PIM-1 membrane separator and $LiNO_3$ as an electrolyte additive.

Additional description may be found in the article Nano Lett., 2015, 15 (9), pp 5724-5729 (DOI: 10.1021/acs.nanolett.5b02078), and its Supporting Information, which are hereby incorporated by reference.

Example 2. Ion- and Size-Selective Membranes for Electrochemical Energy Storage Devices Based on Polymers with High Intrinsic Microporosity Electrochemical energy storage (EES) devices rely on chemically-robust and ion-selective membranes to ensure durability. Despite the importance of preventing membrane degradation for long-term battery operation, little is known about the design rules that tie local chemical changes in the membrane to evolution in its macroscopic structure and ion-selectivity. This Example presents a strategy for discovering these design rules, using the polysulfide-blocking ability of PIM-1 membranes as a model system of study. PIM-1 features electrophilic 1,4-dicyanooxanthrene functionalities that are potentially subject to nucleophilic attack by lithium polysulfides, which are endogenous to lithium-sulfur batteries. This chemical reactivity was verified with in situ FT-IR experiments on the membrane as well as NMR and ESI-MS experiments on model compounds representing monomer segments. It was found that it was advantageous to significantly increase the prevalence of these polysulfide adducts, formally lithiated thioamides, in order to observe a significant decrease in the membrane's polysulfide-blocking ability, which were found to correlate to an increase in membrane pore size. This work suggests PIM-1 membranes perform optimally in lithium-sulfur batteries configured with composite sulfur cathodes, where the polysulfide concentration in electrolyte remains low.

Electrochemical energy storage (EES) devices rely on separators or membranes to electrically isolate the negative and positive electrodes while allowing ionic current to flow between them. For EES devices with solid-state electrodes (e.g., Li-ion or lithium-sulfur batteries), mesoporous polymer separators often serve this purpose. On the other hand, for EES devices that use soluble active-materials (e.g., redox flow batteries or lithium-polysulfide batteries), more advanced membranes capable of blocking active-species crossover while allowing counter-ions to pass may be useful. To this end, a number of membrane materials for selective lithium-ion transport in non-aqueous electrolytes have been proposed, including lithiated Nafion, solid polymer electrolytes, Li-ion conducting glasses, and polymers of intrinsic microporosity (PIMs). These membranes must maintain their active-species blocking ability to ensure long lifetimes and high efficiency, even if those active-species are highly reactive. Despite the importance of membrane stability, little is known about the effect of chemical reactivity on transport selectivity for these membranes. This Example uses size-selective, polysulfide-blocking membranes cast from PIM-1, a polymer of intrinsic microporosity, as a model system for understanding the design rules needed to stabilize their performance as ion-selective membranes for lithium-sulfur (Li—S) and lithium-polysulfide (Li—PS) EES devices.

Li—S and Li—PS EES devices are attractive technologies due to the high specific capacity (1675 mAh $g^{-1}$) and low cost of sulfur. The reduction of sulfur to lithium sulfide proceeds through intermediates consisting of highly soluble lithium polysulfides—$Li_2S_n$, where 4≤n≤8—that can diffuse across the cell and react with the anode, leading to the well-known shuttle effect. This shuttling effect is known to decrease cell lifetime and efficiency. To address the polysulfide crossover problem, size-selective membranes based on polymers of intrinsic microporosity (PIMs) that block polysulfide crossover while allowing Li-ion transport may be used. PIMs are unique in that they have permanent microporosity due to frustrated packing of polymer chains in the solid state. This property makes PIMs both highly permeable and well suited as size-selective membranes because the pore size can be carefully chosen to block active-species crossover while allowing lithium ion transport. Despite these promising characteristics, little is known about their chemical stability in EES devices or the impact of polymer reactivity on polymer structure and transport behavior.

Figure 17:
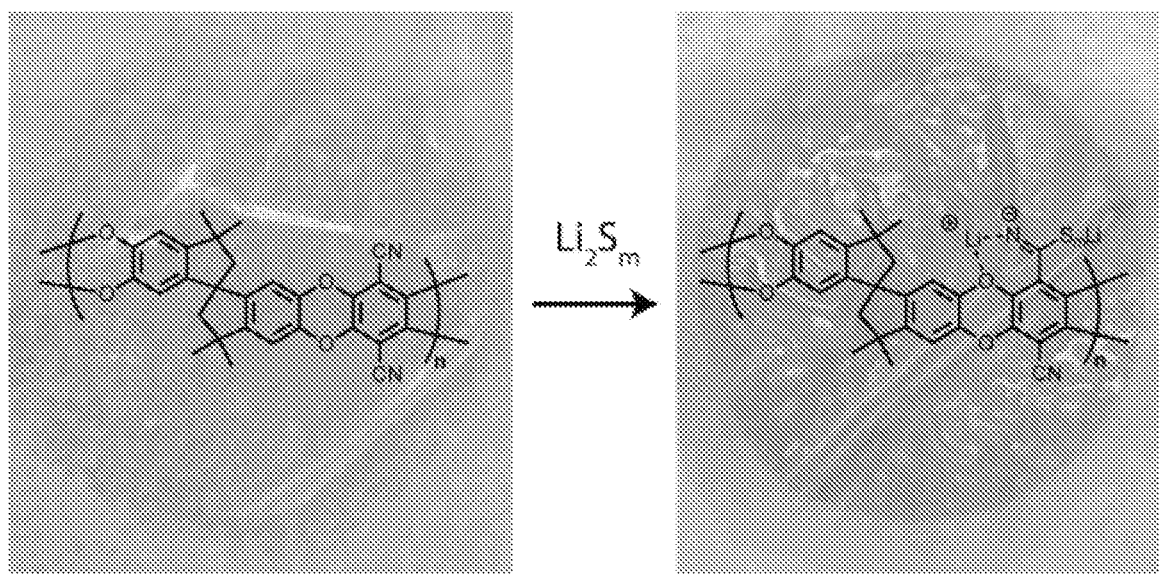
FIG. 17 provides photographs of a polymer of intrinsic microporosity (left) and a modified polymer of intrinsic microporosity (right), along with chemical structures of the polymers.

During the operation of both Li—S and Li—PS EES devices, lithium polysulfides are in direct contact with the membrane. Lithium polysulfides are both nucleophilic and reducing to many organics with low-lying LUMOs. It was hypothesized that electrophilic 1,4-dicyanooxanthrene functionalities in PIM-1 might be prone to nucleophilic attack by $Li_2S_n$, forming lithiated thioamides (FIG. 17). To that end, it was noted during post-mortem analysis of cycled Li—PS batteries that PIM-1 membranes changed in color from bright yellow to orange, suggesting a chemical reaction had indeed taken place. In addition to the color change, membranes that were soaked in polysulfide solution were subsequently insoluble in chloroform, while membranes that were soaked in solvent or electrolyte retained their chloroform solubility. The product of that transformation was not immediately known, nor was its impact on PIM-1's ion-selective transport ability. Thus, detailed chemical analysis of the reaction products was carried out along the reaction trajectory using a variety of spectroscopic methods—including in situ FT-IR and NMR spectroscopy—and local changes in PIM-1's pore chemistry were linked to changes in macroscale pore architecture and related transport selectivity.

Figure 18A:
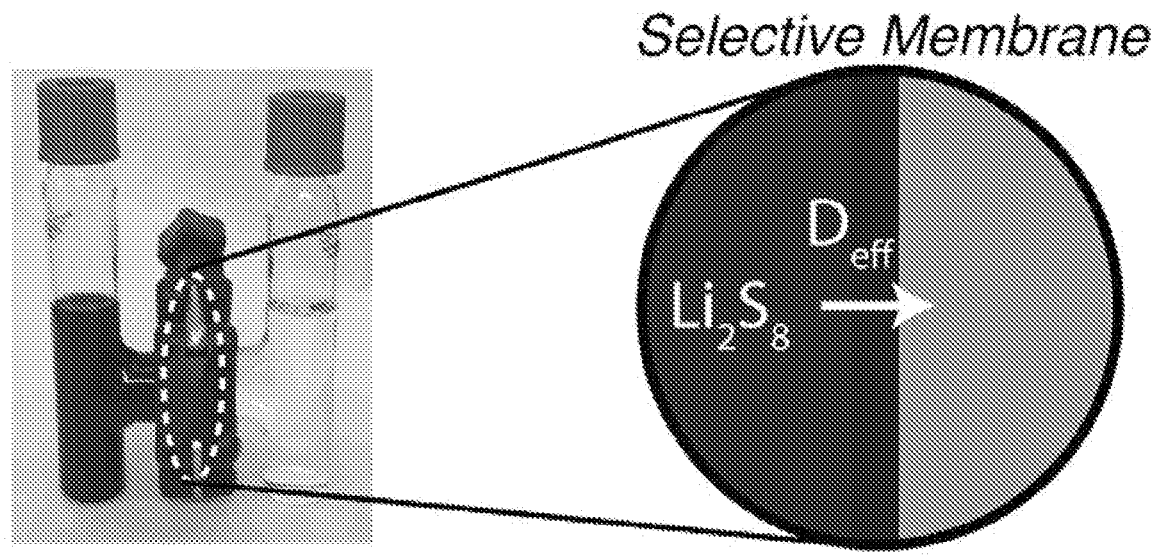
FIG. 18A provides a photograph and configuration of a test cell.
Figure 18B:
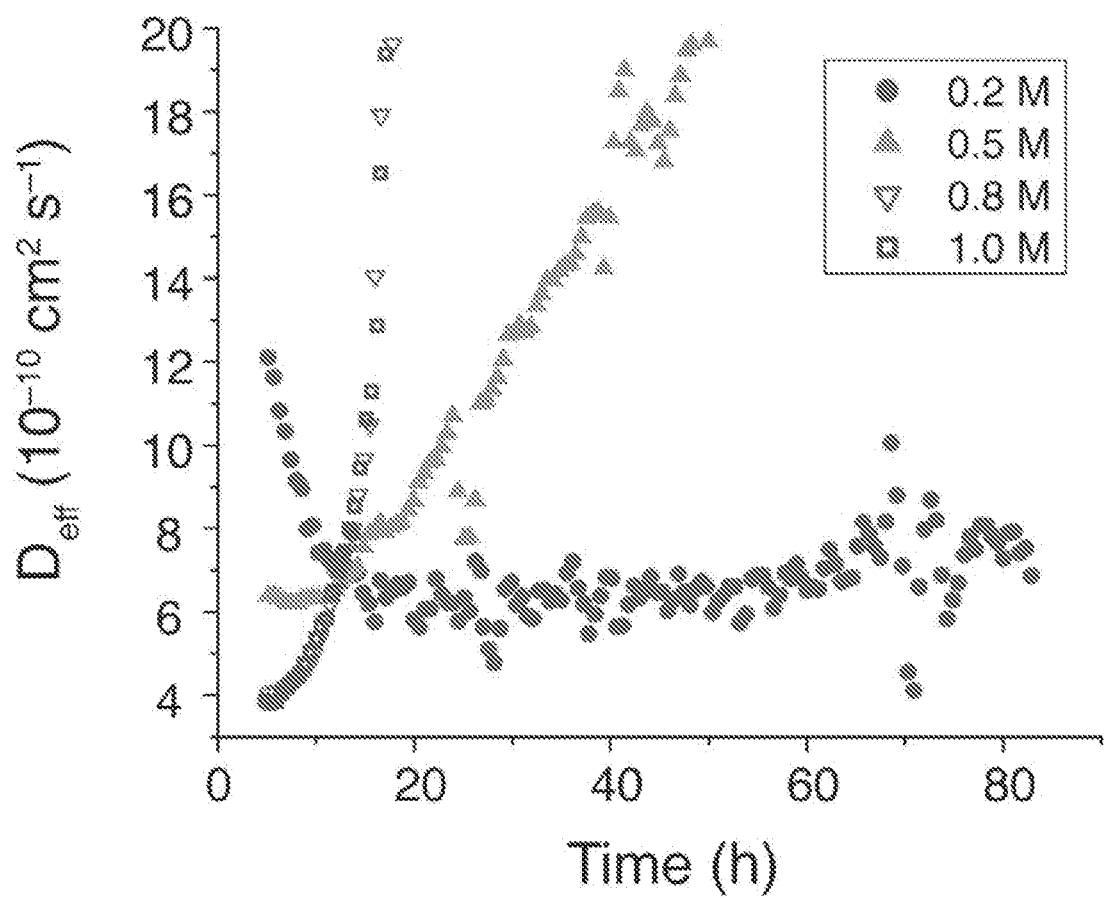
FIG. 18B provides data showing the effective rate of diffusion across a membrane comprising a polymer of intrinsic microporosity for different cell concentrations.

In order to understand the effect of chemical reactivity on the selectivity of PIM-1 membranes, long-term measurements of the polysulfide blocking-ability of PIM-1 were conducted. During these measurements, it was found that the effective diffusion coefficient ($D_{eff}$) of lithium polysulfides through PIM-1 membranes was not constant; instead, it gradually increased over time. In order to test whether this change in polysulfide-blocking was related to the proposed chemical reaction with lithium polysulfides or an unrelated membrane degradation mechanism, crossover rate as a function of $Li_2S_n$ concentration in the electrolyte in contact with the membrane was systematically investigated. These measurements were carried out by placing a PIM-1 membrane of known thickness and area between two compartments of electrolyte. One of these compartments (the retentate) contained an initial concentration ($C_0$) of $Li_2S_n$, while the other initially contained none (the permeate). The concentration of $Li_2S_n$ in the permeate compartment was then measured as a function of time, and $D_{eff}$ of $Li_2S_n$ through the membrane could be calculated from the slope of this plot (see below, FIGS. 21A-21C). For an ideal membrane that does not react with $Li_2S_n$ or degrade otherwise, $D_{eff}$ should be small and should not change with time. It was observed that for $C_0=0.20$ M S as $Li_2S_8$, $D_{eff}$ decreased from $1.2\times10^{-9}$ to $6.4\times10^{-10}$ cm$^2$ s$^{-1}$ during the first 15 h of the crossover experiment (FIGS. 18A-18B). This decrease was followed by a gradual increase to $7.9\times10^{-10}$ cm$^2$ s$^{-1}$ after 80 h. At higher $C_0$, the increase in $D_{eff}$ with time was much sharper. For instance, with $C_0=0.50$ M S, $D_{eff}$ increased from $6.3\times10^{-10}$ to $2.0\times10^{-9}$ cm$^2$ s$^{-1}$ after 50 h. For $C_0=0.80$ M and 1.0 M, $D_{eff}$ had a lower initial value of $3.9\times10^{-10}$ cm2 s$^{-1}$ followed by a sharp increase to $2.0\times10^{-9}$ cm$^2$ s$^{-1}$ after 18 h. At all concentrations of sulfur, the membrane's polysulfide blocking-ability degraded, with faster degradation at higher sulfur concentrations. This concentration dependence implies that the degradation in membrane performance is due to a chemical reaction rather than mechanical failure. This trend points towards a change in the pore structure that is caused by chemical reactivity of the membrane.

To verify the proposed reactivity pathway with NMR and mass spectrometry, model compound 1 was synthesized and allowed to react with excess $Li_2S_8$ in 1:1 (v/v) THF-d$_8$: diglyme (FIGS. 19A-19D). In the presence of 20 equiv. $Li_2S_8$, $^1$H-NMR shows complete conversion of the model compound into several different species of lithiated thioamides, all of which have one unreacted nitrile group (FIG. 19B, FIGS. 22A-24). This distribution of products was expected, as it is well known that lithium polysulfides in solution exist as a variety of species with different chain lengths. Negative-ion mode high-resolution electrospray ionization mass spectrometry (ESI-MS) provided further evidence for the conversion of the nitrile group in the model compound to a lithiated thioamide. The most intense peak in the ESI-MS spectrum corresponded to [1+SH]$^-$ (m/z obsd. 485.12, calc. 485.15), which forms from hydrolysis of the proposed species in the presence of adventitious water. Smaller peaks corresponding to [1+Li$_3$S$_n$]$^-$, where n=5 (m/z obsd. 633.04, calc. 633.08), 6 (m/z obsd. 665.01, calc. 665.05), 7 (m/z obsd. 696.99, calc. 697.03), and 8 (m/z obsd. 728.96, calc 729.00) were also observed, providing strong evidence for the conversion of 1 into lithiated thioamide species (FIGS. 19C-19D, FIGS. 25-26).

Figure 20B:
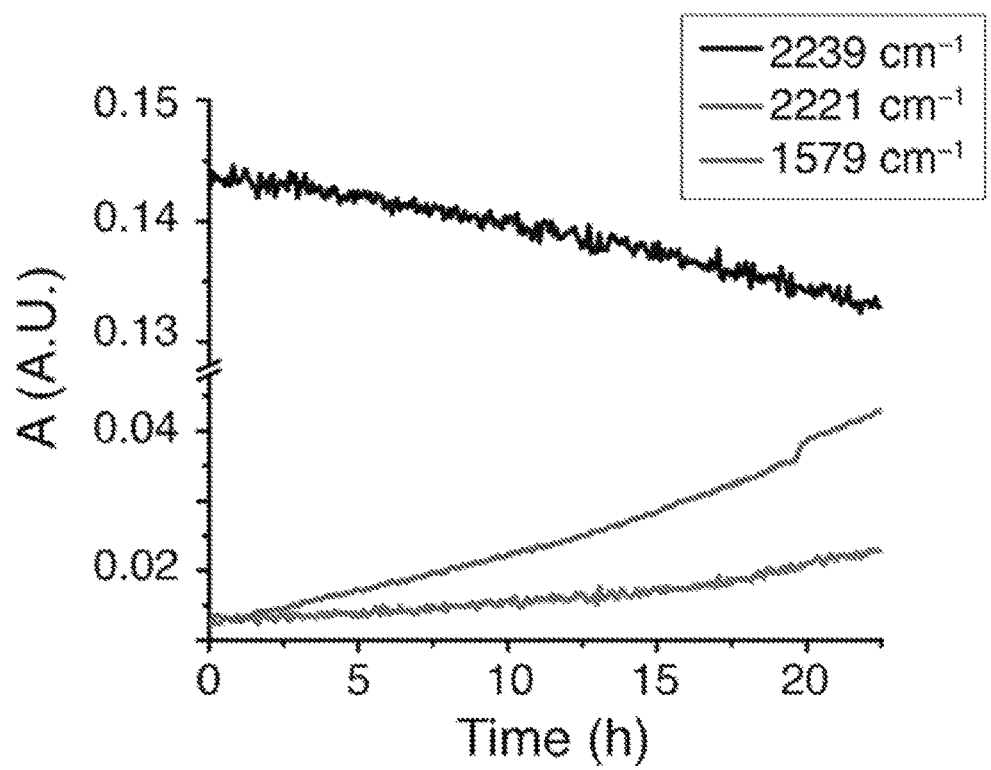
FIG. 20B provides data showing the time-evolution of peak intensities during modification of a polymer of intrinsic microporosity.
Figure 20C:
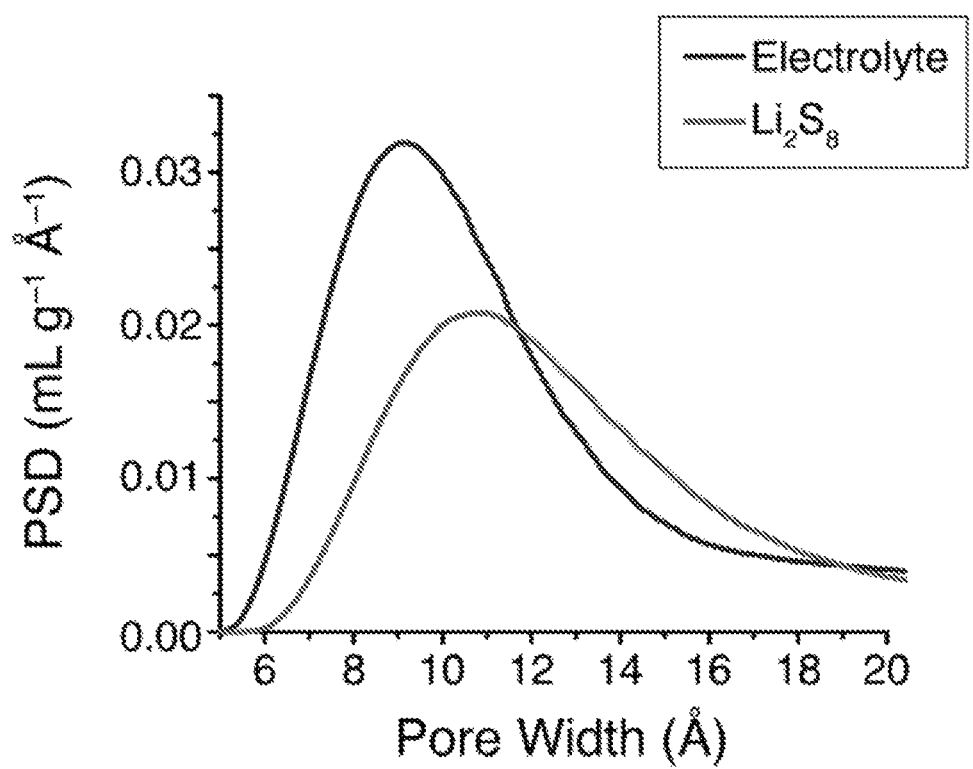
FIG. 20C provides pore size distribution data for a polymer of intrinsic microporosity and a modified polymer of intrinsic microporosity.
Figure 27:
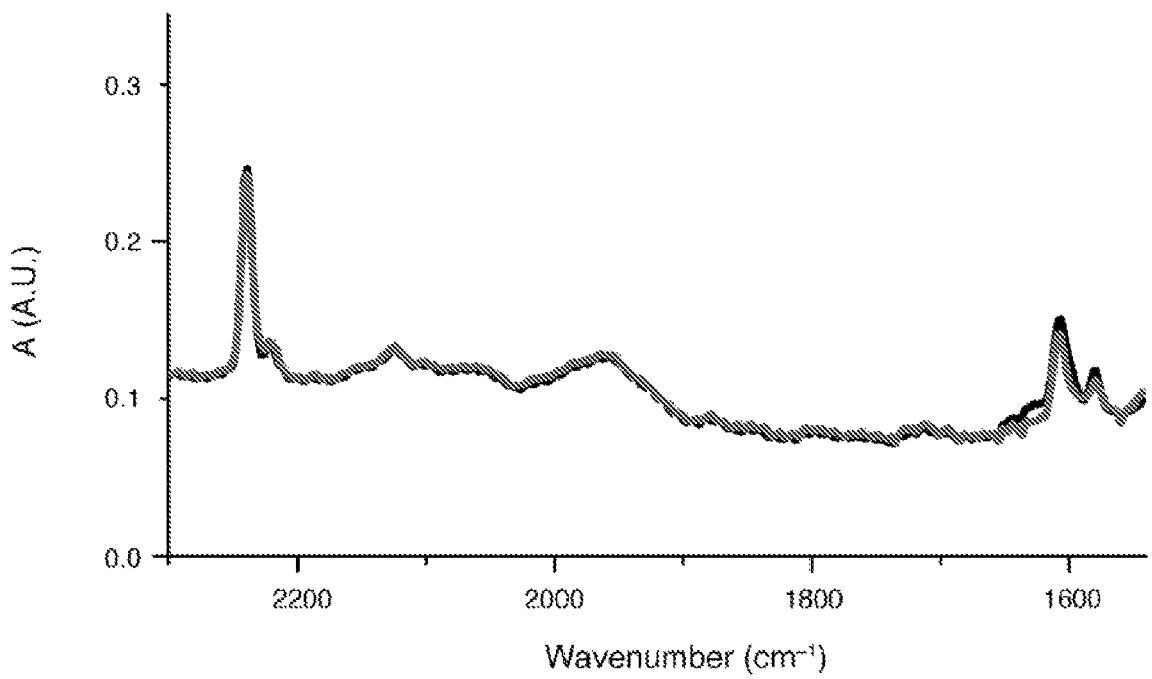
FIG. 27 provides a Fourier Transform Infrared spectrum of a modified polymer of intrinsic microporosity.
Figure 28:
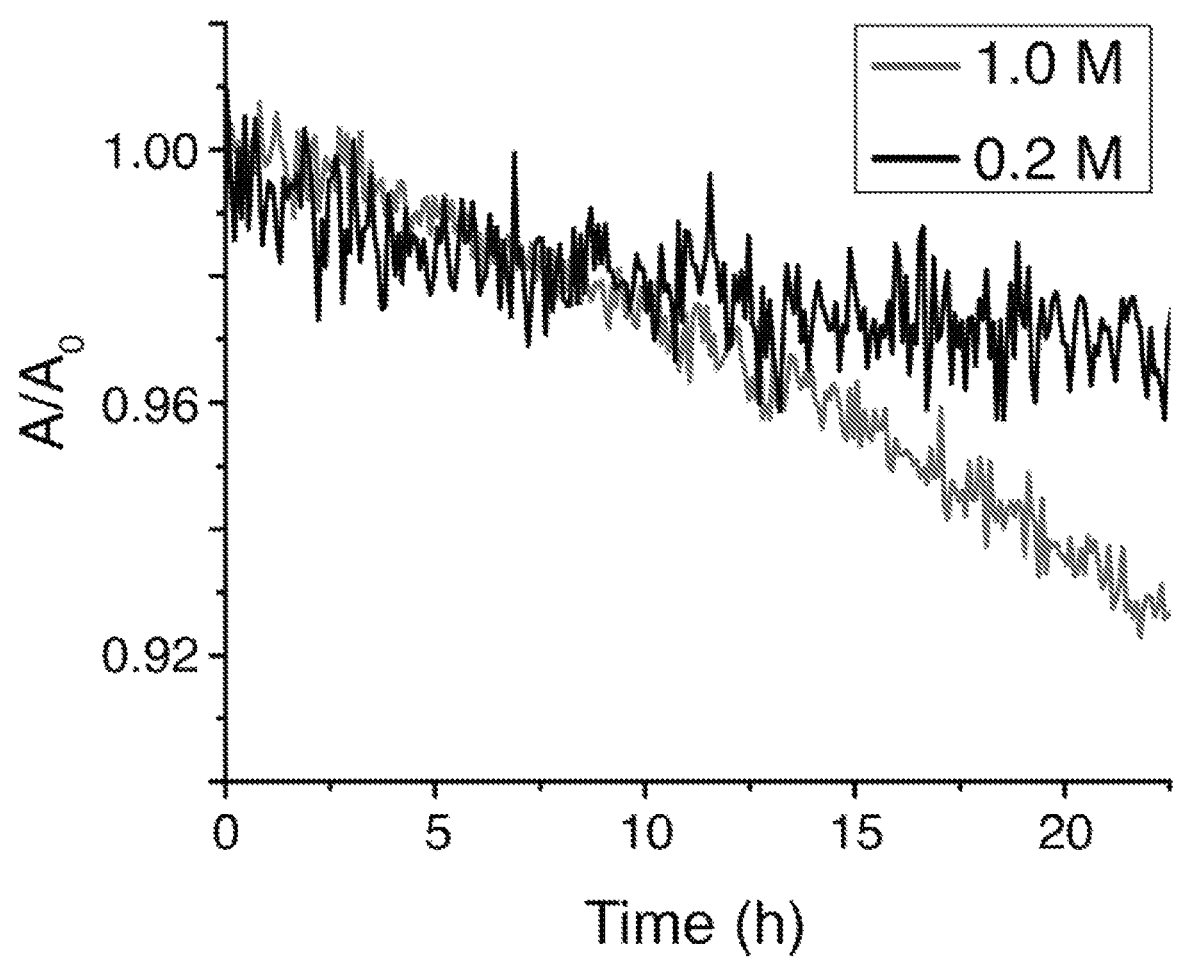
FIG. 28 data showing a normalized intensity of a portion of Fourier Transform Infrared spectra for two different conditions.

Having established the reactivity of the nitrile groups of PIM-1 with the aid of a model compound, it was sought to measure the extent and rate of this reaction with in situ FT-IR spectroscopy. A thin film of PIM-1 was deposited on an ATR probe that was immersed in 1.0 M S as $Li_2S_8$ in electrolyte. The intensity of the nitrile stretch at 2239 cm$^{-1}$ slowly decreased in intensity to 92% of its initial value after 22.5 h (FIGS. 20A-20C). Concomitantly, new stretches at 2221 cm$^{-1}$ and 1579 cm$^{-1}$ appeared and grew in intensity. The stretch at 2221 cm$^{-1}$ is attributable to unreacted nitrile groups adjacent to the newly formed thioamide, while the stretch at 1579 cm$^{-1}$ is consistent with the thioamide functional group. After 22.5 h, the polysulfide solution was removed and replaced with electrolyte, and the new peaks persisted, indicating that the chemical reaction is not reversible in the presence of electrolyte (FIG. 27). The time-scale for conversion of nitrile groups on PIM-1 to lithiated thioamides is similar to the time-scale of increased crossover rates (FIG. 17), providing compelling evidence that the change in membrane active-species blocking ability is due to its chemical evolution. Further evidence for this hypothesis was provided by repeating the in situ FT-IR experiment in the presence of 0.2 M S as $Li_2S_8$. As expected, the chemical reaction was slower, with the nitrile peak only decreasing to 97% of its initial value after 22.5 h (FIG. 28). These experiments show that changes in membrane chemical reactivity are directly correlated to changes in membrane selectivity, with larger extents of conversion of nitrile to lithiated thioamide corresponding to lower membrane selectivity.

On the basis of model compound studies, in situ FT-IR, and concentration-dependent crossover, it is clear that PIM-1 reacts with lithium polysulfides and that this reactivity correlates with decreased active-species blocking ability. In order to understand how the chemical reactivity of PIM-1 leads to a change in active-species blocking, gas adsorption experiments were used to relate changes in polymer chemistry to changes in the pore structure of the membrane. PIM-1 membranes were soaked in electrolyte or electrolyte containing 1.0 M S as $Li_2S_8$, washed thoroughly, and dried under vacuum at 120° C. for 19 h. Nitrogen adsorption isotherms were measured at 77 K, and BET surface areas and pore size distributions were calculated. Both isotherms were characterized by high nitrogen uptake at very low pressures that is typical of microporous materials, as well as pronounced hysteresis that is commonly observed for PIMs. Unreacted PIM-1 membranes had a BET surface area of 570 m$^2$ g$^{-1}$ and typical pore width of 9 Å, which is consistent with reported values (FIG. 20C, FIGS. 29A-29C). In contrast, the reacted PIM-1 membranes had a BET surface area of 431 m$^2$ g$^{-1}$ along with larger pores with a typical width of 11 Å. These results suggest that the reacted PIM-1 packs less efficiently than PIM-1 in the solid state due to the presence of lithiated thioamide appendages. This change in polymer structure provides a reasonable explanation for the decreased polysulfide-blocking ability of PIM-1 after soaking in solutions of lithium polysulfides. In addition to changes in the dry polymer structure after reaction with lithium polysulfides, it is also possible that the proposed reactivity effects the solvation of polymer chains, thus further altering the structure of the polymer in its swollen state.

Membranes capable of sustained blocking of active-species crossover are critical for the implementation of next-generation EES devices. Unfortunately, relatively little is known about how proposed membranes evolve in the presence of highly reactive electrolytes. This Example systematically studied the chemical evolution of a promising membrane material (PIM-1) in the presence of dissolved lithium polysulfides and found that the nitrile groups on the polymer backbone react with lithium polysulfides to form lithiated thioamides. This change in chemical structure of the polymer leads to a change in the membrane's pore architecture, causing a decrease in active-species blocking ability. The insights gained here highlight the importance of understanding the interplay between chemical reactivity and membrane performance and point the way toward rational molecular design of selective membranes with improved chemical stability and performance. The design rules exposed in this Example indicate that PIM-1 membranes are suitable for use in cells with relatively low concentrations of lithium polysulfides (i.e., Li–S batteries with a composite sulfur cathode). In the presence of higher polysulfide concentrations, new strategies, including post-synthetic modification to reduce reactivity and cross-linking may be useful for ensuring long-term membrane selectivity.

Experimental. PIM-1 and model compound 1 were synthesized. Free-standing membranes were prepared by drop-casting 12.5 mg mL$^{-1}$ solutions of the polymer in chloroform into Teflon-coated wells under a crystallization dish. After several hours of slow drying in air, the membranes were dried under vacuum and soaked in electrolyte for at least 6 hours. Crossover measurements were performed in a custom-purposed glass H-cell obtained from Adams & Chittenden Scientific Glass (Berkeley, Calif.) with an aperture diameter of 1.6 cm. Polysulfide concentration in the permeate compartment was measured by cyclic voltammetry with a 1 mM diameter glassy carbon working electrode and a lithium foil counter/reference electrode. High-resolution electrospray ionization mass spectrometry (ESI-MS) was performed in the negative ion mode on a dilute sample of 1+20 equiv. Li$_2$S$_8$. Pore size distributions were calculated from adsorption isotherms using the SAIEUS software package with a heterogeneous surfaces NLDFT model.

Figure Captions. FIG. 17. Proposed chemical reactivity between PIM-1 and lithium polysulfides, Li$_2$S$_n$. Background: color change of PIM-1 membrane after soaking in 2.5 M S as Li$_2$S$_8$ for 5 days.

FIG. 18A: Photograph of the H-cell used for crossover measurements and schematic depicting diffusion of Li$_2$S$_8$ across a membrane. FIG. 18B: Measured values of D$_{eff}$ for Li$_2$S$_8$ across PIM-1 membranes as a function of time for different initial concentrations of Li$_2$S$_8$.

Figure 19A:
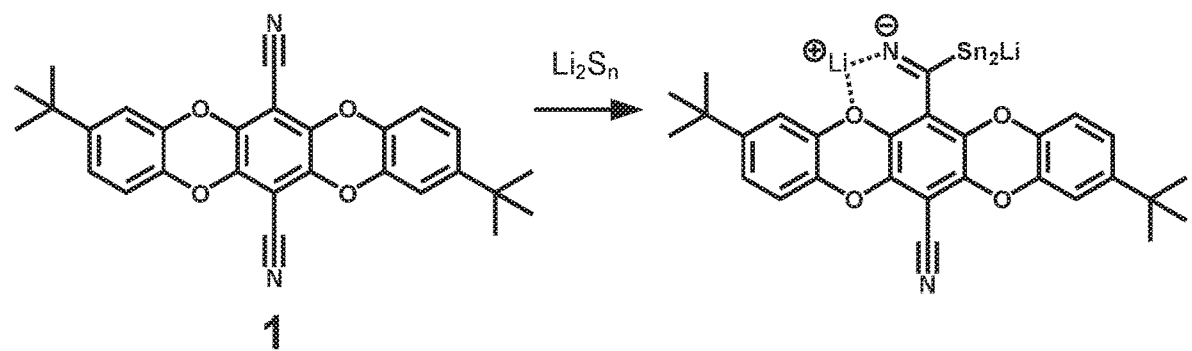
FIG. 19A provides a chemical structure of a polymer of intrinsic microporosity and a chemical structure of a modified polymer of intrinsic microporosity.

FIG. 19A: Proposed reactivity of model compound 1. FIG. 19B: Aromatic region of $^1$H NMR before (top, red) and after (bottom, blue) the addition of 20 equiv. Li$_2$S$_8$ in 1:1 THF-d$_8$:diglyme. FIG. 19C: Observed (bottom/black) and calculated (top/green) ESI-MS spectra for [1+SH]$^-$. FIG. 19D: Observed (bottom/black) and calculated (top/green) ESI-MS spectra for [1+Li$_3$S$_5$]$^-$.

FIG. 20A: Time-evolution of FT-IR spectra for PIM-1 soaked in 1.0 M S as Li$_2$S$_8$. FIG. 20B: Time-evolution of peak intensities for peaks at 2239, 2221, and 1579 cm$^{-1}$. FIG. 20C: Pore-size distribution of PIM-1 soaked in electrolyte vs. soaked in electrolyte containing 1.0 M S as Li$_2$S$_8$ for 24 h.

Materials. Diethylene glycol dimethyl ether (diglyme, anhydrous, 99.5%), 1,2-dimethoxyethane (glyme, anhydrous, 99.5%), 4-tert-butylcatechol (98%), potassium carbonate, tetrafluoroterephthalonitrile (99%), tetrahydrofuran-d8 (99.5% atom D) and 3,3,3',3'-tetramethyl-1,1'-spirobisindane-5,5',6,6'-tetraol (96%) were obtained from Sigma-Aldrich. Lithium foil (99.9%, 1.5 mm thick), lithium nitrate, lithium sulfide (99.9% metals basis), and sulfur (99.9995% metals basis) were obtained from Alfa Aesar. Lithium bis(trifluoromethanesulfonimide) (LiTFSI) was obtained from 3M. Glassy carbon electrodes with 1 mm diameter were purchased from BAS Inc. (West Lafayette, Ind.) and polished before each experiment with 3-µm diamond paste. N,N-dimethylformamide (DMF) and tetrahydrofuran (THF) were taken from a JC Meyer solvent system. Chloroform (HPLC grade) was obtained from EMD Millipore. All chemicals were used as received unless otherwise specified. Lithium nitrate and LiTFSI were dried under vacuum for 16 h at 110 and 150° C., respectively. Diglyme was dried over 3 Å molecular sieves to <20 ppm water. Electrolyte refers to 0.50 M LiTFSI and 0.15 M LiNO$_3$ in diglyme. A stock solution of 2.50 M S as Li$_2$S$_8$ was prepared by adding sulfur (701 mg, 21.9 mmol S) and lithium sulfide (144 mg, 3.1 mmol) to electrolyte (10 mL) at 60° C. The stock solution was stored at 60° C. to prevent precipitation of polysulfides and was diluted as necessary.

Instrumentation. Unless otherwise mentioned, all manipulations were performed in an argon glovebox with oxygen and water levels below 5 and 1 ppm, respectively. NMR spectra were acquired on a Bruker Avance II 500 MHz NMR spectrometer at 500 MHz for $^1$H and 125.7 MHz for $^{13}$C. $^1$H and $^{13}$C chemical shifts were referenced with respect to residual solvent peaks ($^1$H (δ) chloroform-d$_3$ 7.26, $^{13}$C (δ) chloroform-d$_3$ 77.16, $^1$H (δ) THF-d$_8$ 1.72 ppm). Polymer molecular weight was measured using size-exclusion chromatography with a Malvern Viscotek TDA 302 system calibrated with a 99 kDa monodisperse polystyrene standard. Electrochemical experiments were performed on a Bio-Logic VMP3 potentiostat. Cyclic voltammograms were acquired with iR drop compensation by measuring the uncompensated resistance with a 100 kHz impedance measurement and correcting for 85% of the expected drop. Water content measurements were performed on a Mettler Toledo C20 Coulometric KF Titrator Karl-Fischer apparatus. Nitrogen adsorption measurements were performed at liquid nitrogen temperature (~77 K) with a Micromeritics Tristar II 3020 adsorption system. In situ FT-IR spectroscopy of PIM-1 in the presence of lithium polysulfides was performed with a Mettler Toledo ReactiR 15 spectrometer. ESI-MS spectra were acquired with a Bruker microTOF-Q high-resolution mass-spectrometer.

Synthesis of PIM-1. PIM-1 with molecular weight 200 kg mol$^{-1}$ was synthesized. Briefly, a mixture of anhydrous potassium carbonate (8.3 g, 60 mmol), 3,3,3',3'-tetramethyl-1,12-spirobisindane-5,5',6,6'-tetrol (6.8 g, 20 mmol) and tetrafluoroterephthalonitrile (4.0 g, 20 mmol) in dry DMF was stirred at 65° C. for 4 d. On cooling, the mixture was added to water and the crude product collected by filtration. Repeated precipitations from a concentrated solution of polymer in chloroform into methanol yielded 8.90 g (19.3 mmol, 97% yield) of the fluorescent yellow polymer (PIM-1).

Synthesis of model compound 1. Model compound 1 was synthesized. Briefly, an oven-dried 40 mL septum-capped vial was charged with a stir bar, 4-tert-butylcatechol (997 mg, 6 mmol), tetrafluoroterephthalonitrile (600 mg, 3 mmol), and dry DMF (13 mL). The mixture was stirred for several minutes to give a transparent orange solution. Next, potassium carbonate (871 mg, 6.3 mmol) was added, and the mixture was heated to 70° C. under nitrogen for 25 h. The resulting suspension was added to 100 mL water, filtered, and rinsed with water and acetone. Finally, the product was dried at reduced pressure overnight to yield 1.306 g (2.9 mmol, 96% yield) of 1 as a bright yellow powder. $^1$H (CDCl$_3$): δ 7.03 (dd, 2H, JHH=8.2, 2.2 Hz, ArH), 7.02 (d, 2H, JHH=2.1 Hz, ArH), 6.92 (d, 2H, JHH=8.2 Hz, ArH), 1.29 (s, 18H, CH3); $^{13}$C{$^1$H} (CDCl$_3$): δ 149.9, 139.5, 139.3, 137.5, 122.5, 116.4, 114.4, 94.4, 34.8, 31.3

Figure 21A:
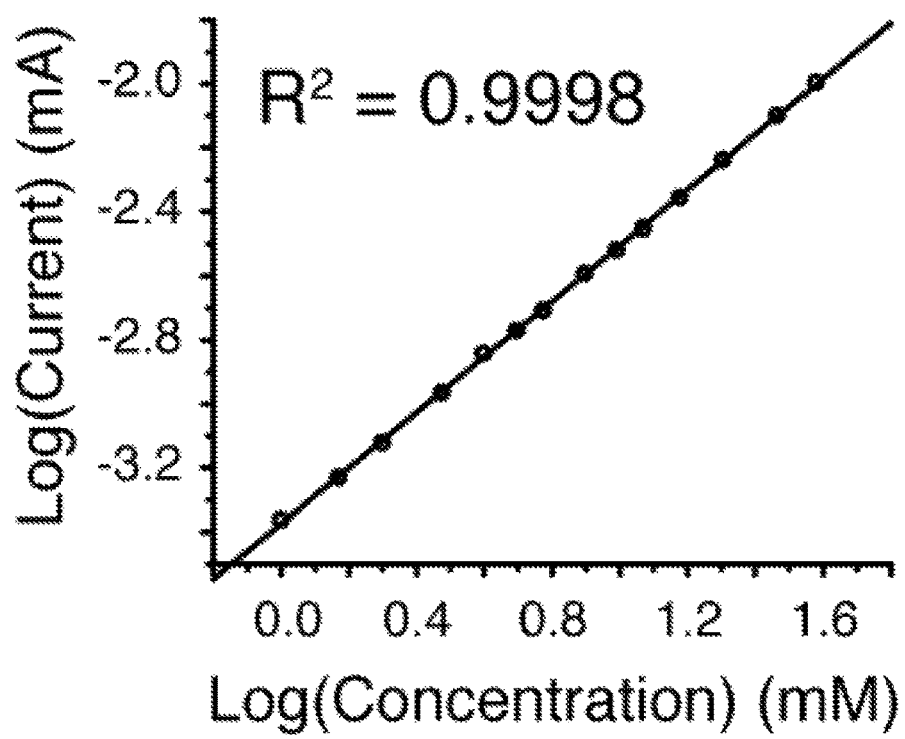
FIG. 21A provides a calibration plot of log(current) vs. log(concentration) and a fit to the data.
Figure 21B:
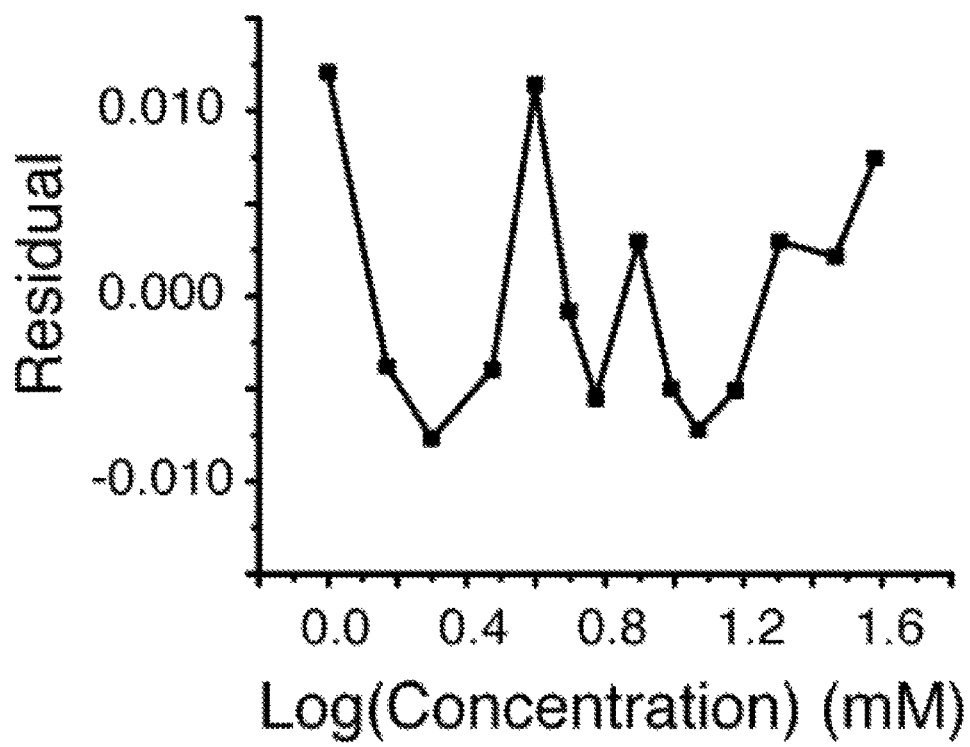
FIG. 21B provides residuals from FIG. 21A, showing that the deviations from the fit are random.
Figure 21C:
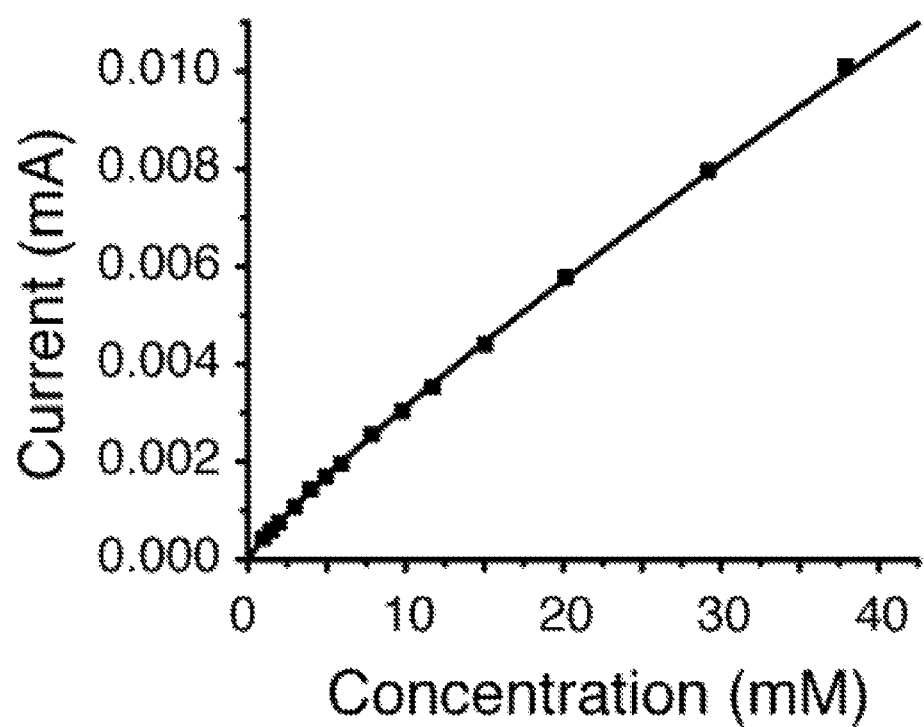
FIG. 21C provides the calibration plot of FIG. 21A on linear axes.

Crossover measurement and analysis. A PIM-1 membrane of known thickness (typically 8-12 µm) was placed between two halves of an H-cell with an aperture diameter of 1.6 cm and sealed in place with a chemically resistant O-ring. One half of the H-cell (the retentate) was charged with 12 mL of Li$_2$S$_8$ in electrolyte, while the other half (the permeate) was charged with the same volume of electrolyte with no Li$_2$S$_8$. Both compartments were stirred to ensure homogeneity. Every 20-30 min, the stirring was stopped and the concentration was measured electrochemically by acquiring a CV at 100 mV s$^{-1}$ from 2.00 V to 3.00 V vs. Li/Li$^-$. The peak anodic current was related to polysulfide concentration with a calibration curve (FIGS. 21A-C).

TABLE 1

Known concentration, calculated concentration from the calibration curve, and the percent difference for all points on the calibration curve.

| Actual Conc. (mM) | Calc. Conc. (mM) | Difference (%) |
| --- | --- | --- |
| 0.998 | 1.030 | 3.3 |
| 1.478 | 1.463 | −1.0 |
| 1.992 | 1.952 | −2.0 |
| 2.982 | 2.951 | −1.0 |
| 3.968 | 4.090 | 3.1 |
| 4.95 | 4.939 | −0.2 |
| 5.929 | 5.843 | −1.5 |
| 7.874 | 7.936 | 0.8 |
| 9.804 | 9.675 | −1.3 |
| 11.719 | 11.498 | −1.9 |
| 15.034 | 14.832 | −1.3 |
| 20.154 | 20.313 | 0.8 |
| 29.19 | 29.357 | 0.6 |
| 37.893 | 38.651 | 2.0 |

Calculation of $D_{eff}$ from crossover measurement. At any moment, the flux of active-species across the membrane (J, mol cm$^{-2}$ s$^{-1}$ can be described with Fick's first law:

$$J = D_{eff}\frac{\partial C}{\partial x} = D_{eff}\frac{C_{retentate}(t) - C_{permeate}(t)}{l},$$

where C is the concentration in mol cm$^{-3}$ and l is the membrane thickness in cm. For short times, the difference $C_{retentate}(t) - C_{permeate}(t)$ does not change significantly from its initial value of $C_{retentate}(t_0) - C_{permeate}(t_0) = C_0$, and the flux is constant with time:

$$J_{t=0} = D_{eff}\frac{C_0}{l}.$$

The concentration of active species in the permeate compartment can be calculated by integrating the flux of active species over time from 0 to t, multiplying by the membrane area, A, and dividing by the volume of solution in the permeate compartment:

$$C_{permeate}(t) = \frac{A\int_0^t J(t)dt}{V_{permeate}} = \frac{D_{eff}C_0 A}{lV_{permeate}}t.$$

By measuring active-species concentration in the retentate compartment and plotting these values as a function of time, the effective diffusion coefficient of the active-species through the membrane can be quantified.

Figure 22A:
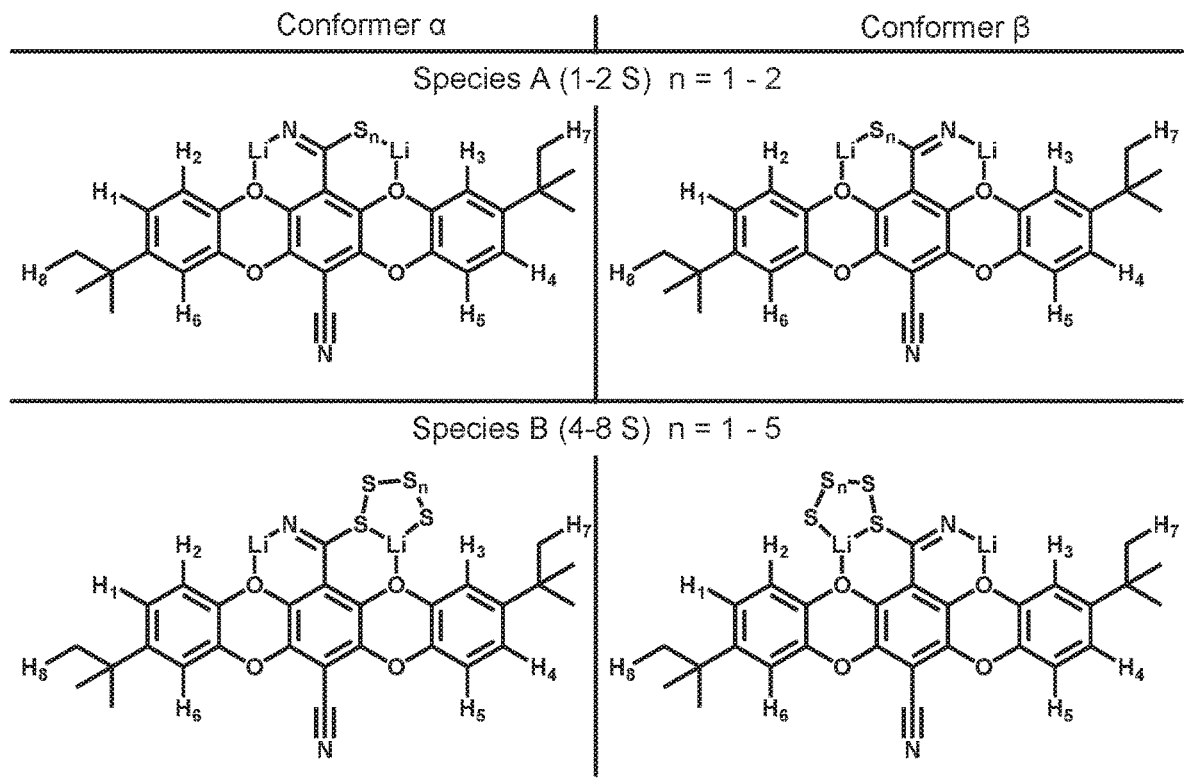
FIG. 22A provides different proposed chemical structures and conformers for modified polymers of intrinsic microporosity.
Figure 22B:
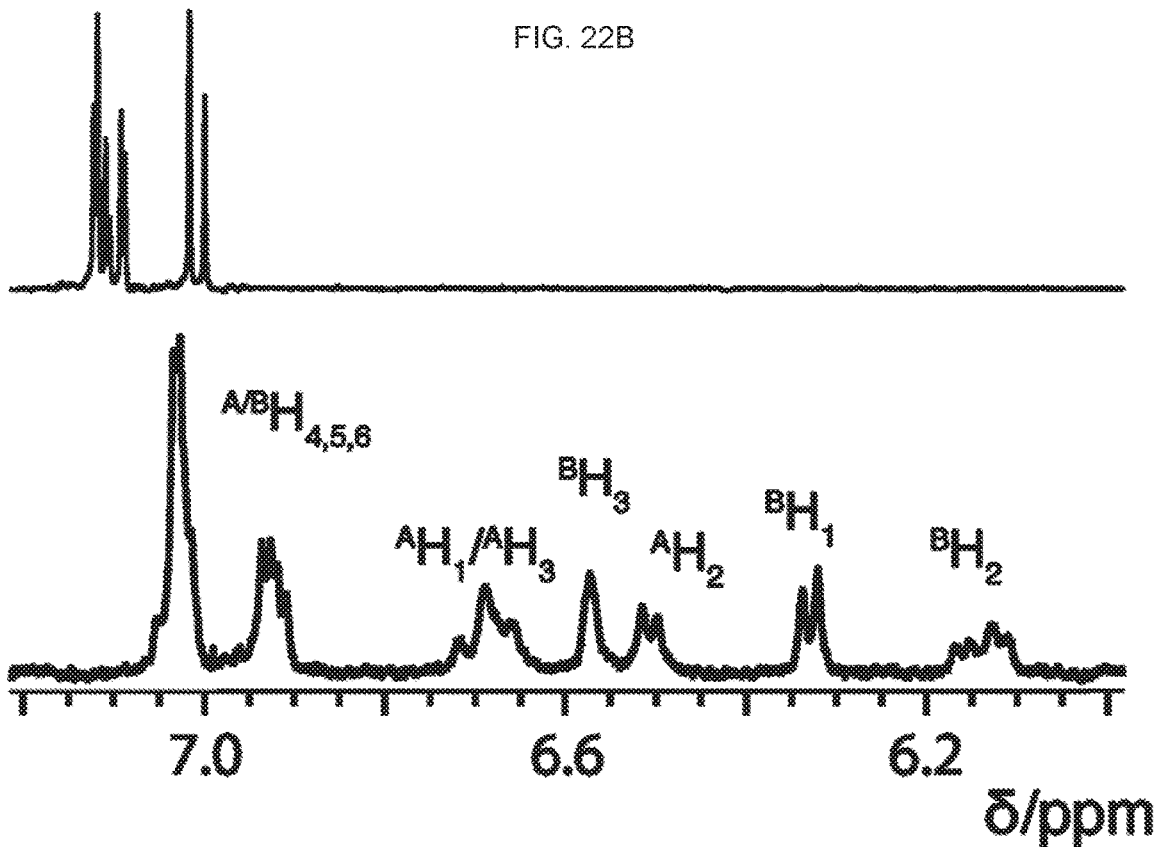
FIG. 22B provides data showing a portion of observed NMR spectra.

Characterization of reacted model compound. Assignment of $^1$H-NMR of reacted model compound. Solutions of lithium polysulfides are may contain numerous species. Therefore, a number of lithiated thioamides may result from the reaction of model compound 1 with $Li_2S_8$. The aliphatic region of the $^1$H NMR spectrum of 1+20 $Li_2S_8$ has one sharp singlet at 1.28 ppm and three broad singlets at 1.21, 1.13, and 0.97 ppm with relative integration of the sharp singlets to broad singlets of 1:1. The sharp singlet, which is within 0.02 ppm of the unreacted compound resonance, is attributable to tert-butyl groups on the opposite side of the molecule from the reacted nitrile group (FIG. 22A, proton 8). The broad peaks correspond to tert-butyl groups close to the reacted nitrile, and can be assigned to two separate species: one where the rotation around the C—CN bond is unhindered, and another where the rotation is hindered. It was hypothesize that for lithiated thioamides containing more than 3 sulfur atoms (species B in FIG. 22A), the unbound terminal sulfur atom can chelate lithium along with the neighboring oxygen, thus hindering rotation about the C—CN bond. As a result, the protons from the tert-butyl groups in the α and β conformers are chemically distinct, with peaks at 1.21 and 0.97 ppm. As temperature was increased to 55° C. (FIGS. 23A-23B), these peaks broadened as is typical before coalescence, which supports this assignment. On the other hand, lithiated thioamides with fewer sulfur atoms cannot chelate lithium in the same way, and so they have less hindered rotation about the C—CN bond, leading to one broad peak at 1.13 ppm for the signal average between the α and β conformers. As expected, this peak did not broaden as temperature is increased. The multiplets from 7.1 to 6.9 ppm are similar in chemical shift to the multiplets in the unreacted model compound and can be assigned to protons 4, 5, and 6. This is further supported by the relative integration of the peaks, with the multiplets from 7.1 to 6.9 ppm having a relative integration of 3, equivalent to the total integral from 6.8 to 6.1 ppm. The remaining peaks were readily assigned on the basis of $^1$H-COSY and integration data. $H_3$ protons were assigned based on the absence of o-coupling and the absence of $^1$H-COSY cross-peaks, with the upfield peak assigned to the more shielded proton of species B. Pairs of multiplets corresponding to $H_1$ and $H_2$ were assigned based on $^1$H-COSY cross-peaks, with the upfield pair assigned to species B and the more upfield of each pair of multiplets assigned to proton 2.

ESI-MS of reacted model compound. An 8 mM solution of 1 in 1:1 diglyme:THF-$d_8$ was treated with 20 equivalents of $Li_2S_8$ in the same solvent mixture. After 10 days mixing to ensure complete equilibration, the solution was diluted to $8 \times 10^{-6}$ M in 1. To avoid contamination/decomposition of the reacted model compound with water and oxygen, the syringe and capillary of the ESI-MS instrument were purged with dry, air-free THF immediately prior to analysis of the model compound with polysulfide. The ESI-MS was operated in negative mode with an injection rate of 5 μL/min.

Characterization of reacted PIM-1. FT-IR of PIM-1 in the presence of lithium polysulfides. PIM-1 was dropcast onto the polished silicon ATR probe of the spectrometer from a 12.5 mg mL$^{-1}$ solution in chloroform, which was dipped into electrolyte blanketed under nitrogen. A stock solution of $Li_2S_8$ in electrolyte was injected to yield a sulfur concentration of 1.0 M or 0.2 M, as appropriate. The resulting solution was stirred under nitrogen and spectra were acquired every 5 min. Peak heights as shown in FIG. 27 were measured from a 2-point baseline.

Gas adsorption measurements of PIM-1. PIM-1 was soaked in electrolyte or electrolyte containing 1.0 M S as $Li_2S_8$ for 24 h, followed by washing with and soaking in diglyme for a total of 26 h. Finally, the membranes were washed with glyme, dried under vacuum at room temperature for 70 h, and dried under vacuum at 120° C. for 19 h before measurement.

Figure Captions. FIG. 21A: Calibration plot of log(current) vs. log(concentration) with the linear regression. FIG.

21B: Residuals from FIG. 21A, showing that the deviations from the fit are random. FIG. 21C: The calibration plot of FIG. 21A on linear axes.

Figure 22C:
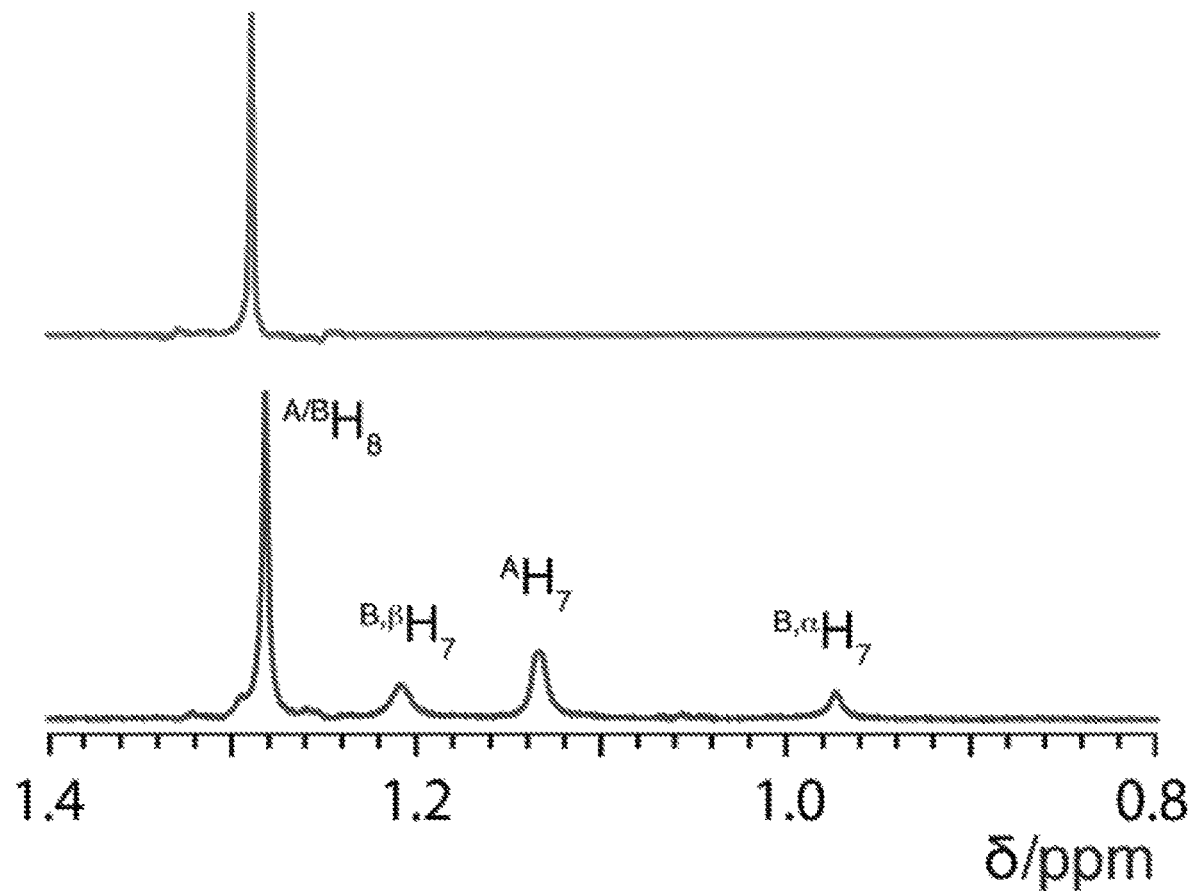
FIG. 22C provides data showing a portion of observed NMR spectra.

FIG. 22A: Proposed chemical structure of model compound 1 after reaction with lithium polysulfides, FIG. 22B: Aromatic region of the $^1$H-NMR of model compound 1 before (red, top) and after (blue, bottom) reaction with 20 equiv. $Li_2S_8$ with peak assignments. FIG. 22C: Aliphatic region of the $^1$H-NMR of model compound 1 before (red, top) and after (blue, bottom) reaction with 20 equiv. $Li_2S_8$ with peak assignments.

Figure 23A:
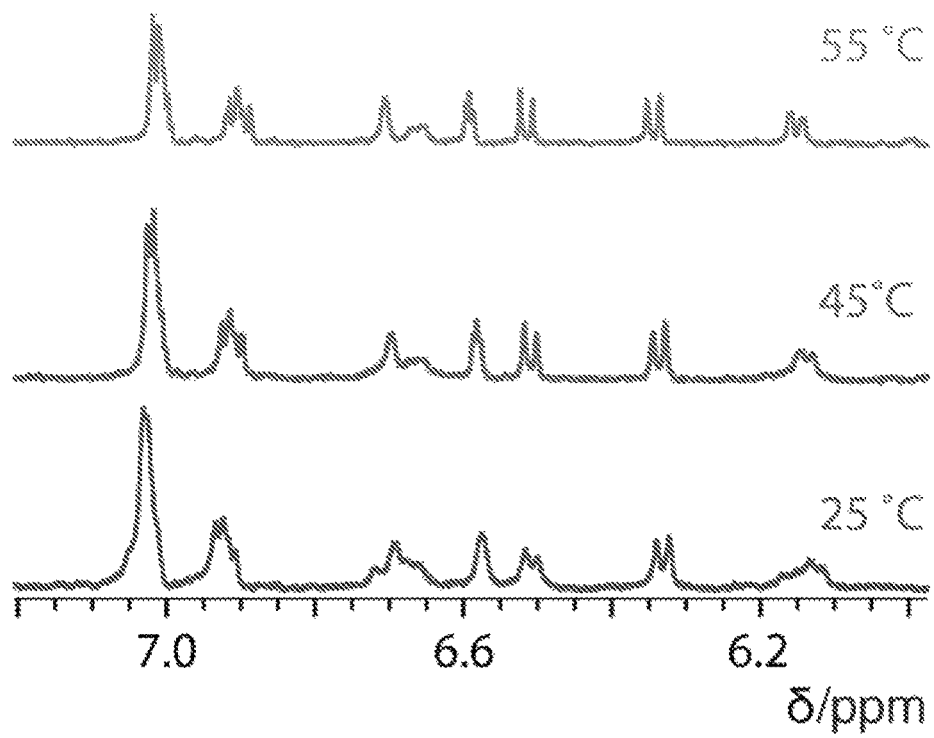
FIG. 23A provides data showing a portion of observed NMR spectra for three different temperatures.
Figure 23B:
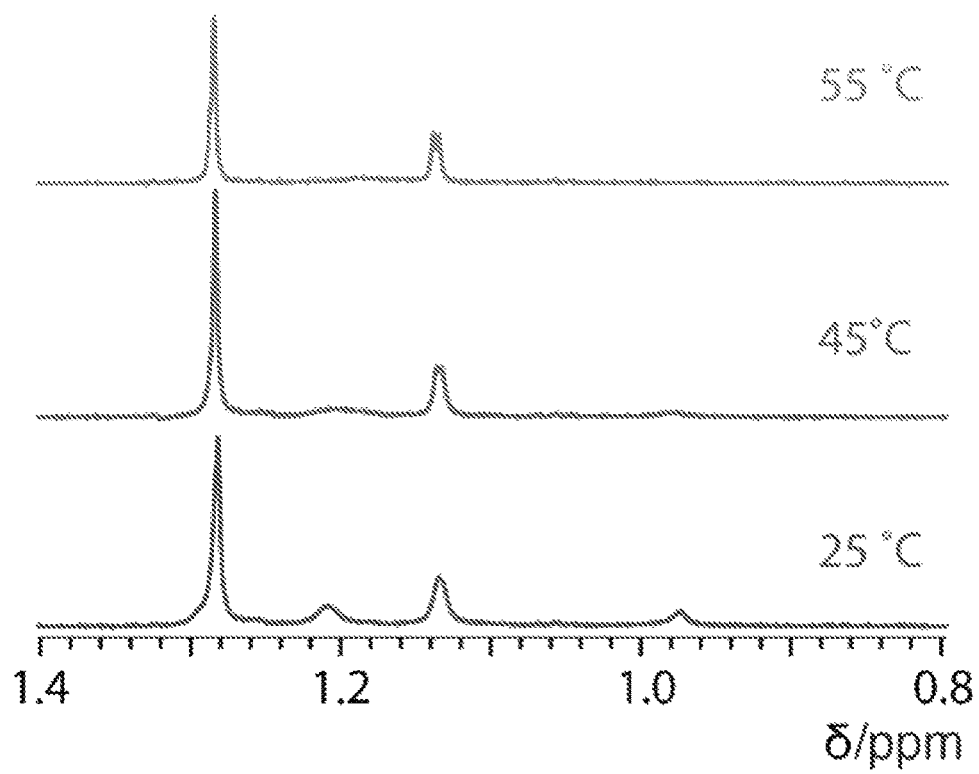
FIG. 23B provides data showing a portion of observed NMR spectra for three different temperatures.

FIG. 23A: Variable temperature $^1$H-NMR of model compound 1+20 equiv. $Li_2S_8$ at 25, 45, and 55° C. for the aromatic region of the spectrum. FIG. 23B: Variable temperature $^1$H-NMR of model compound 1+20 equiv. $Li_2S_8$ at 25, 45, and 55° C. for the aliphatic region of the spectrum.

Figure 24:
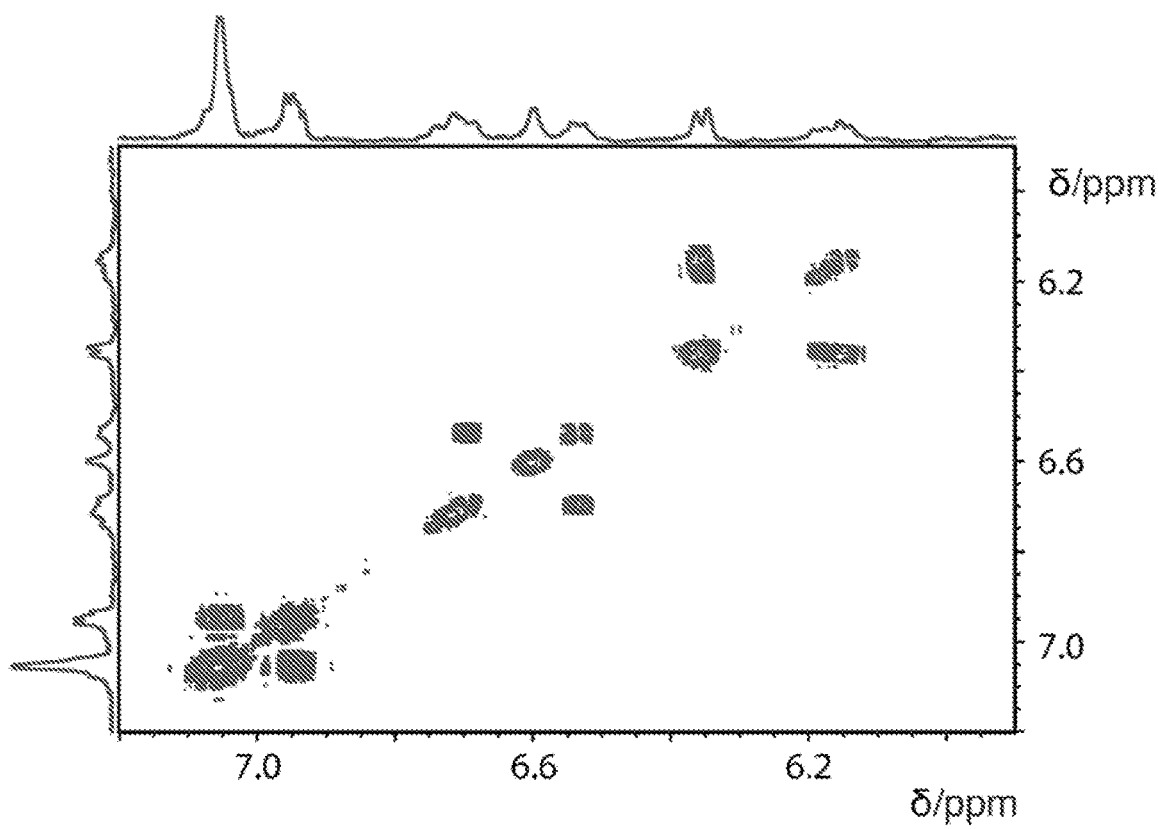
FIG. 24 provides a 2D NMR spectrum.

FIG. 24: $^1$H-COSY of model compound 1+20 equiv. $Li_2S_8$.

Figure 25:
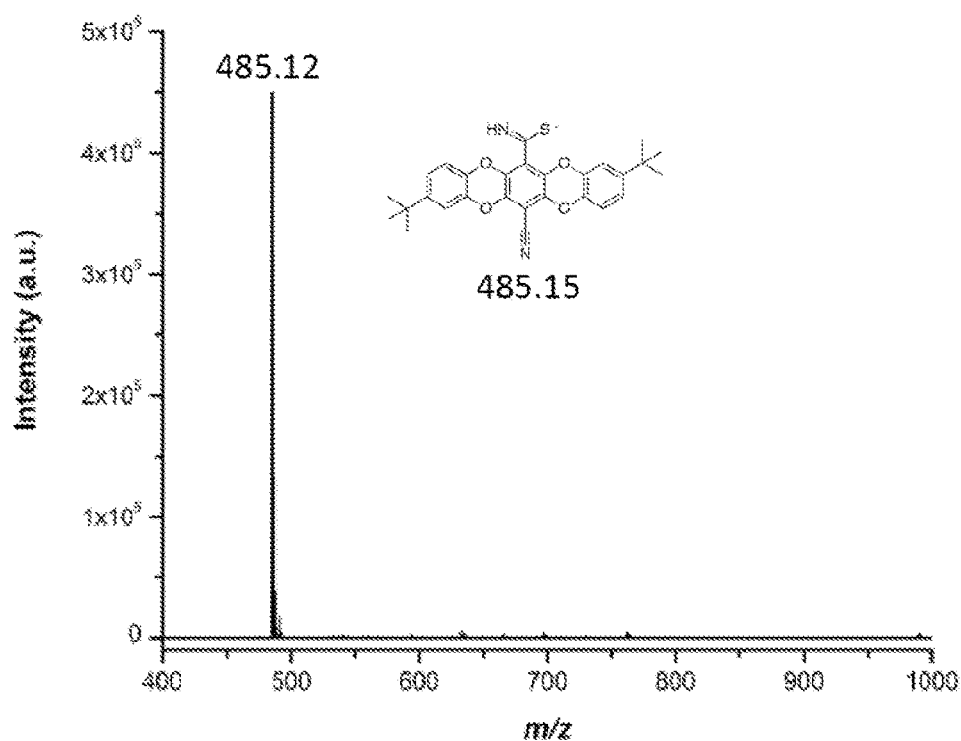
FIG. 25 provides data showing an electrospray ionization mass spectrum.

FIG. 25: ESI-MS showing the most intense peak assigned to $[M+SH]^-$.

Figure 26:
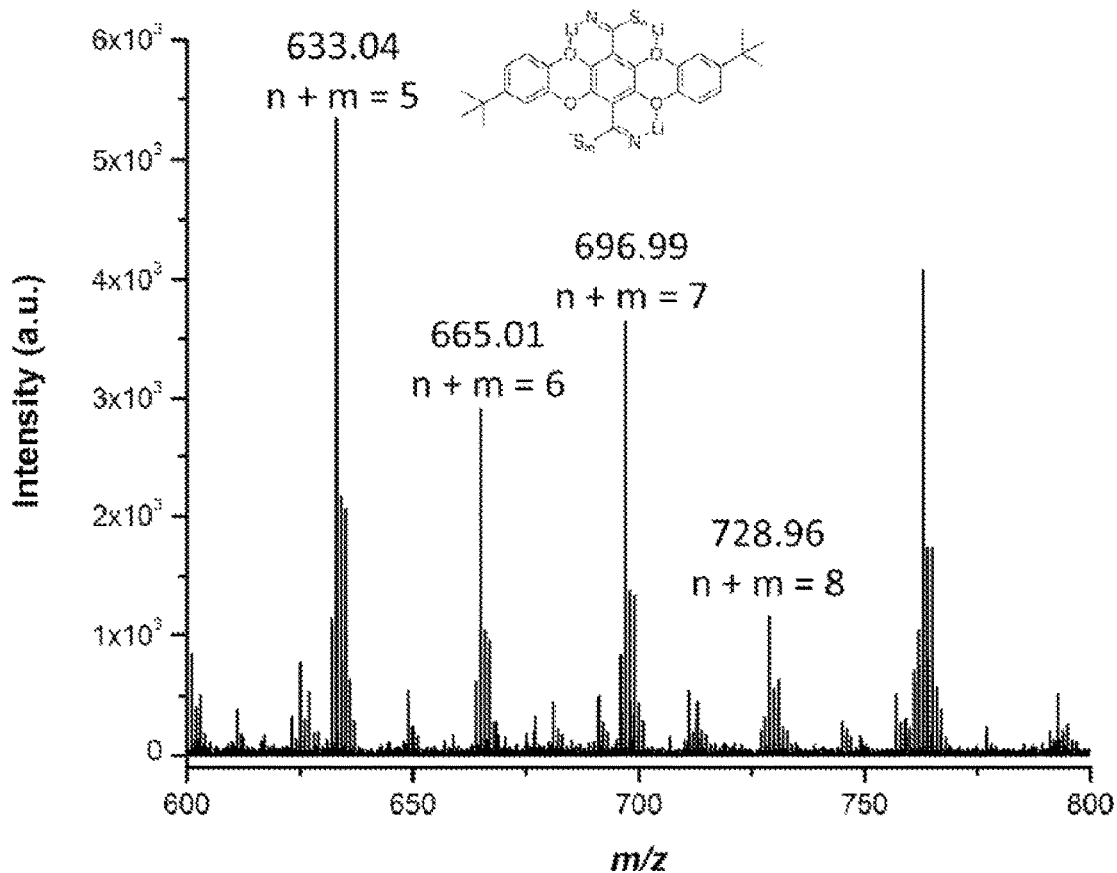
FIG. 26 provides data showing an expanded view of the electrospray ionization mass spectrum of FIG. 25.

FIG. 26: Lower intensity region from FIG. 25 highlighting peaks attributed to both nitrile groups of the model compound reacting with polysulfide. Isotopic distributions for all assigned peaks are similarly well matched to those displayed above.

FIG. 27: FT-IR of PIM-1 after soaking in 1.0 M S as $Li_2S_8$ in electrolyte for 22.5 h (black) and after replacing the $Li_2S_8$ solution with fresh electrolyte and soaking for an additional 8.5 h (violet).

FIG. 28: Normalized intensity of the nitrile stretch at 2239 $cm^{-1}$ of PIM-1 in the presence of 0.2 M (black) and 1.0 M (red) S as $Li_2S_8$.

Figure 29A:
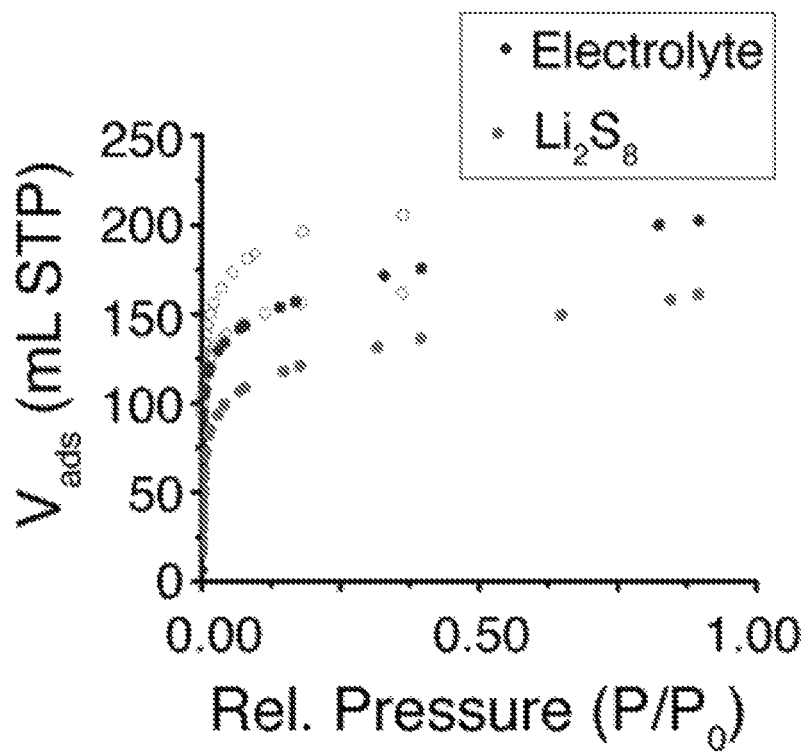
FIG. 29A provides data showing adsorption and desorption isotherms for a polymer of intrinsic microporosity and a modified polymer of intrinsic microporosity.
Figure 29B:
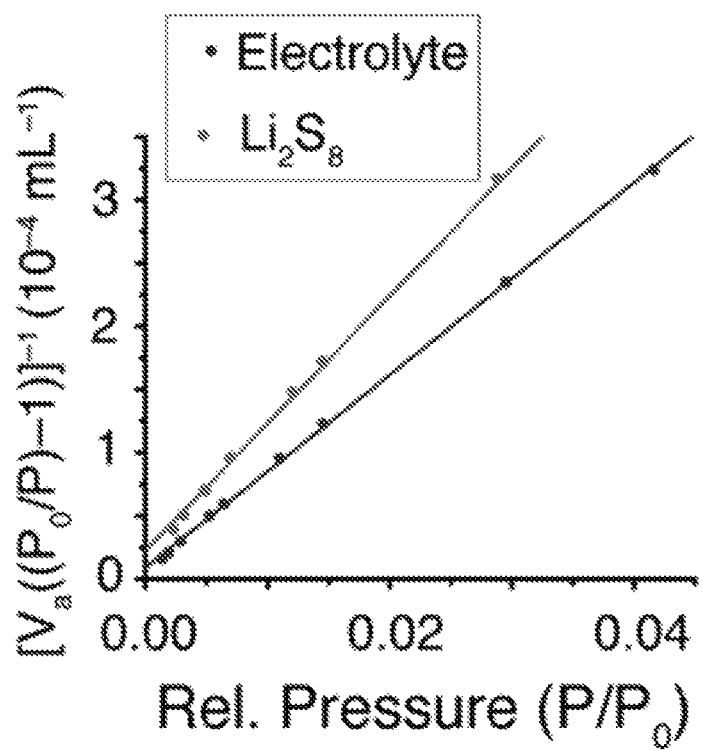
FIG. 29B provides data showing surface area analysis for a polymer of intrinsic microporosity and a modified polymer of intrinsic microporosity.
Figure 29C:
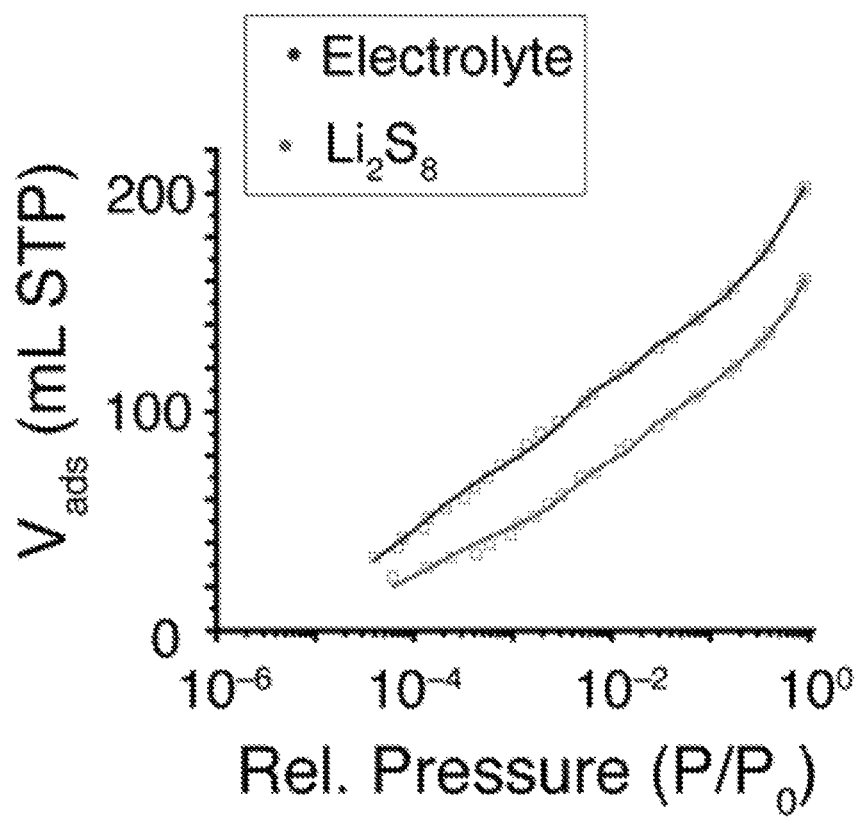
FIG. 29C provides data showing simulated and observed isotherms for a polymer of intrinsic microporosity and a modified polymer of intrinsic microporosity.

FIG. 29A: Adsorption (filled circles) and desorption (hollow circles) isotherms. FIG. 29B: BET surface area analysis for PIM-1 soaked in electrolyte (blue) and electrolyte containing 1.0 M S as $Li_2S_8$ (red). FIG. 29C: Simulated NLDFT adsorption isotherms (lines) with experimental isotherms (points) for PIM-1 soaked in electrolyte (blue) and electrolyte containing 1.0 M S as $Li_2 S_8$ (red).

Example 3. Redox-Switchable Microporous Polymer Membranes that Extend the Cycle-Life of Lithium-Sulfur Batteries In biological systems, selective transport of ions across membranes is achieved by transmembrane proteins. Ion flux is subject to strict regulation and the cell's environment plays a dominant role. Perturbations to that environment—whether physical, chemical, or electrical—are met with an adaptive response, which is tied to changes in the proteins' transport functions. This example applies this concept of adaptive transport across ion-selective membranes to improve the cycle-life of lithium-sulfur (Li—S) batteries. Li—S batteries are inherently unstable when soluble polysulfides in the cathode crossover the membrane and react with the lithium-metal anode. This Example shows that certain types of redox-switchable microporous polymer membranes can be made to enhance their selectivity for the battery's working ion when they encounter the battery's endogenous polysulfides and that these functions are sustained. The origins and implications of this behavior are explored in detail and point to new opportunities in responsive membranes.

Membrane separators play a critical role in many battery technologies, where they serve to electronically isolate the anode from the cathode while allowing the working ion to diffuse between them. For battery chemistries that involve dissolved, dispersed, or suspended active materials, membrane separators must also prevent active-material crossover; failure to do so leads to low round-trip energy efficiency and in some cases unacceptable capacity fade. This is particularly problematic in lithium-sulfur (Li—S) batteries, where inefficiencies and instabilities arise when soluble polysulfides—intermediates in the electrochemical interconversion of $S_8$ and $Li_2S$—crossover and incur a shuttling current or otherwise react with the lithium-metal anode.

This Example shows that these shortcomings are alleviated in the Li—S battery when its membrane separator is configured rationally from redox-switchable polymers of intrinsic microporosity (PIMs). Advantages may be achieved for adaptive transport selectivity for the working ion, which productively leverages the reducing environment of the sulfur cathode to chemically transform a charge-neutral size-selective PIM membrane into a lithiated PIM membrane with enhanced polysulfide-rejecting properties. The design of these new adaptive PIM membranes was navigated computationally, where putative monomer segments were screened for their susceptibility to reduction by polysulfides (i.e., an electron affinity above 2.5 V vs $Li/Li^+$). Those predictions were experimentally validated to demonstrate that progressive reduction and lithiation of the PIM membrane by polysulfides slows polysulfide diffusive permeability from—providing an impressive improvement over non-selective Celgard separators—without impacting the intrinsic ionic conductivity for solvated lithium ions. This Example also shows that by blocking polysulfide crossover, cycle-life of Li—S cells markedly improve—most notably in the absence of lithium-anode protecting additives. The stability of the lithium anode under these conditions is unprecedented, and highlights the unexpected and exciting new opportunities afforded by responsive redox-active polymers and ultimately adaptive membranes in battery technology development.

Design strategies for a membrane that offers selectivity may make use of two mechanisms: size-sieving and electrostatic charge-blocking. Guided by theoretical calculations to target a specific turn-on voltage for electrostatic charge-blocking, redox active moieties capable of in situ reduction were selected. These were then incorporated into a polymer of intrinsic microporosity (PIM-7), a class of polymer well known for size sieving by virtue of its permanent microporous architecture. During battery operation, these redox-active groups become charged, leading to charge selectivity. Using lithium-sulfur batteries as a model chemistry to probe in operando activated membrane selectivity, the PIM-7 platform was tested in lithium-sulfur cells for its ability to block polysulfide crossover and shuttling at the anode. The redox activity of the polymer at 3.0 V vs. $Li/Li^+$ was confirmed via electrochemical reduction (CV), and chemical reduction of PIM-7 by $Li_2S$ was monitored with UV-Vis. Synergistic size-sieving and charge repulsion of polysulfide was evident in the crossover behavior and lithium-sulfur cell performance where the hybrid charge and size selective PIM-7 membrane vastly outperforms that of a commercial separator as well as a PIM membrane capable of size exclusion alone.

Figure 31:
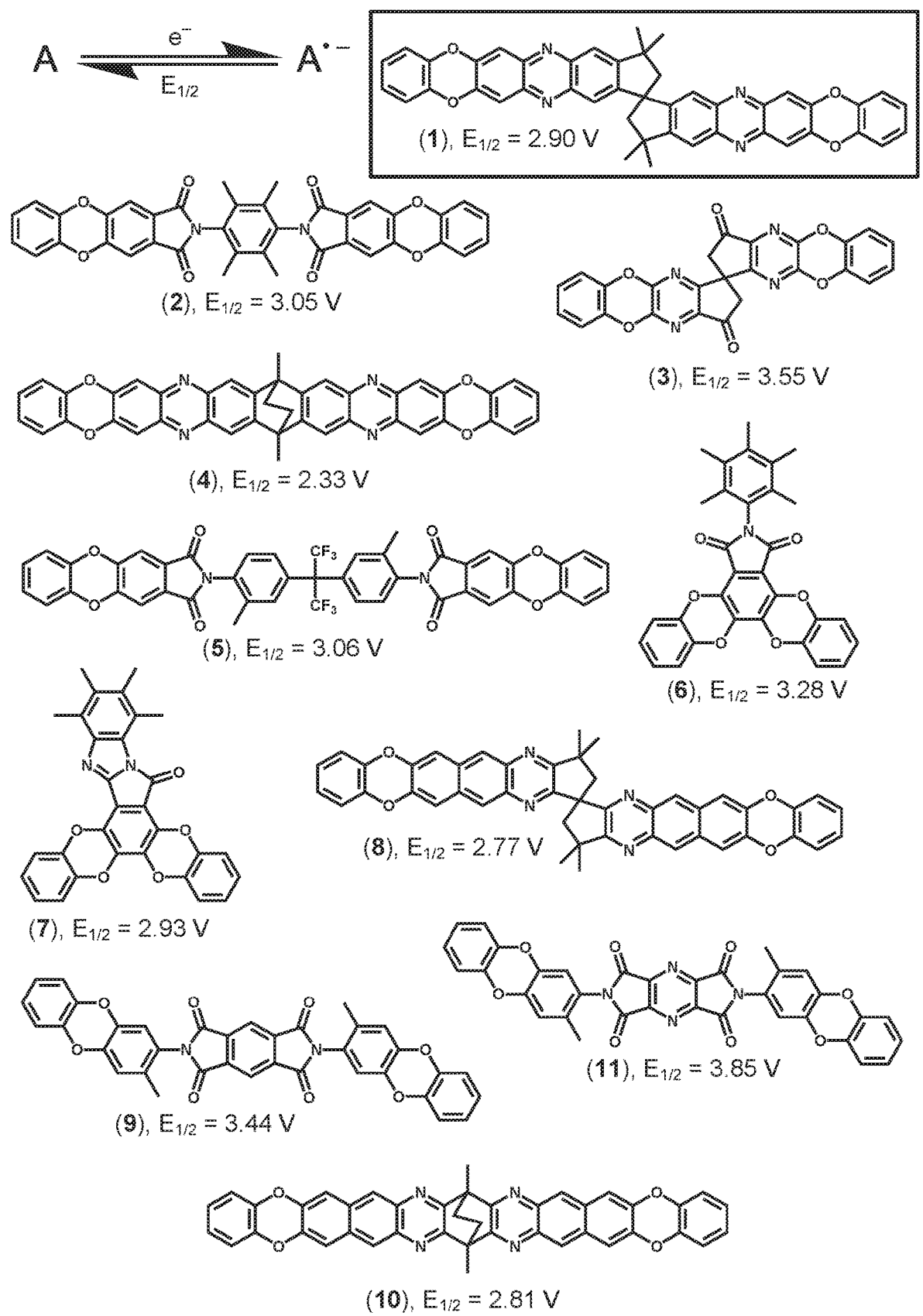
FIG. 31 provides example monomer structures for polymers of intrinsic microporosity and their calculated reduction potentials.

Given the synthetic versatility of the PIM platform, many monomers containing redox active units are available. To help guide the selection, theoretical calculations were used to facilitate determining a monomer with a compatible reduction potential for a Li—S battery. From a library of model compounds it was found that a class of phenazine containing monomers had redox potentials well suited to be reduced in the Li—S battery (FIG. 31). In particular, PIM-7 was selected due to its ideal combination of redox potential (calculated: 2.90 V vs. Li/Li$^+$), synthetic accessibility and membrane processability. PIM-7 was synthesized (80 kg mol$^{-1}$) via step growth polymerization between a phenazyl-based bis(dichloro) monomer and the seminal spirobisindane bis(catechol). In order to utilize thinner membranes for higher ion flux without sacrificing mechanical stability, PIM-7 membranes were cast onto a Celgard support using wire wound rod processing. This method afforded 2 μm thick uniform coatings of PIM-7 as evidenced by cross-sectional SEM. PIM-7 has a reported BET specific surface area (680 m$^2$ g$^{-1}$) and a pore size of 0.70 nm, which is ideal for selective transport of LiTFSI and PS blocking. PIM-7 has a built in redox-switchable moiety that, in accordance with calculations, is capable of providing in operando charge blocking, while also possessing features that result in size sieving.

Figure 32A:
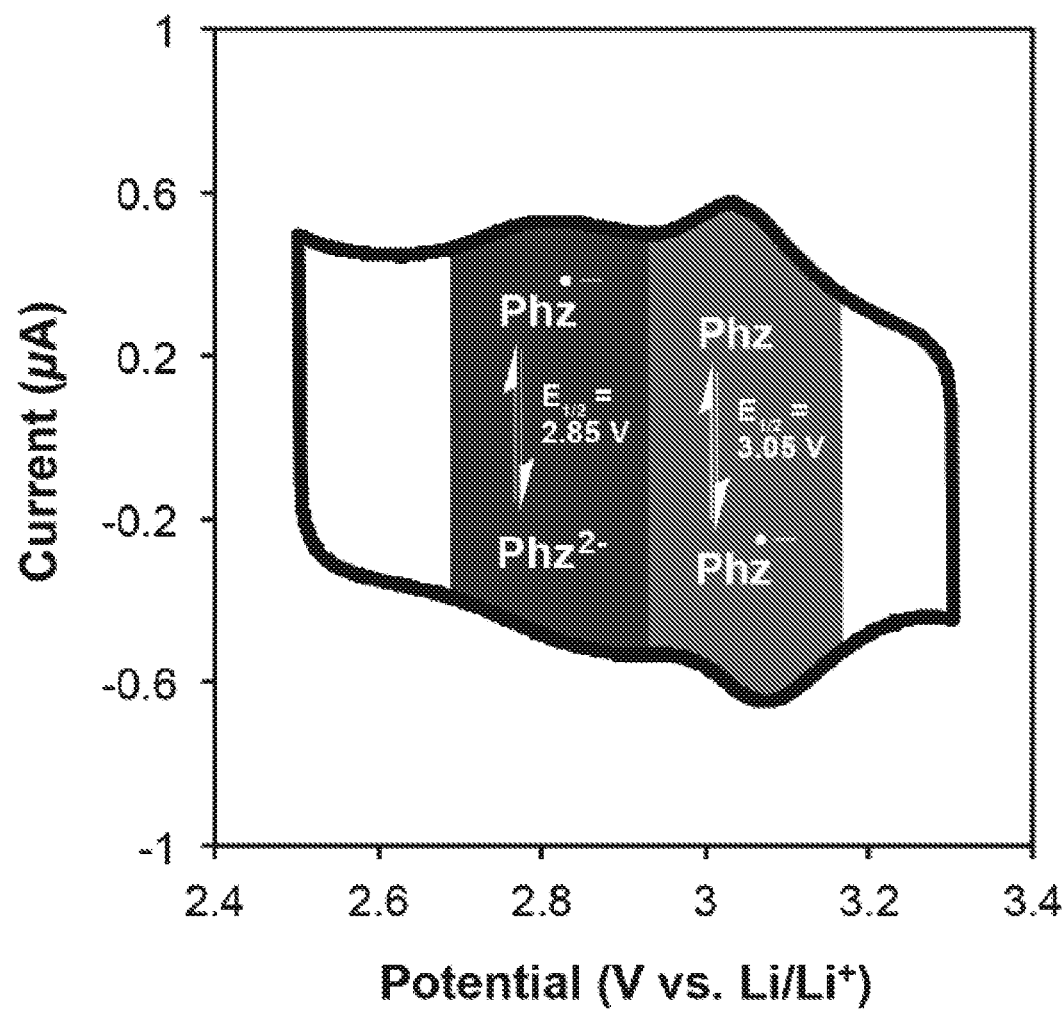
FIG. 32A provides a cyclic voltammogram of an example polymer of intrinsic microporosity.
Figure 32B:
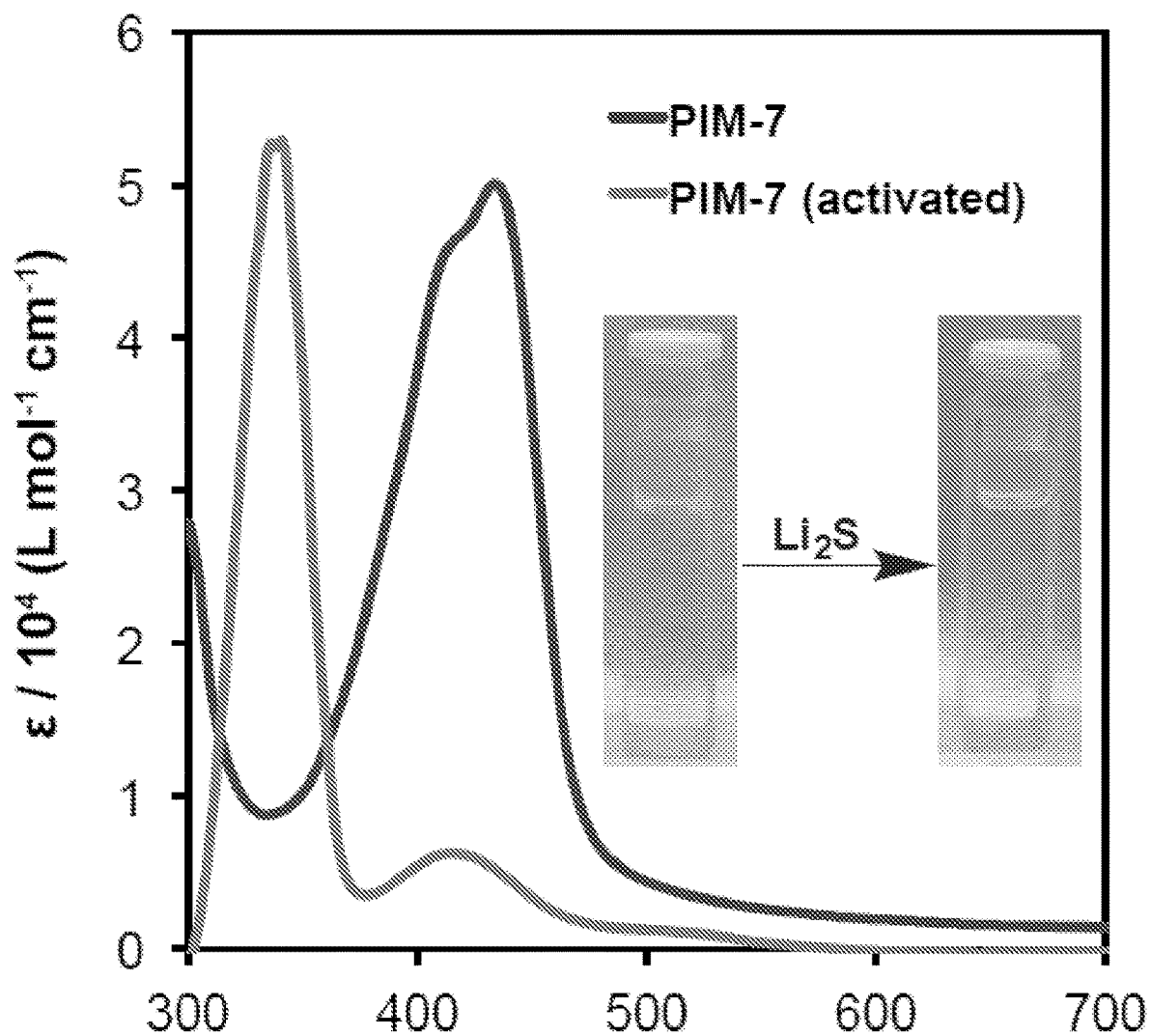
FIG. 32B ultraviolet/visible spectra of a polymer of intrinsic microporosity and a modified polymer of intrinsic microporosity.

In order to experimentally validate the calculated reduction potential of PIM-7, cyclic voltammetry (CV) was carried out on the polymer drop cast onto a glassy carbon working electrode (FIG. 32A). PIM-7 showed two reversible reduction peaks at $E_{1/2}$=3.05 and 2.85 V vs. Li/Li$^+$, which can be attributed to the reduction of the phenazine group to the radical anion followed by the reduction to the dianionic species. To further verify this result, PIM-7 was chemically reduced via reaction with Li$_2$S, where reduction is indicated via a shift to lower energies (from 440 to 340 nm) in the UV-Vis (FIG. 32B). These results indicate that the PIM-7 membrane will be negatively charged in the reducing environment of the Li—S battery, both chemically by components of the catholyte, and electrochemically by contact with the cathode current collector. This redox switchable design is advantageous because by casting the polymer in its neutral state, common pitfalls associated with the processing of charged materials, such as solubility and mechanical stability, are avoided. The membrane can then be redox activated once in the cell to afford polysulfide blocking via charge repulsion.

Figure 33A:
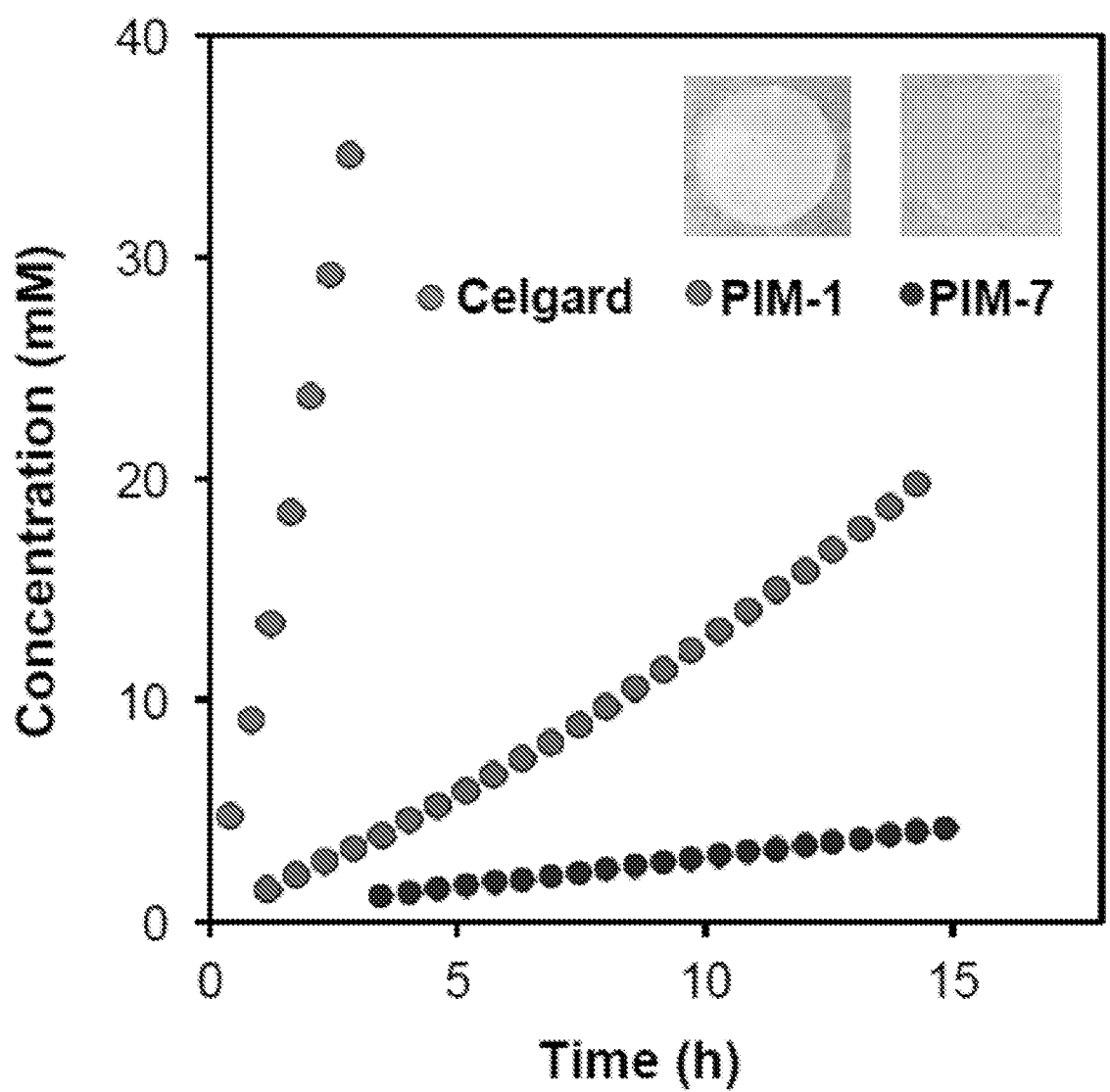
FIG. 33A provides data showing time-evolution of concentration of a polysulfide in a solution where the polysulfide is transported across different membranes.
Figure 33B:
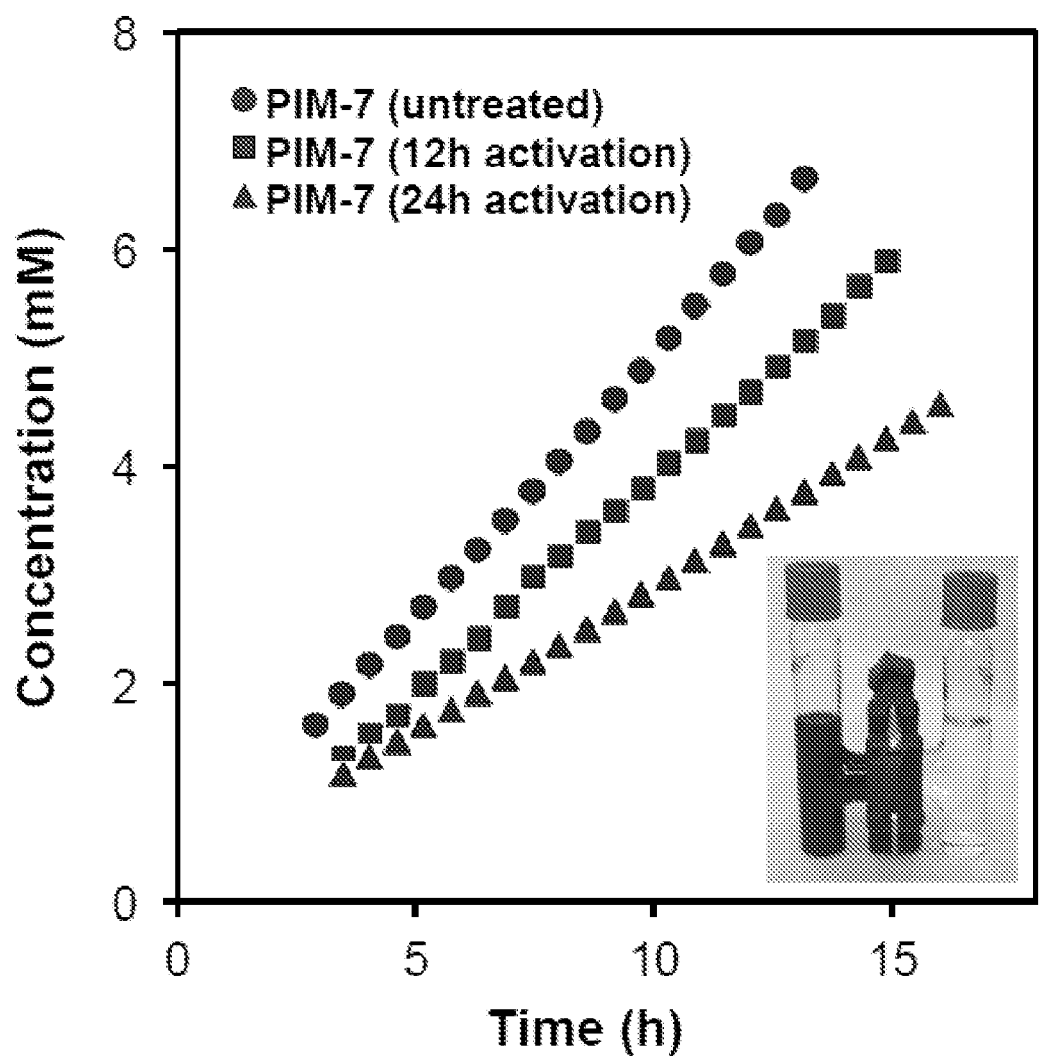
FIG. 33B provides data showing time-evolution of concentration of a polysulfide in a solution where the polysulfide is transported across different membranes.

After confirming the redox switching behavior of the PIM-7 membrane, the effect that embedded charged moieties had on the ability to mitigate the polysulfide shuttle was examined. Active species crossover measurements were obtained using supported PIM membranes of a known area and thickness placed between two chambers of an H-cell. The H-cell is configured with dissolved PS (0.8 M S as Li$_2$S$_8$ in diglyme containing 0.50 M LiTFSI and 0.15 M LiNO$_3$) on the retentate side and PS-free electrolyte on the permeate side (FIG. 33A, inset). The evolution of PS on the permeate side is then monitored over time using cyclic voltammetry, as the peak current can be directly related to the concentration via a calibration curve. Using an initial rate approximation, the diffusion coefficient of PS was calculated to be 6.2×10$^{-8}$ cm$^2$/s for Celgard, 7.1×10$^{-9}$ cm$^2$/s for PIM-1, and 1.5×10$^{-9}$ cm$^2$/s for PIM-7. The 2 μm PIM-1 blocking layer provides approximately a 5 fold reduction in the crossover of PS and the PIM-7 enhances this blocking ability by 40 fold (FIG. 33A). Additionally, if supported PIM-7 membranes are systematically reduced prior to conducting crossover measurements (0, 12, and 24 h, respectively) enhanced blocking ability is observed for membranes that have been in a reducing environment for longer times (FIG. 33B). This effect may be attributable to slow diffusion of polysulfide through the membrane and the positive feedback loop of reduced membrane further retarding the migration of polysulfide. Pre-reduction treatment past 24 h does not appear to enhance blocking. Furthermore, the supported PIM-7 also demonstrates a crossover rate that is stable over an extended period (2 d) without showing any degradation, unlike the PIM-1 which reacts with polysulfides over time and results in greater crossover. Likewise, the change in membrane ionic conductivity upon soaking for 0, 12, and 24 h in polysulfides was measured and it was found that, unlike the PIM-1, the impedance remained constant. This suggests that an additional selectivity mechanism may be available in situ without sacrificing conductivity. These crossover measurements support the idea that a hybrid membrane capable of both charge blocking and size sieving has been achieved without sacrificing ion flux, and that the design strategy described herein is advantageous for the long-term stability of the membrane.

Figure 34:
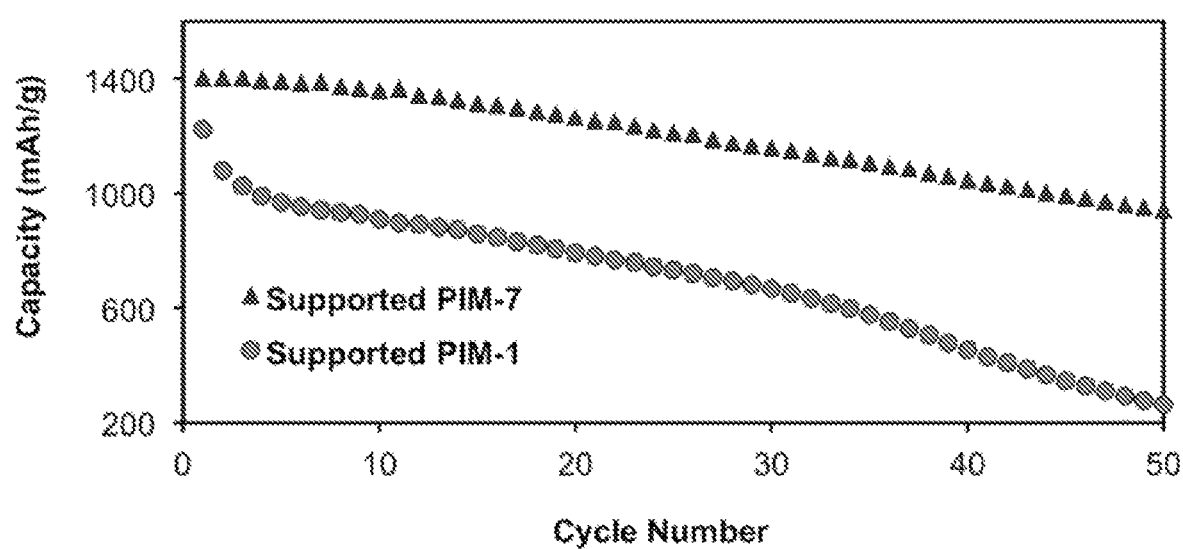
FIG. 34 provides discharge capacity vs. cycle number for two different electrochemical cells.

In order to highlight the utility of a hybrid size and charge-selective membrane, the performance of PIM-7 membranes was tested in energy dense Li—S batteries. Li—S cells were constructed using Swagelok cells comprised of a lithium anode and polysulfide catholyte (0.5 M S as Li$_2$S$_8$ in diglyme containing 0.50 M LiTFSI and 5 wt % Ketjenblack) separated by a supported PIM-7 membrane. The standard anode protecting additive LiNO$_3$ was intentionally omitted from the catholyte formulation in order to more directly assess the influence of each membrane in mitigating the polysulfide shuttle. Analogous cells with Celgard and PIM-1 membranes were constructed for comparison with all cells cycling at a rate of C/4 for 50 cycles. The Li—S cells containing the Celgard separator initially exhibit capacities comparable to that of the cells containing PIM-1 and PIM-7 membranes, however, after 5-10 cycles the cells failed due to failure to reach the charging cutoff voltage as a result of unrestrained polysulfide shuttling ultimately leading to cell failure was observed. Cells containing the PIM-1 membrane were able to sustain capacities of 300 mAh/g over 50 cycles, comparable to the results demonstrated in the above Examples. In accordance with the superior blocking ability of the PIM-7 seen in the crossover measurements, cells constructed with the PIM-7 membrane displayed vastly improved performance over that of the Celgard and PIM-1. The PIM-7 membrane cells were able to sustain capacities of 900 mAh/g over 50 cycles (FIG. 34). Additionally the cells constructed with PIM-7 displayed higher Coulombic efficiencies as compared with both Celgard and PIM-1. The rate capability of the PIM-7 membrane was assessed by cycling at C/4, C/2 and C in sequence. Even at the high 1 C rate, the cells had capacities indicating that the ionic conductivity of these membranes is sufficient for higher charge densities. These results represent an improvement over related Li—S work and demonstrate the potential for a hybrid membrane material to improve selectivity via a secondary mechanism.

The design strategies for membrane materials for electrochemical devices have reached an impasse: it is difficult to control the selective transport properties of the membrane without negatively impacting membrane conductivity. To address this bottleneck a membrane material capable of selectivity by virtue of two mechanisms has been designed, synthesized, and processed. The key design feature is the incorporation of a redox active moiety, chosen via a predictive materials genome to be reduced in situ in the Li—S battery, into the backbone of the PIM. This hybrid approach provides a charge repulsion blocking mechanism while still preserving the structural features that lead to size-sieving. This results in a marked improvement in crossover performance of the PIM-7 when compared to the PIM-1 membrane, without dramatically sacrificing membrane impedance. Additionally, the PIM-7 membranes displayed better performance in capacity, cycle life and Coulombic efficiencies when utilized in Li—S batteries. Membranes can now be tuned for pore size as well as pore chemistry. Using the predictive genome, it is straightforward to use this hybrid approach to selectivity to tailor both the size and charge of the PIM pores to suit the transport property needs of a multitude of energy storage devices.

Figure 30:
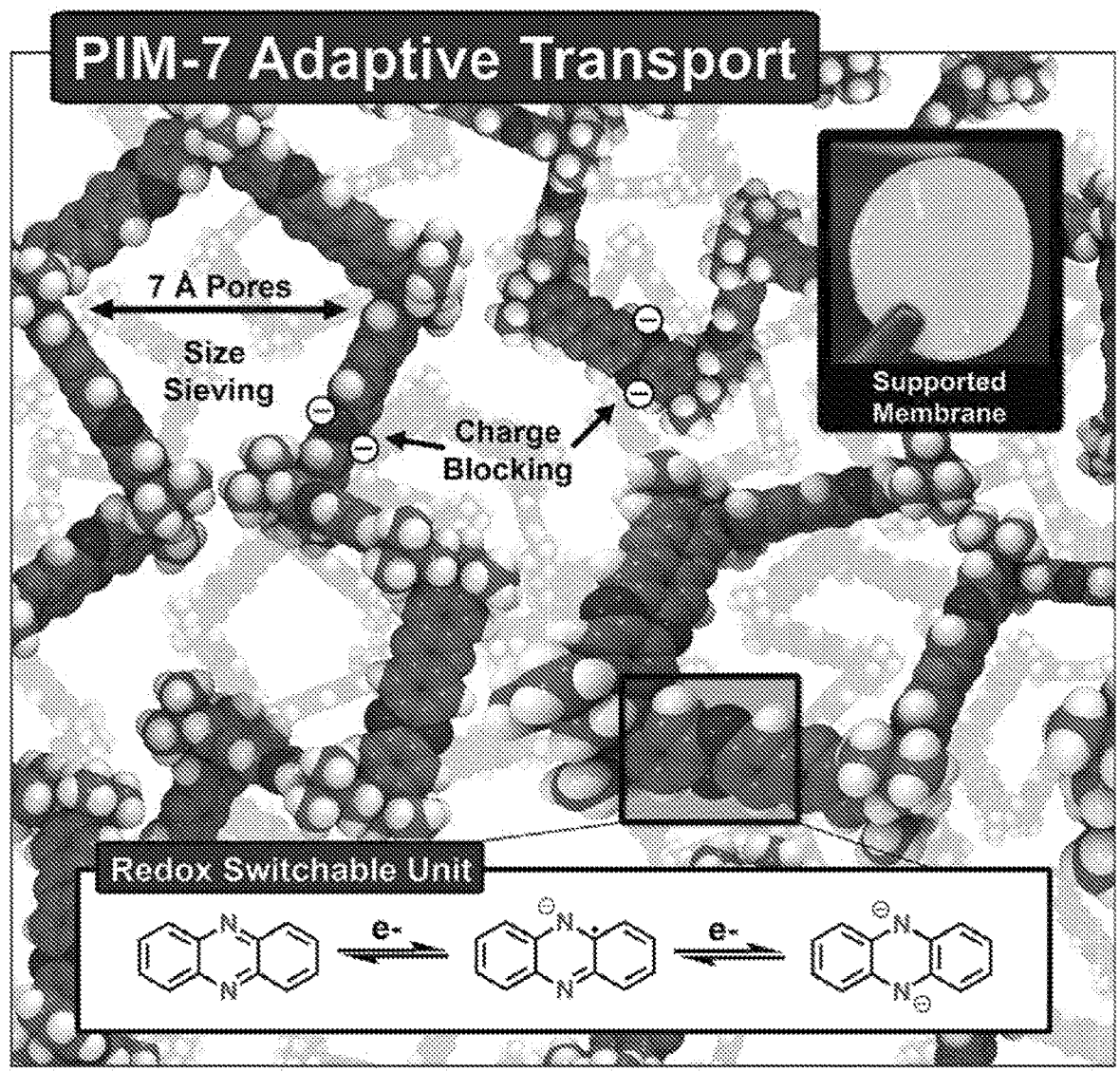
FIG. 30 provides a schematic illustration of a modified polymer of intrinsic microporosity membrane including identification of a chemical structure of a charged moiety and a photograph of an example membrane.

Figure captions. FIG. 30: Hybrid membrane design for achieving both size and charge selectivity. This Example introduces a platform based on polymers of intrinsic microporosity that demonstrates selectivity based on charge exclusion can be achieved by incorporation of an in situ activated redox switch into the polymer backbone as well as by size selectivity imparted by virtue of the micropore architecture.

FIG. 31: Library of model compounds and calculated reduction potentials used to guide the selection of redox switches for membrane incorporation. PIM-7 (highlighted) was selected for its ideal combination of reduction potential, synthetic accessibility and membrane processability.

FIG. 32A: Cyclic voltammogram of the PIM-7 polymer showing two reversible reductions at $E_{1/2}$=3.05 and 2.85 V vs. Li/Li$^-$. FIG. 32B: UV-Vis spectra of the PIM-7 polymer before and after chemical reduction with $Li_2$ S.

FIG. 33A: Time-evolution of the concentration of PS in the permeate (left) of H-cells configured with either a Celgard (grey), PIM-1 (green) or a PIM-7 (purple) membrane. FIG. 33B: Time-evolution of the concentration of PS in the permeate (left) of H-cells configured with PIM-7 membranes pre reduced for 0 h (circle), 12 h (square) or 24 h (triangle). The retentate was charged with an initial concentration of 0.8 M S as $Li_2S_8$ in diglyme containing 0.50 M LiTFSI and 0.15 M LiNO$_3$. The concentration of PS in the permeate was determined electrochemically.

FIG. 34: Discharge capacity vs. cycle number at C/4 rate for cells constructed with supported PIM-1 and PIM-7.

Methods. Materials: Diglyme (G2), 3,3,3',3'-tetramethyl-1,1'-spirobiindane-5,5',6,6'-tetraol and tetrafluoroterephthalonitrile were purchased from Sigma Aldrich. Sulfur (Puratronic, 99.9995% (metals basis)), lithium sulfide (99.9% (metals basis)), and lithium metal were purchased from Alfa Aesar. Lithium bis(trifluoromethanesulfonyl)imide (LiTFSI) was purchased from 3M. Celgard 2535 membrane was purchased from MTI Corporation. Ketjenblack EC-600JD was purchased from AkzoNobel.

Membrane preparation: Supported membranes of PIM-1 and PIM-7 were prepared. Electrolyte and catholyte preparation: The supporting electrolyte formulation for all battery cycling and conductivity measurements was 0.50 M LiTFSI. LiNO$_3$ was added to the electrolyte only for the crossover experiments detailed below. LiTFSI was dried for 16 h under vacuum at 150° C. LiNO$_3$ was dried for 16 h under vacuum at 110° C. Diglyme was tested for peroxides prior to use; if any were measured, it was stirred with alumina, filtered, and sparged with argon. Diglyme was dried with activated 3 Å molecular sieves until it measured <20 ppm H$_2$O. Electrolyte was tested for water content and confirmed to contain <30 ppm water before use. Solutions of $Li_2S_8$ (2.50 mol S L$^{-1}$ in electrolyte) were prepared by mixing Li$_2$S (0.287 g, 6.25 mmol), sulfur (1.40 g, 5.47 mmol), and 20 mL of electrolyte and heating at 60° C. until all solids were dissolved. $Li_2S_8$ solutions were kept at 60° C. in order to prevent precipitation of insoluble species and cooled to room temperature prior to use. Cathode slurry were prepared with 5% w/w Ketjenblack and 0.5 M $Li_2S_8$ solution and sonicated for 30 min at 50° C.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A modified polymer of intrinsic microporosity comprising a polymer of intrinsic microporosity having a plurality of repeat units, wherein at least one of the repeat units includes one or more negative charges; and wherein at least one of the repeat units includes one or more charged moieties selected from the group consisting of:

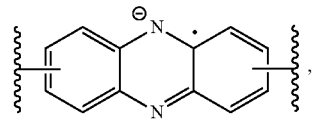

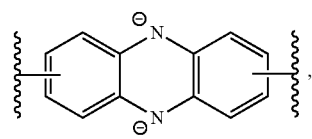

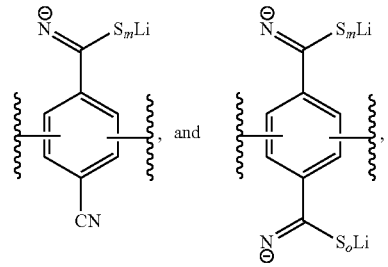

where subscript m and subscript o are independently integers selected from 1 to 8.

2. The modified polymer of intrinsic microporosity of claim 1, wherein at least one of the repeat units further includes a negatively charged oxygen site, a negatively charged sulfur site, a negatively charged carbon site, or any combination thereof.

3. The modified polymer of intrinsic microporosity of claim 1, wherein at least one the repeat units have a structure selected from the group consisting of:

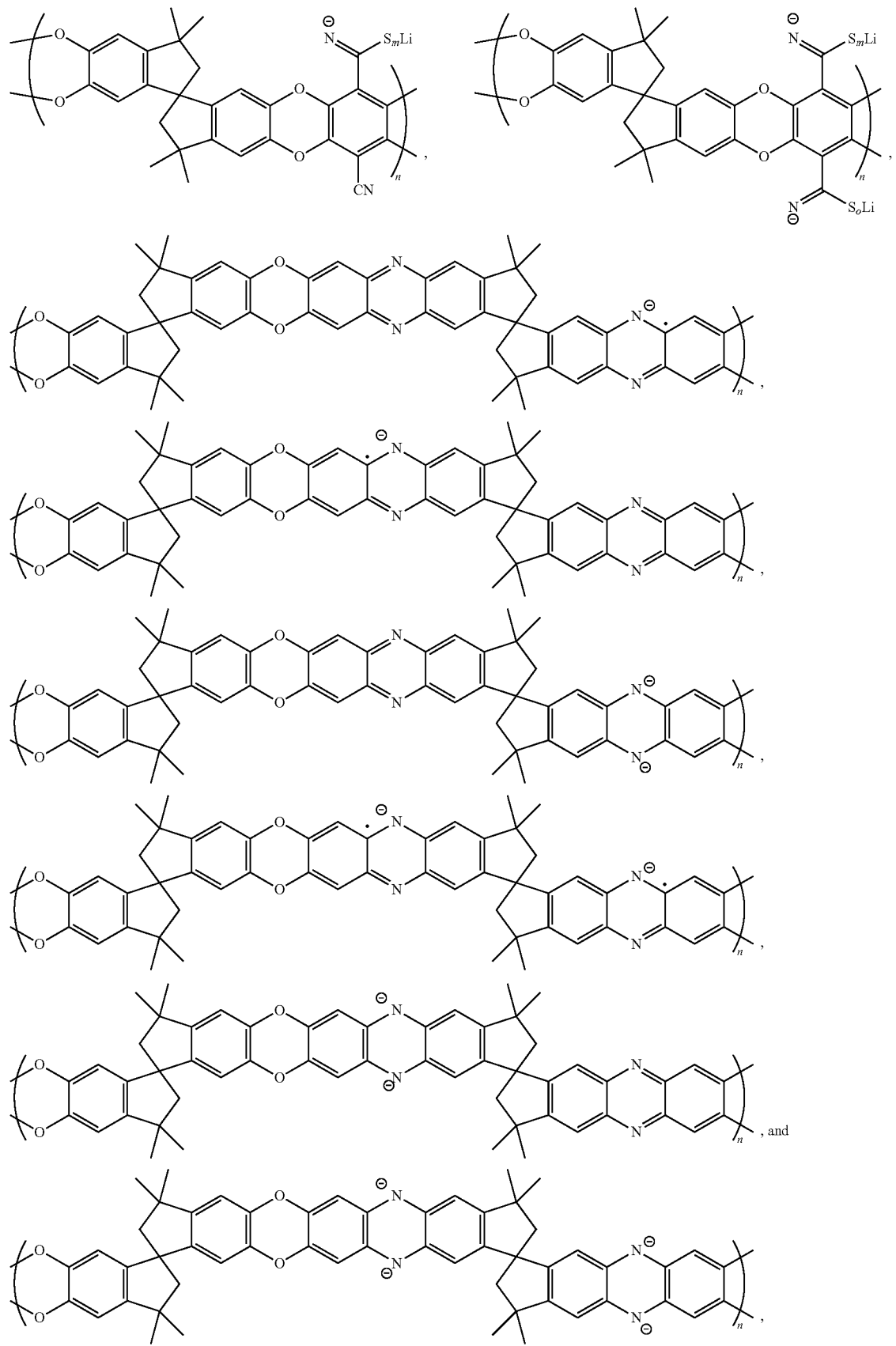

where subscript m and subscript o are independently integers selected from 1 to 8, and wherein subscript n is an integer selected from 10 to 1000.

4. The modified polymer of intrinsic microporosity of claim 1, wherein the polymer of intrinsic microporosity is crosslinked or wherein at least one repeat unit is crosslinked with a non-adjacent repeat unit.

5. The modified polymer of intrinsic microporosity of claim 1, wherein at least one repeat unit is crosslinked with a non-adjacent repeat unit by a crosslinker selected from the group consisting of 2,6-bis(4-azidobenzylidene)cyclohexanone, 2,6-bis(4-azidobenzylidene)-4-methylcyclohexanone, 2,6-bis(4-azidobenzylidene)-4-ethylcyclohexanone, 4-azidophenylsulfone, and any combination of these.

6. The modified polymer of intrinsic microporosity of claim 1, wherein a surface area of the polymer of intrinsic microporosity is at least 300 $m^2/g$.

7. The modified polymer of intrinsic microporosity of claim 1, further comprising a support membrane in contact with the polymer of intrinsic microporosity.

8. An electrochemical cell comprising:
an anode;
an anode electrolyte in contact with the anode;
a separator in contact with the anode electrolyte, wherein the separator comprises a polymer of intrinsic microporosity;
a cathode electrolyte in contact with the separator; and
a cathode in contact with the cathode electrolyte; and
wherein the polymer of intrinsic microporosity has a plurality of repeat units, wherein at least one of the repeat units includes one or more negative charges; and wherein at least one of the repeat units includes one or more charged moieties selected from the group consisting of:

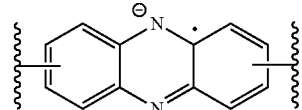

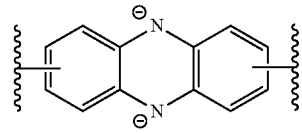

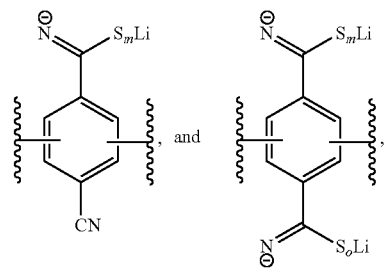, and where subscript m and subscript o are independently integers selected from 1 to 8; or at least one the repeat units have a structure selected from the group consisting of:

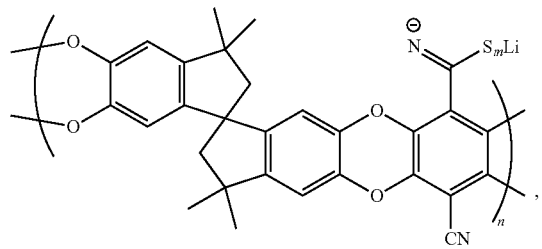 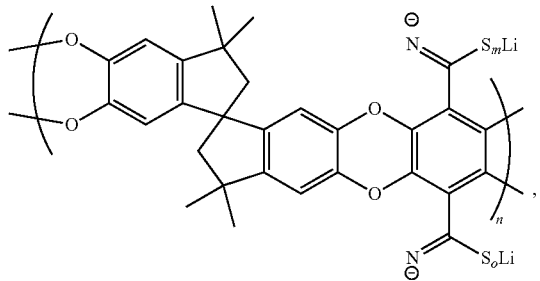

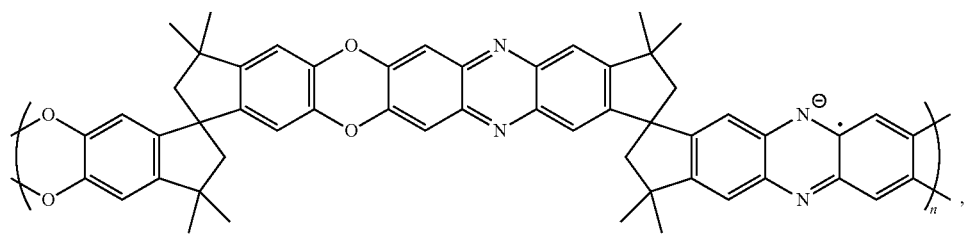

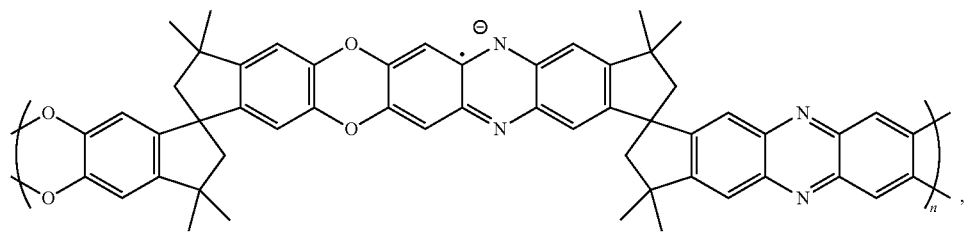

-continued

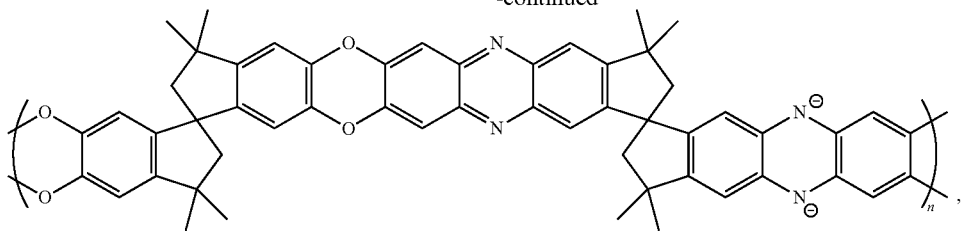

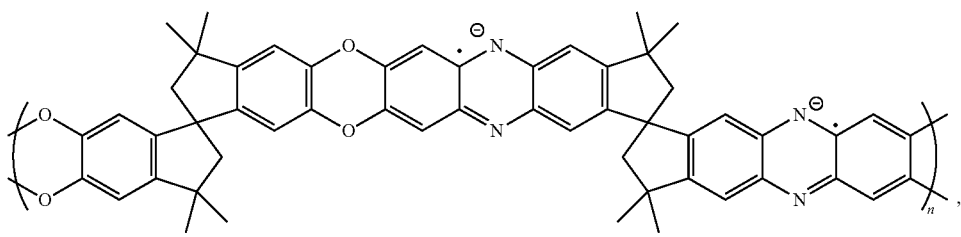

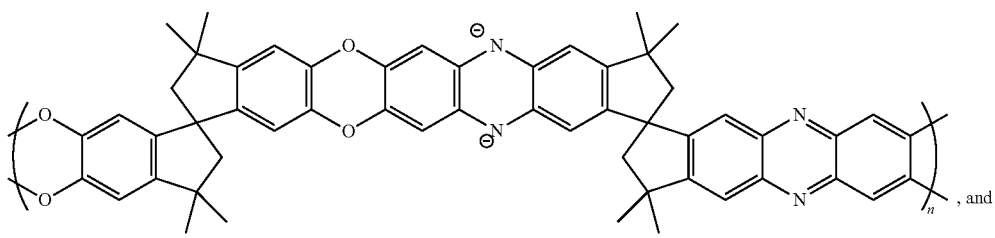, and

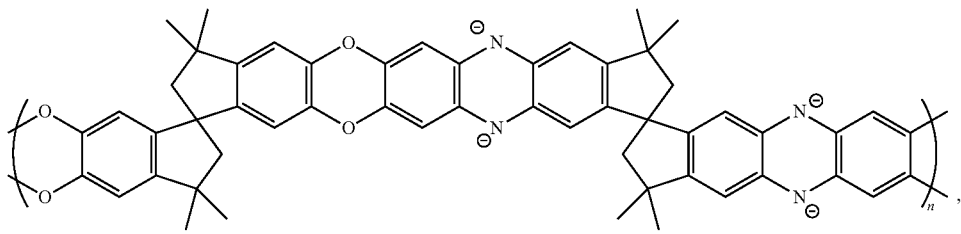, where subscript m and subscript o are independently integers selected from 1 to 8, and wherein subscript n is an integer selected from 10 to 1000.

9. The electrochemical cell of claim 8, wherein the separator further comprises a support membrane in contact with the polymer of intrinsic microporosity.

10. The electrochemical cell of claim 9, wherein the support membrane comprises a polymer selected from the group consisting of: polyethylene, polyethylene copolymers, polypropylene, polypropylene copolymers, polyacrylonitrile, polyacrylonitrile copolymers, poly(vinylidene fluoride), poly(tetrafluoroethylene), poly(vinyl chloride), poly(vinylchloride) copolymers, poly(hexafluoropropylene), poly(hexafluoropropylene) copolymers, polyaramide, any combination thereof, and any copolymers thereof.

11. The electrochemical cell of claim 9, wherein the support membrane has a melting temperature, and wherein exposing the support membrane to a temperature exceeding the melting temperature causes at least a portion of the support membrane to melt and close pores within the separator.

12. The electrochemical cell of claim 9, wherein at least one of the repeat units further includes a negatively charged oxygen site, a negatively charged sulfur site, a negatively charged carbon site, or any combination thereof.

13. The electrochemical cell of claim 9, wherein the polymer of intrinsic microporosity is crosslinked or wherein at least one repeat unit is crosslinked with a non-adjacent repeat unit.

14. The electrochemical cell of claim 9, wherein a surface area of the polymer of intrinsic microporosity is at least 300 $m^2/g$.

15. A modified polymer of intrinsic microporosity comprising a polymer of intrinsic microporosity having a plurality of repeat units, wherein at least one of the repeat units includes one or more negative charges; and
wherein at least one the repeat units have a structure selected from the group consisting of:

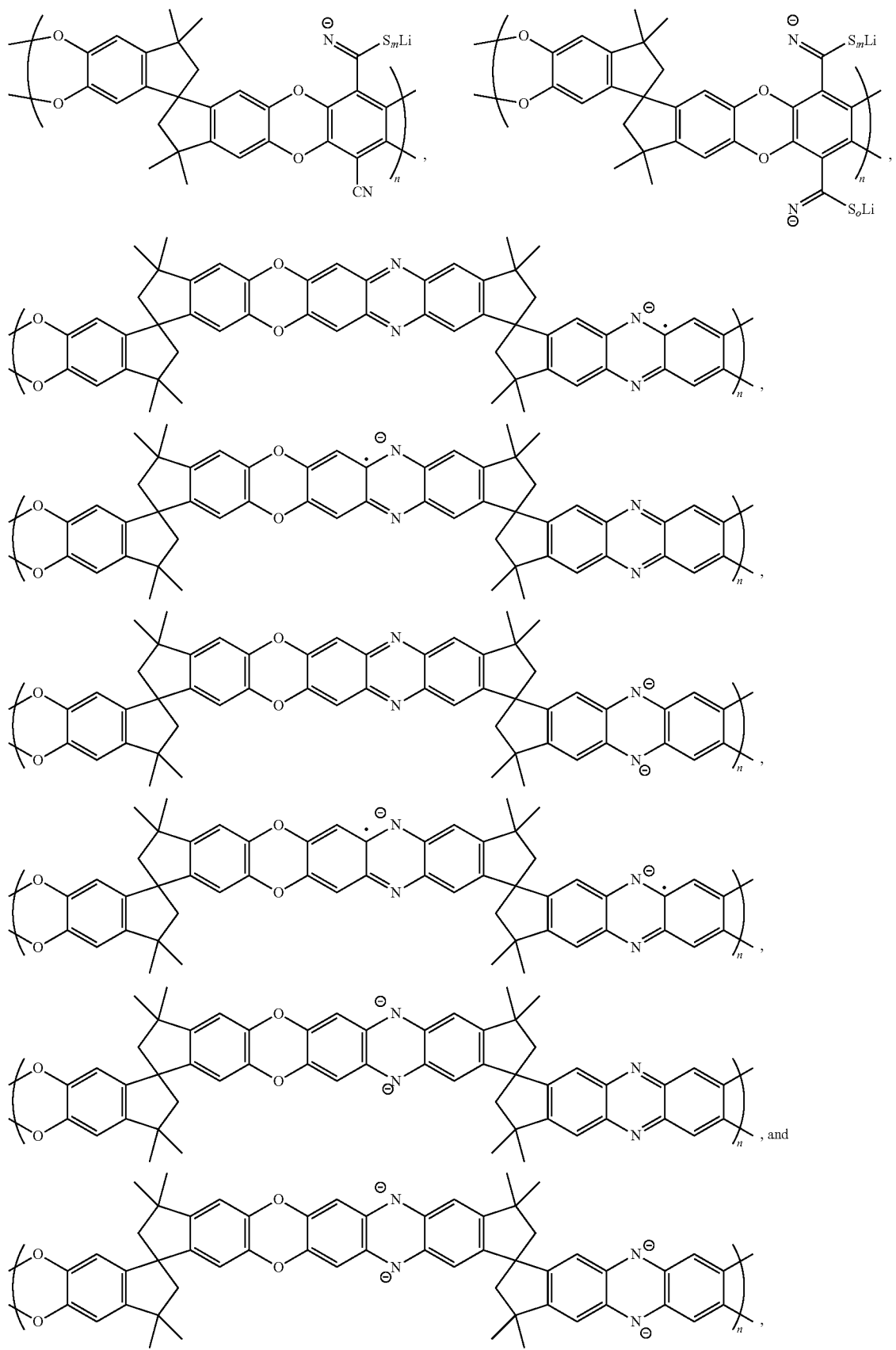

where subscript m and subscript o are independently integers selected from 1 to 8, and wherein subscript n is an integer selected from 10 to 1000.

16. The modified polymer of intrinsic microporosity of claim 15, wherein at least one of the repeat units further includes a negatively charged oxygen site, a negatively charged sulfur site, a negatively charged carbon site, or any combination thereof.

17. The modified polymer of intrinsic microporosity of claim 15, wherein the polymer of intrinsic microporosity is crosslinked or wherein at least one repeat unit is crosslinked with a non-adjacent repeat unit.

18. The modified polymer of intrinsic microporosity of claim 15, wherein at least one repeat unit is crosslinked with a non-adjacent repeat unit by a crosslinker selected from the group consisting of 2,6-bis(4-azidobenzylidene)cyclohexanone, 2,6-bis(4-azidobenzylidene)-4-methylcyclohexanone, 2,6-bis(4-azidobenzylidene)-4-ethylcyclohexanone, 4-azidophenylsulfone, and any combination of these.

19. The modified polymer of intrinsic microporosity of claim 15, wherein a surface area of the polymer of intrinsic microporosity is at least 300 $m^2/g$.

20. The modified polymer of intrinsic microporosity of claim 15, further comprising a support membrane in contact with the polymer of intrinsic microporosity.

* * * * *